(12) United States Patent
Subbiah et al.

(10) Patent No.: US 9,803,216 B2
(45) Date of Patent: Oct. 31, 2017

(54) GENETICALLY-ENGINEERED NEWCASTLE DISEASE VIRUS AS AN ONCOLYTIC AGENT, AND METHODS OF USING SAME

(75) Inventors: Elankumaran Subbiah, Blacksburg, VA (US); Siba K. Samal, College Park, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 13/607,445

(22) Filed: Sep. 7, 2012

(65) Prior Publication Data

US 2014/0186303 A1 Jul. 3, 2014

Related U.S. Application Data

(62) Division of application No. 11/808,003, filed on Jun. 5, 2007, now abandoned.

(60) Provisional application No. 60/803,924, filed on Jun. 5, 2006.

(51) Int. Cl.
*C12N 15/86* (2006.01)
*C12N 7/00* (2006.01)
*A61K 35/13* (2015.01)

(52) U.S. Cl.
CPC ............... *C12N 15/86* (2013.01); *C12N 7/00* (2013.01); *A61K 35/13* (2013.01); *C12N 2760/18121* (2013.01); *C12N 2760/18143* (2013.01)

(58) Field of Classification Search
None
See application file for complete search history.

(56) References Cited

U.S. PATENT DOCUMENTS

| | | | |
|---|---|---|---|
| 6,376,236 B1 | 4/2002 | Dubensky et al. | |
| 6,730,512 B2* | 5/2004 | Chang | A01K 67/0271 435/320.1 |
| 7,056,689 B1 | 6/2006 | Lorence et al. | |
| 7,223,389 B2* | 5/2007 | Zakay-Rones et al. | 424/93.2 |
| 7,615,209 B2* | 11/2009 | Zakay-Rones | A61K 35/768 424/214.1 |

OTHER PUBLICATIONS

Huijie Bian et al., "Selective Gene Transfer in Vitro to Tumor Cells Via Recombinant Newcastle Disease Virus", Cancer Gene Therapy, 2005, vol. 12, pp. 295-303.
Krishnamurthy et al., "Recovery of a Virulent Strain of Newcastle Disease Virus from Cloned cDNA: Expression of a Foreign Gene Results in Growth Retardation and Attenuation", Virology, 2000, vol. 278, pp. 168-182.
Simone Fulda et al., "Smac Agonists Sensitize for Apo2L/TRAIL- or Anticancer Drug-Induced Apoptosis and Induce Regression of Malignant Glioma in Vivo", Nature Medicine, Aug. 2002, vol. 8, No. 8, pp. 808-815.

* cited by examiner

*Primary Examiner* — Michael Burkhart
(74) *Attorney, Agent, or Firm* — Arent Fox LLP

(57) ABSTRACT

Recombinant strains of avian paramyxovirus (APMV), such as Newcastle disease virus (NDV), are provided. Also provided are compositions comprising them, and methods of using them to lyse tumor cells and to treat cancer. In certain aspects, genetically-engineered viral strains that incorporate therapeutic transgenes are also provided. The recombinant viruses may be used in accordance with methods of providing enhanced oncolytic efficacy and delivering an oncolytic virus to tumors present in a patient. Also provided are methods for identifying a recombinant virus as an oncolytically-effective agent.

6 Claims, 43 Drawing Sheets

Fig.2
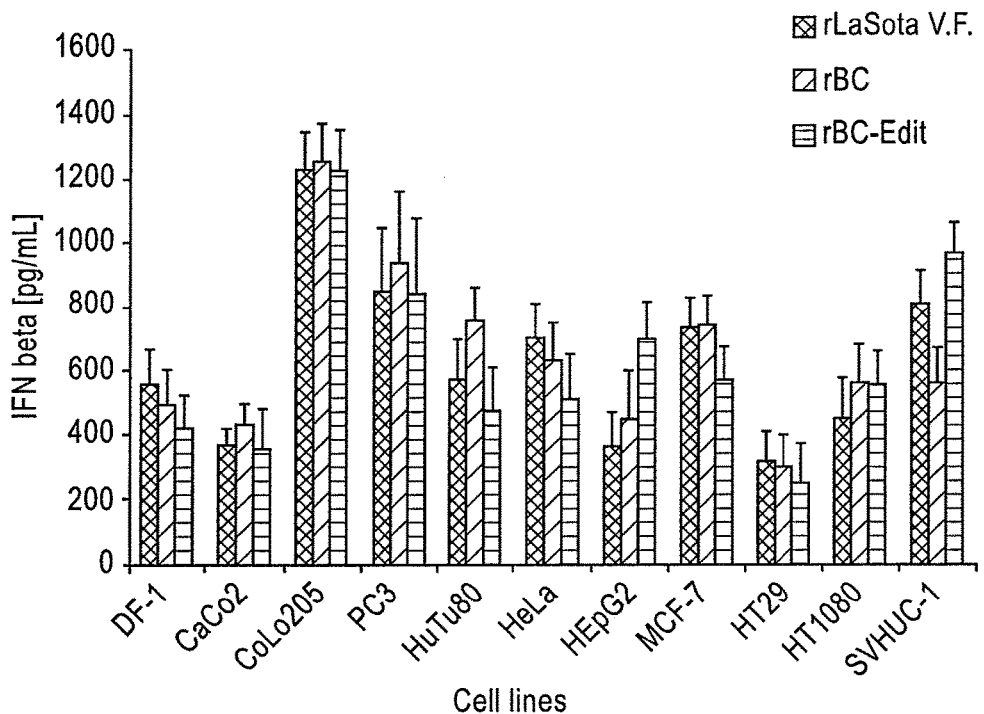
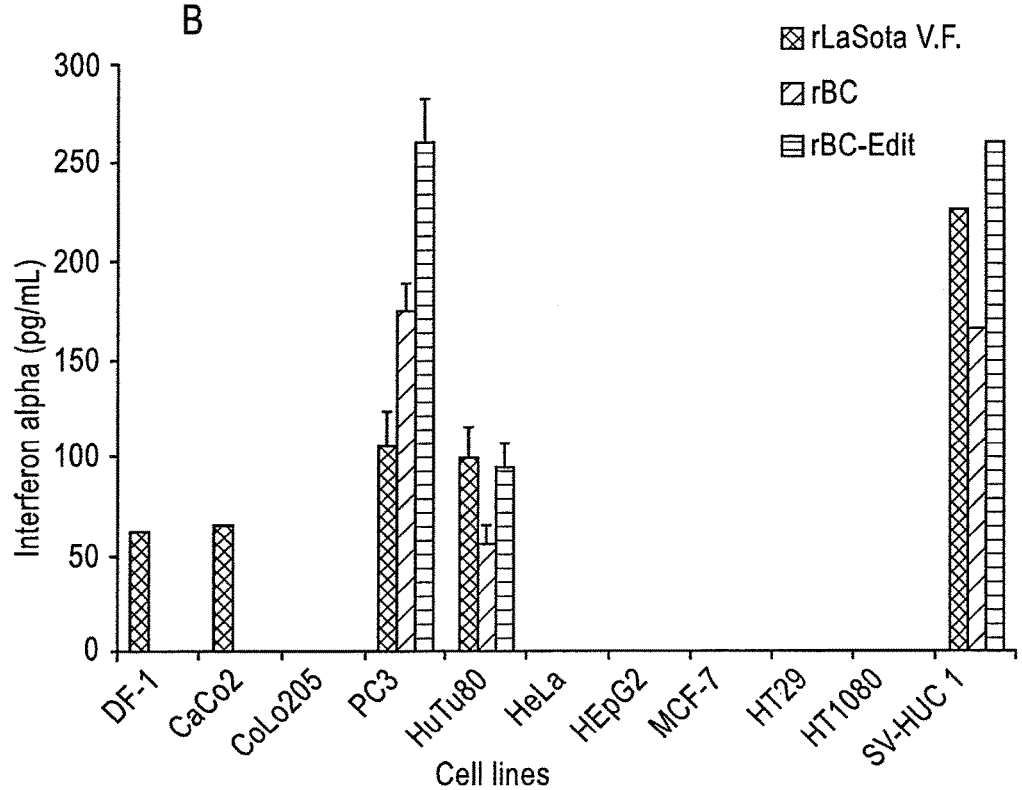

Fig.2

Fig. 13 Interferon sensitivity of recombinant NDV

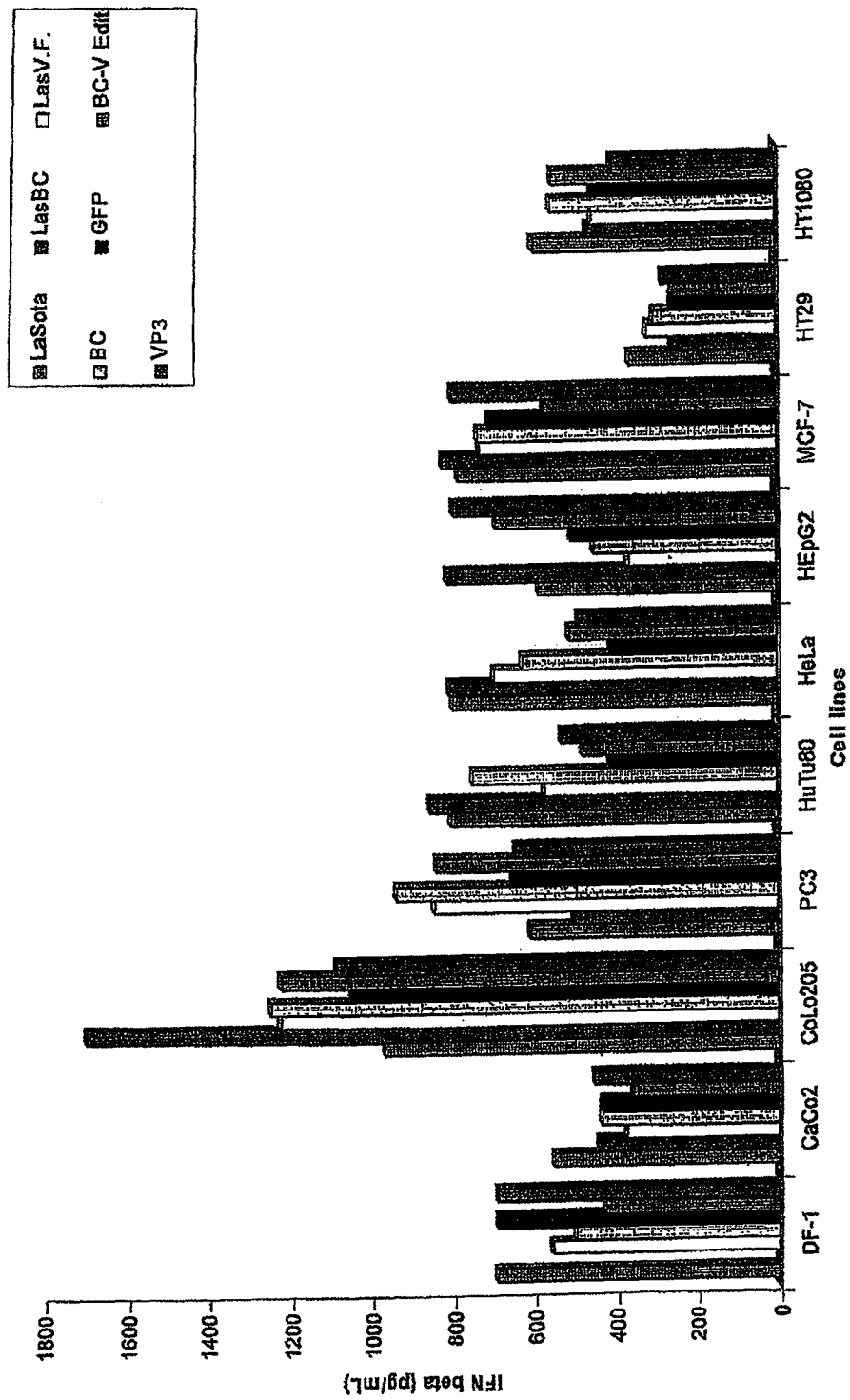
Fig. 14 IFN-Beta production in Tumor cells by rNDV

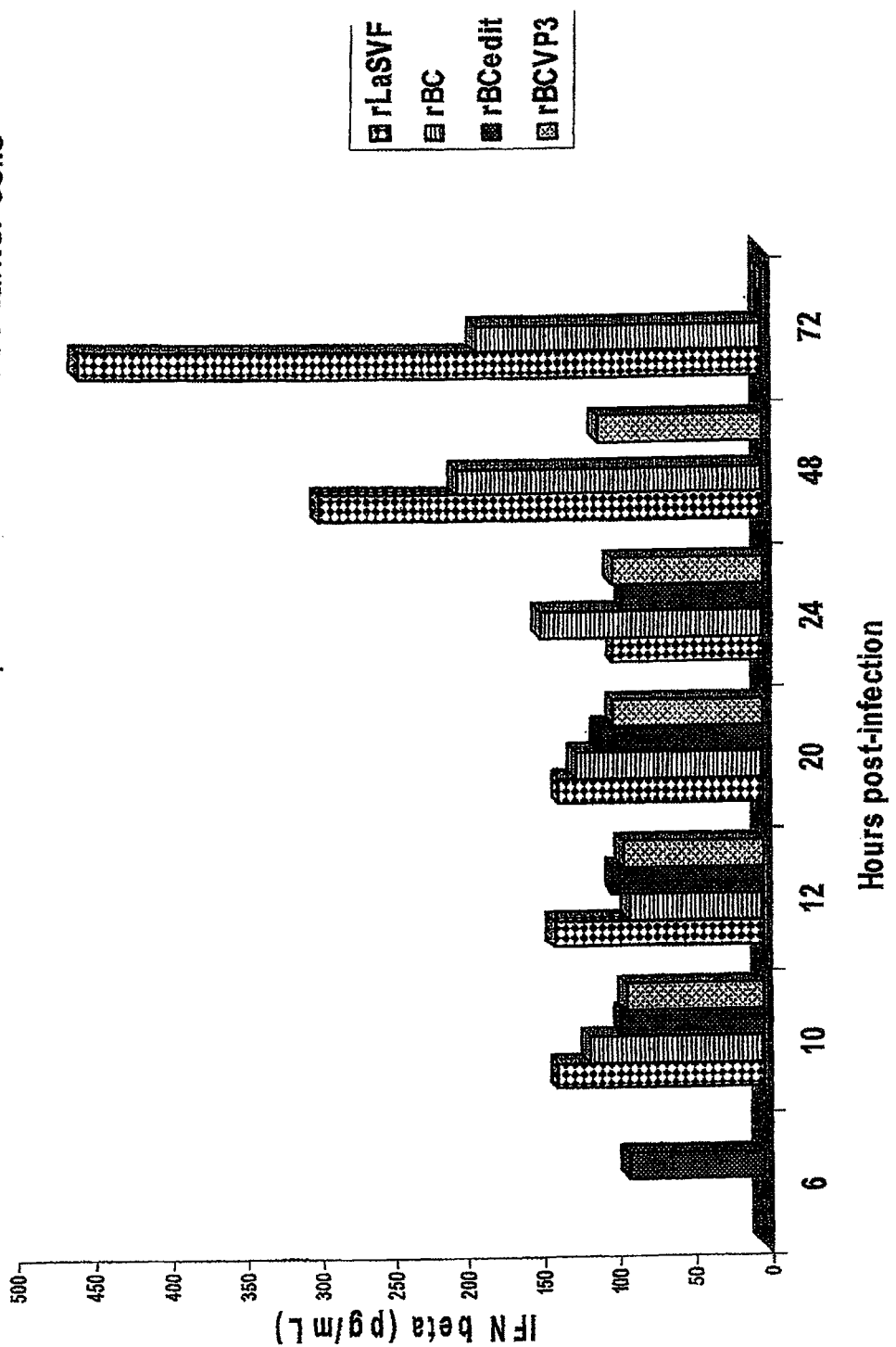

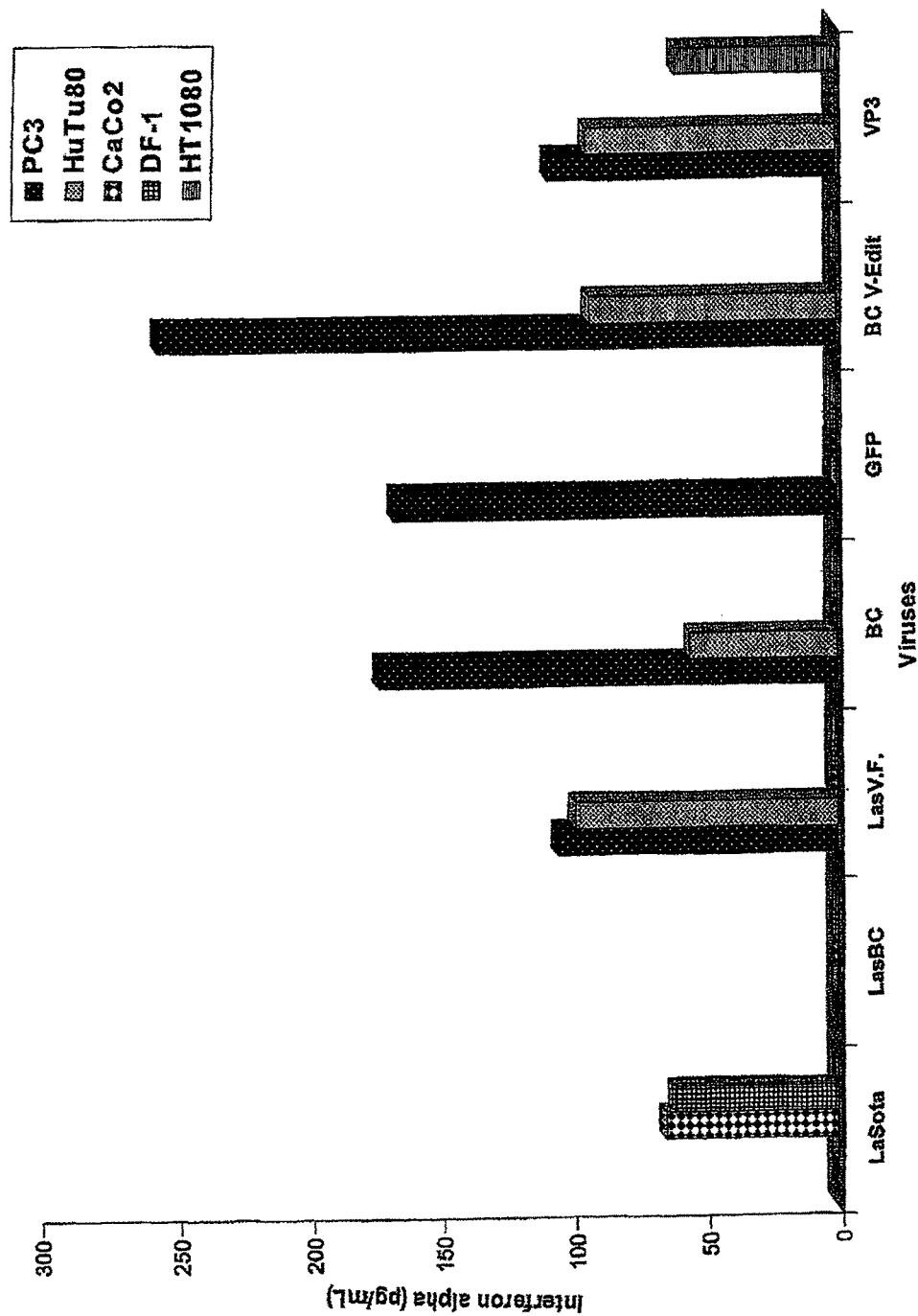
Fig. 16 IFN alpha production by rNDV in tumor cells

Fig. 17 Time course of IFN-alpha production HuTu80 cells by rNDV

Fig. 18 RANTES induction by recombinant NDV

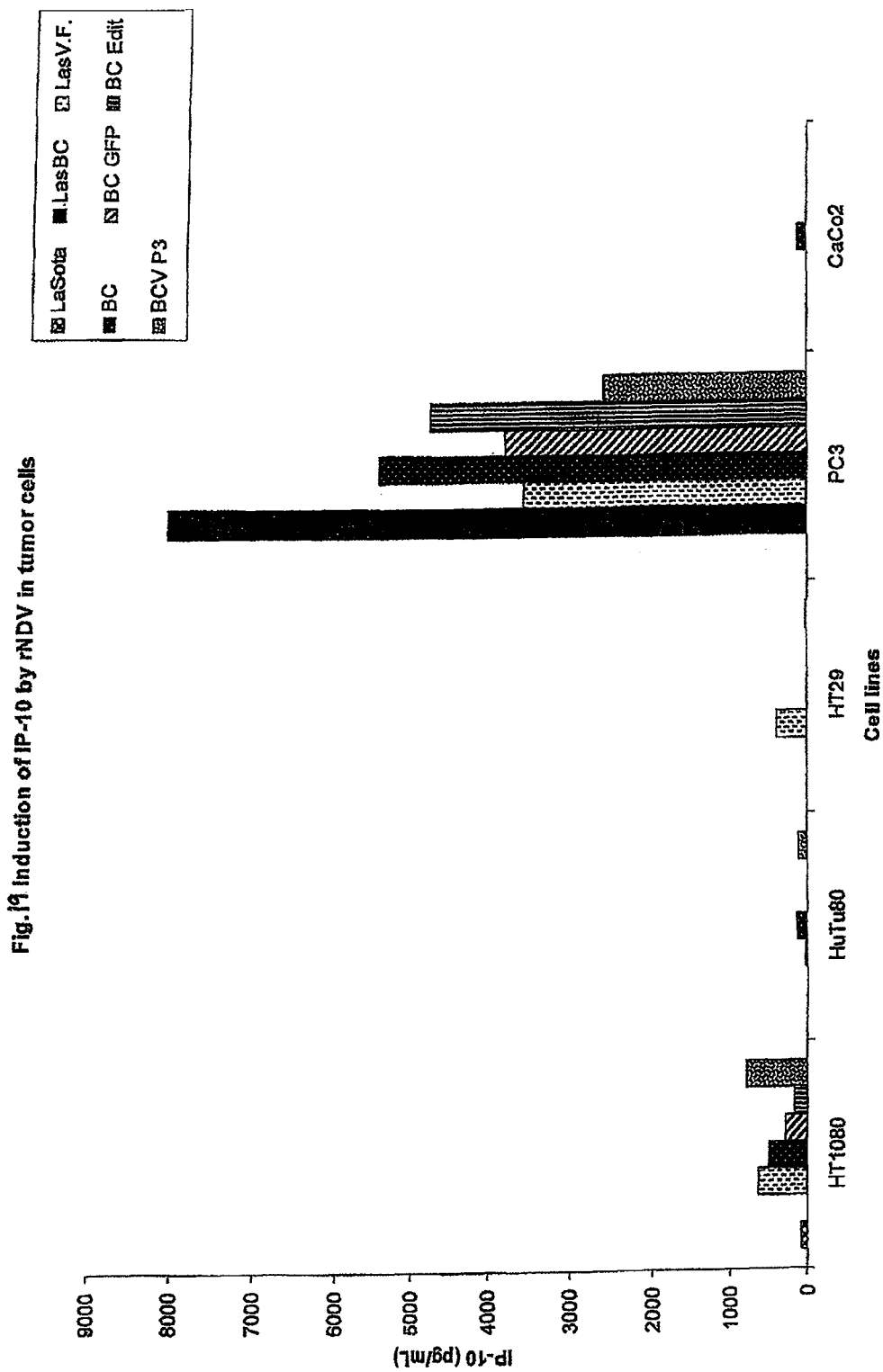

FIG. 20

Fig. 21 Expression of STAT1 alpha in HuTu80 cells after infection with rNDV.

| 6 hours | 8 hours | 10 hours | 16 hours | 24 hours | 48 hours | 72 hours |

M C L B E V C L B E V C L B E V C L B E V C L B E V C L B E V C L B E V

C-Mock infected; L-rLaSota V.F.; B-rBC; E;rBC-edit; V-rBC-CAV VP3

Fig.22 Cytopathic effects induced by rNDV in PC3 cells

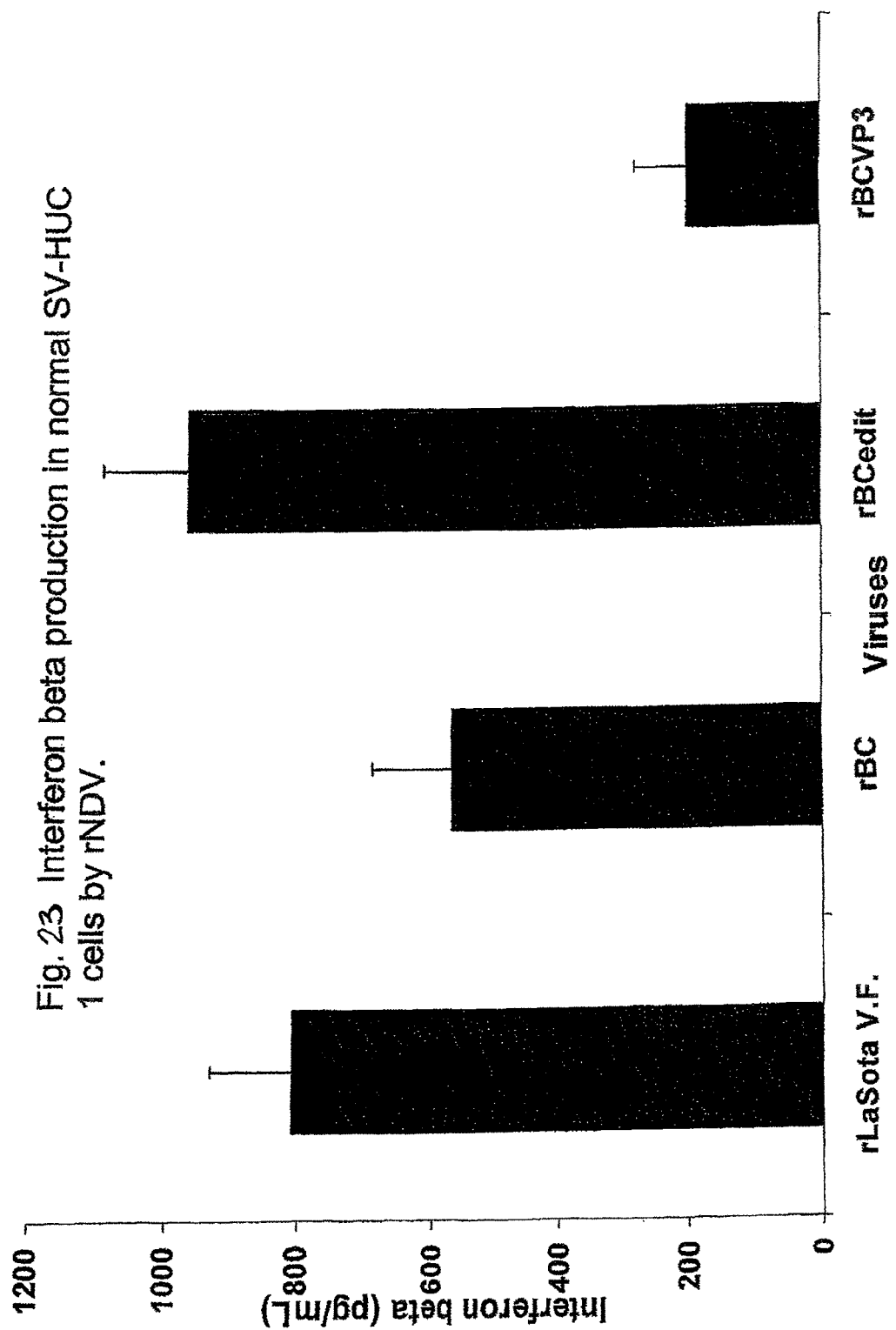
Fig. 23 Interferon beta production in normal SV-HUC 1 cells by rNDV.

Fig. 24 Effect of ras activation on the replication of rNDV

Fig. 25 Virus replication in p53 wild type cells

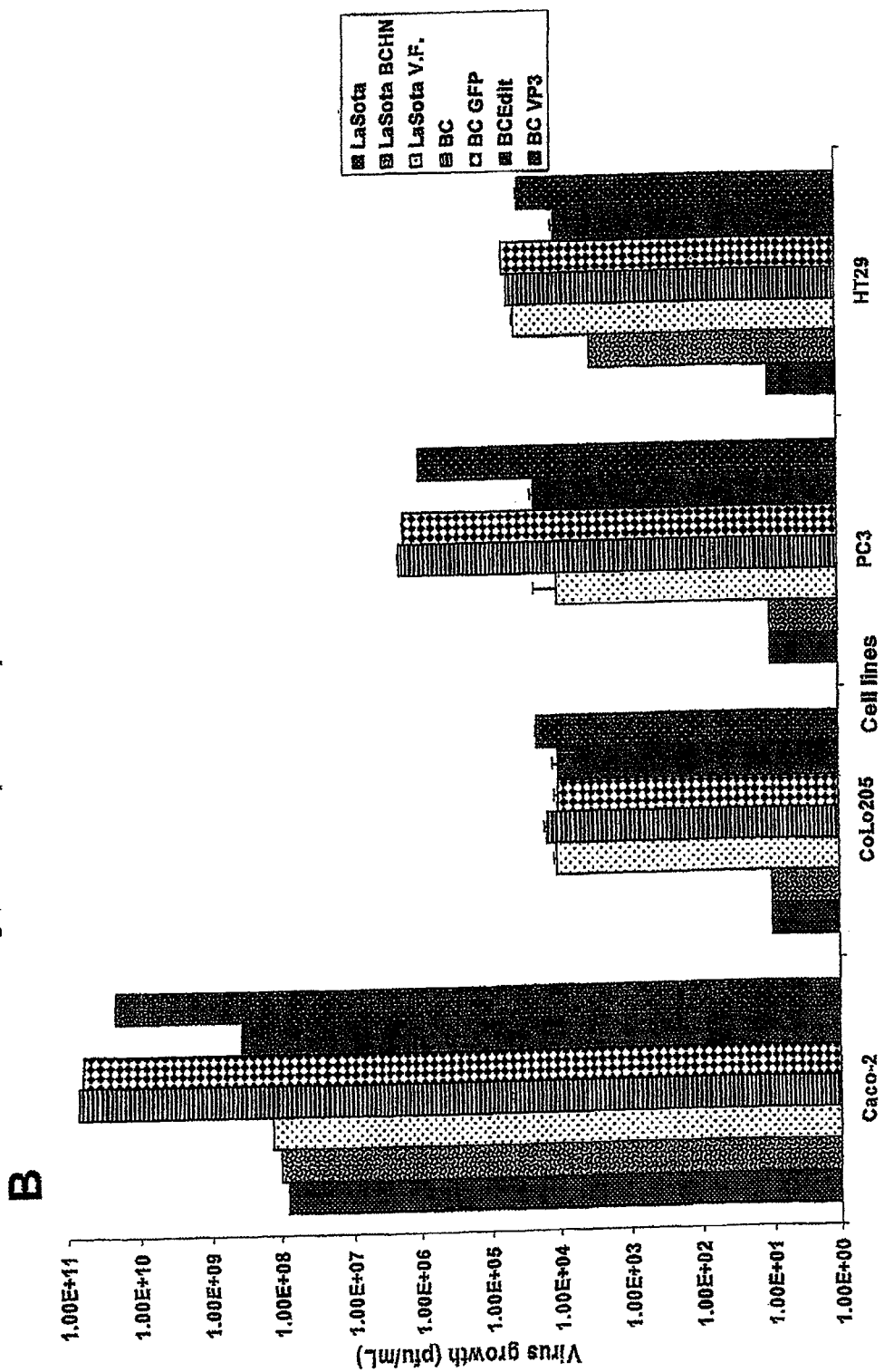
Fig. 25 Virus replication in p53 mutant cell lines

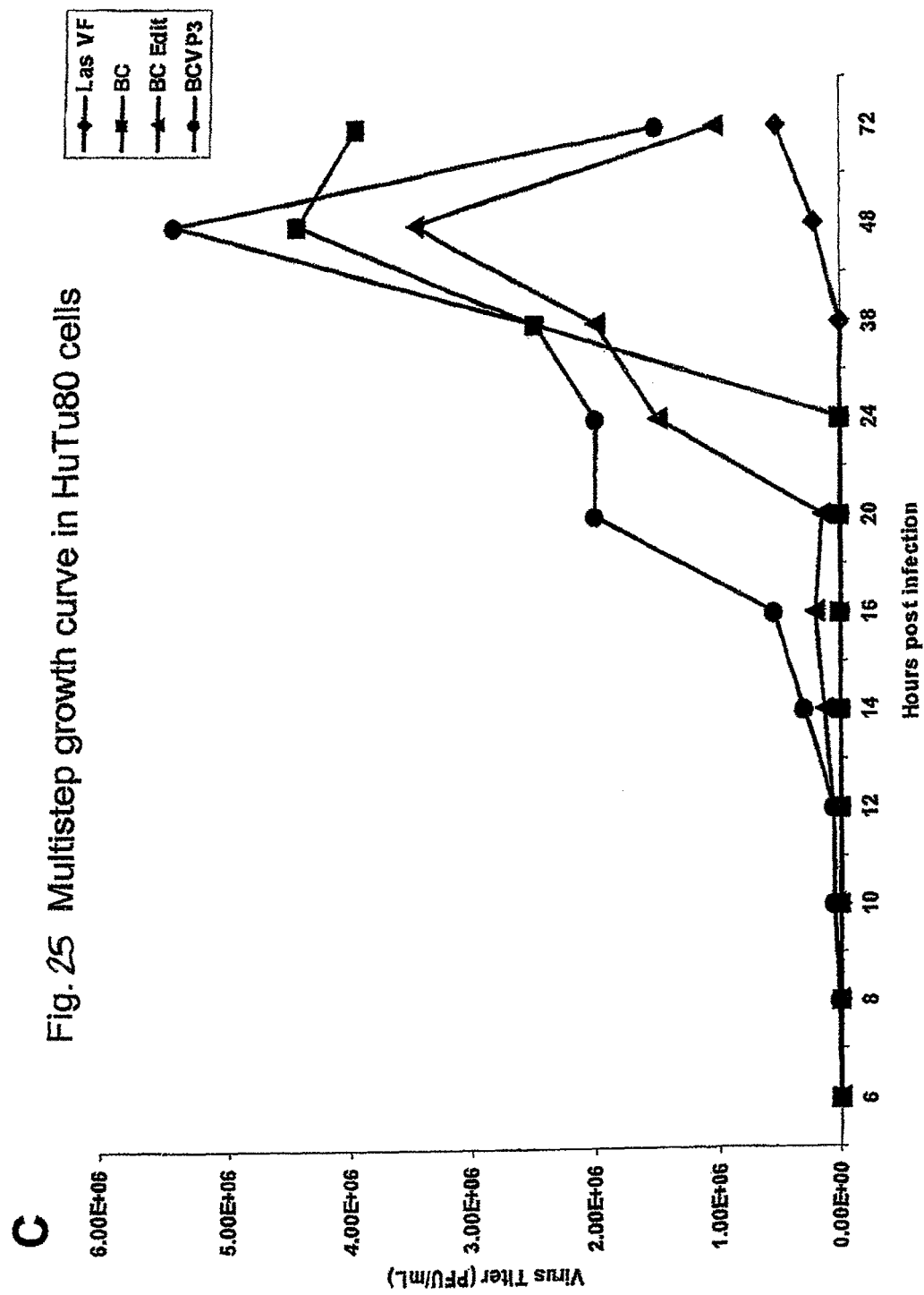
Fig. 25 Multistep growth curve in HuTu80 cells

Fig. 26 Annexin V staining in rNDV infected cells 6 h post-infection

BC-14 hours

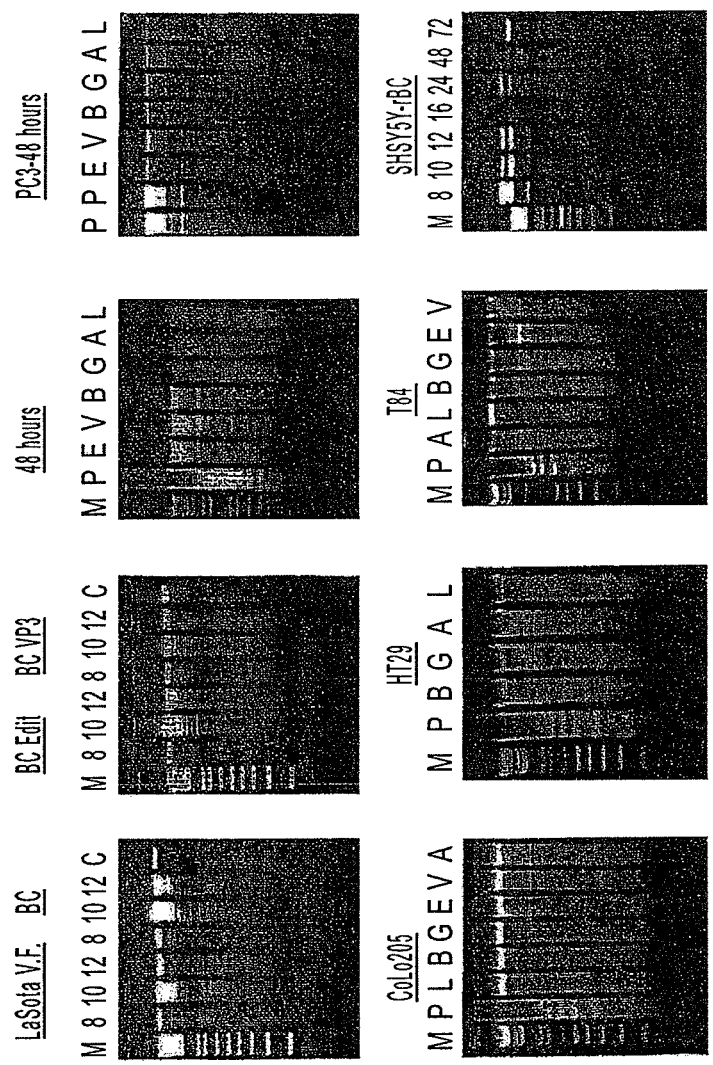
Fig.27 Apoptotic DNA laddering in tumor cell lines after infection with rNDV.A-HuTu 80 cells

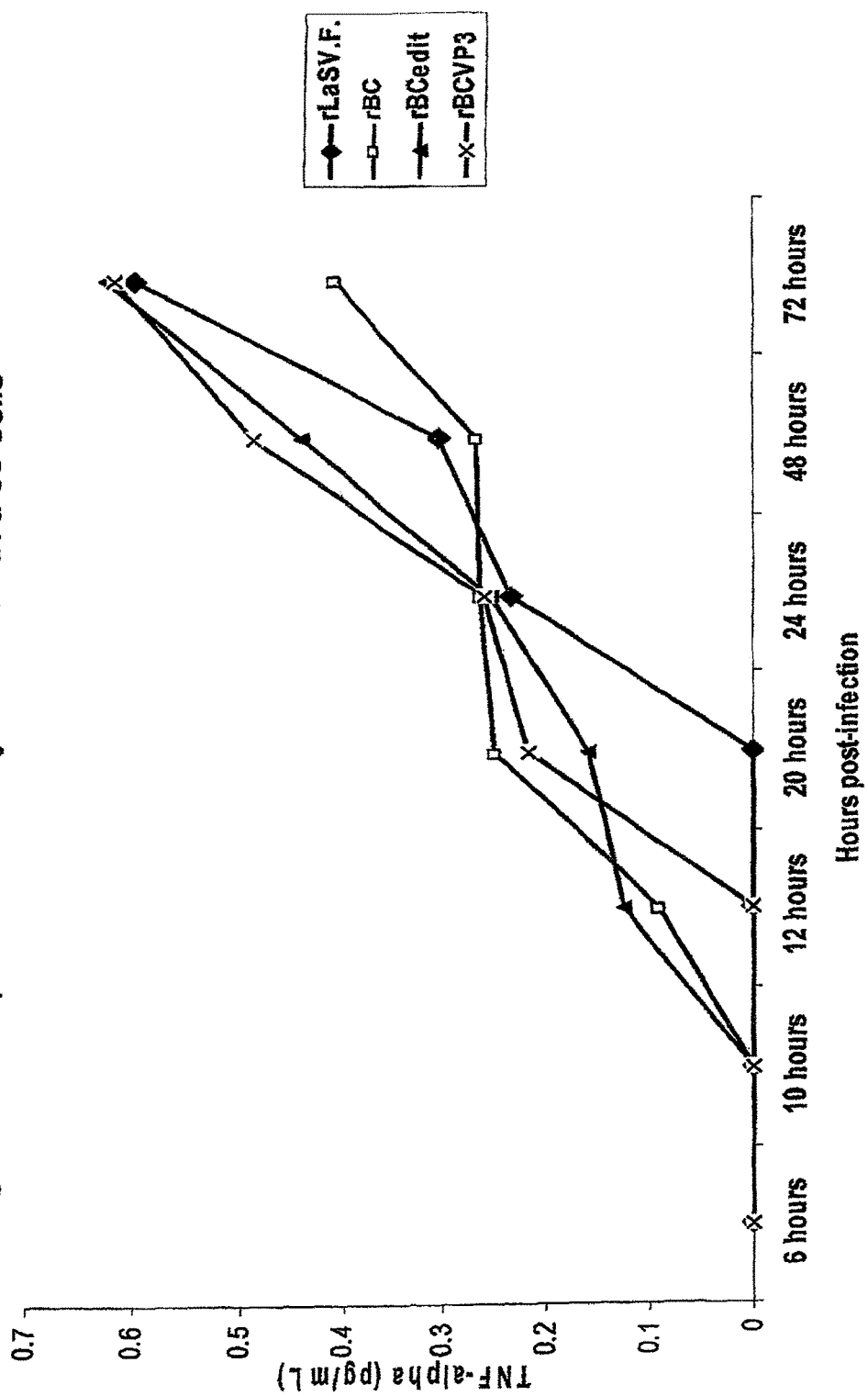
Fig. 28 TNF-alpha induction by rNDV in HuTu 80 cells

Fig. 29 TNF-alpha induction by rNDV in normal human cells (SV-HUC1)

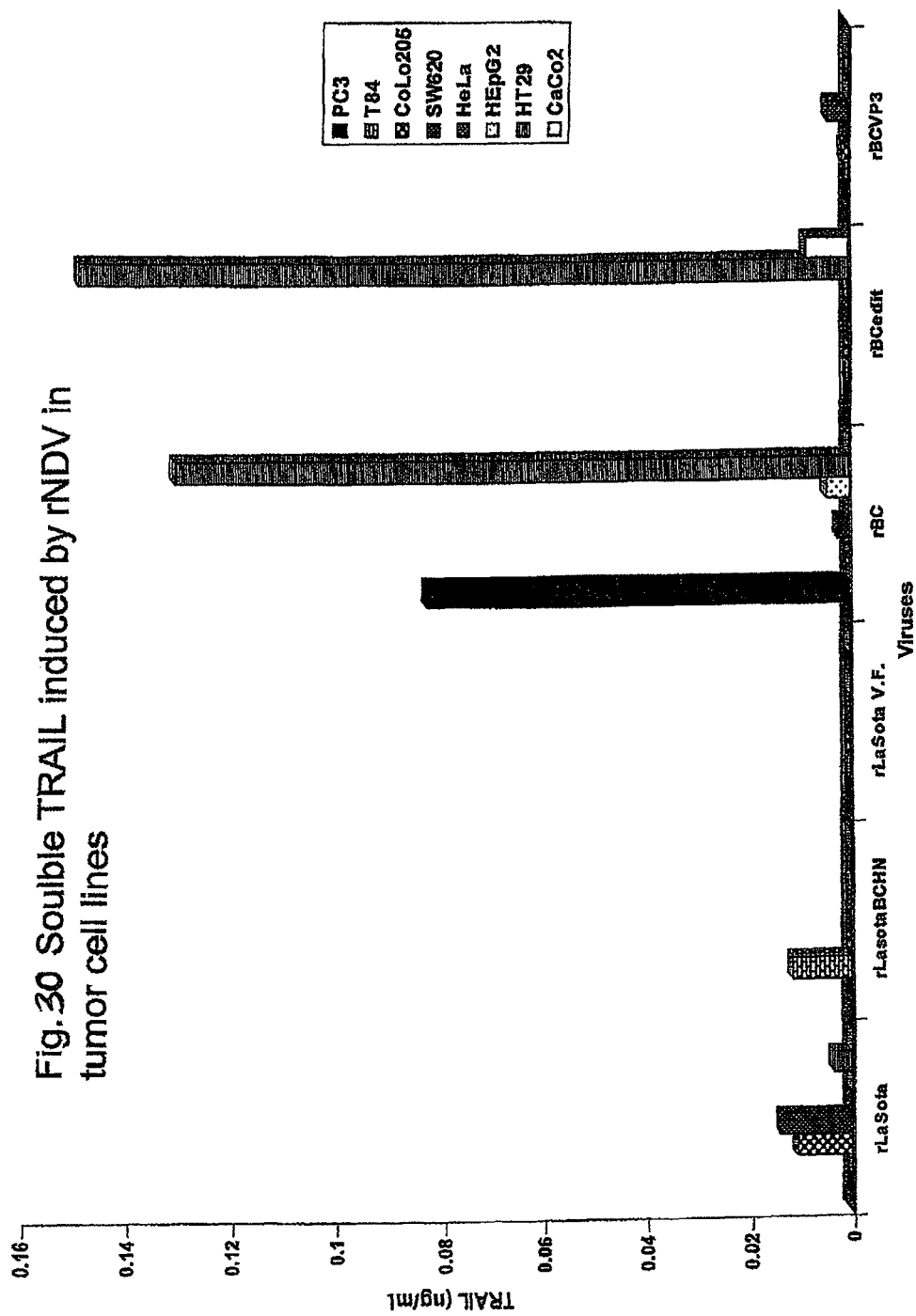
Fig. 30 Soulble TRAIL induced by rNDV in tumor cell lines

Fig. 31 Surface expression of TRAIL in rNDV-infected HuTu 80 cells

Fig. 32 Caspase-8 induction by rNDV in various tumor cell lines

Fig. 33 Kinetics of caspase-8 induction by rNDV in HuTu 80 cells

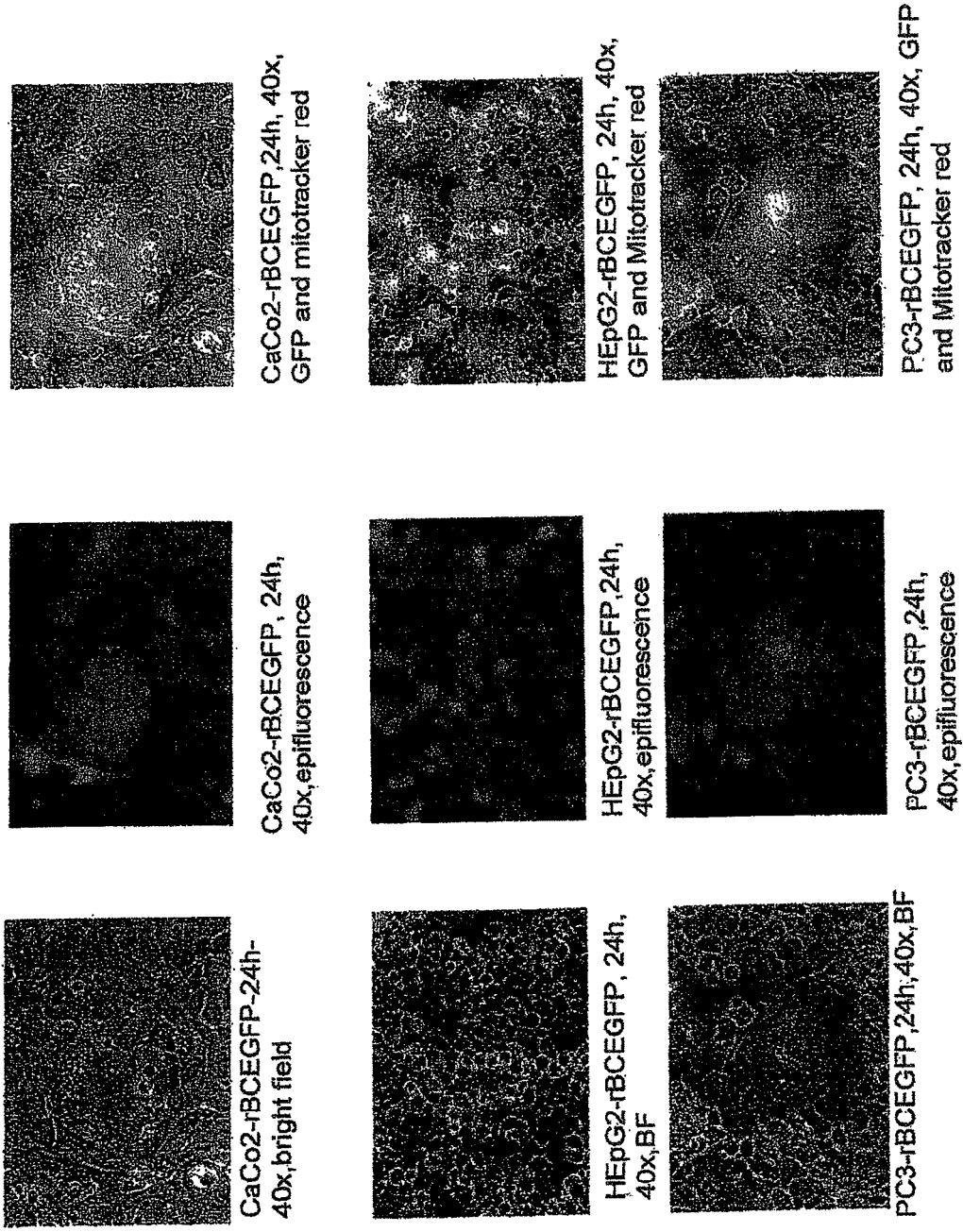

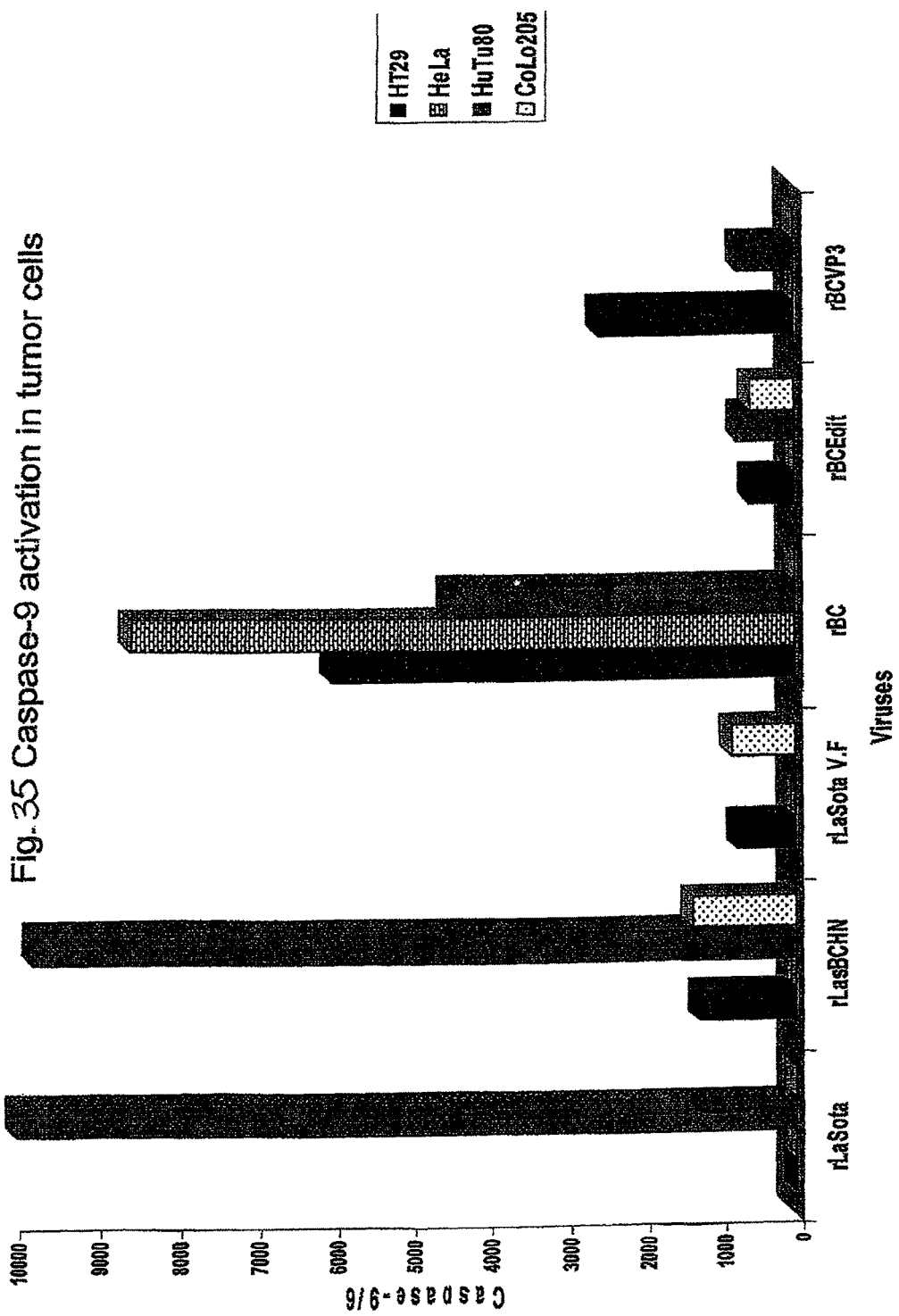

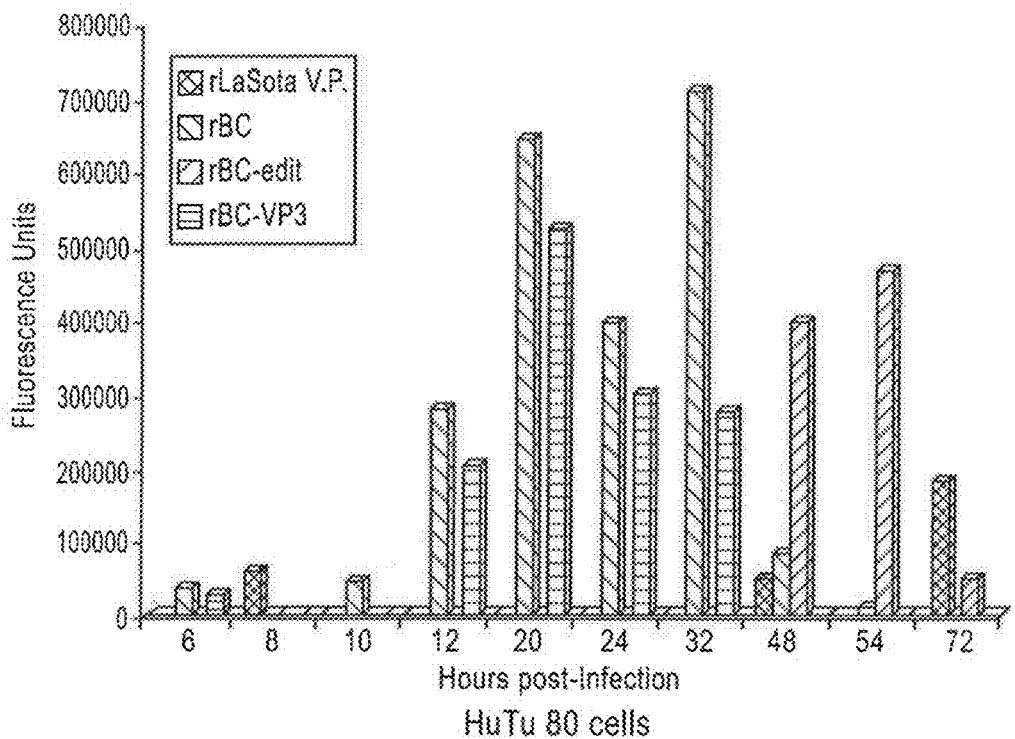
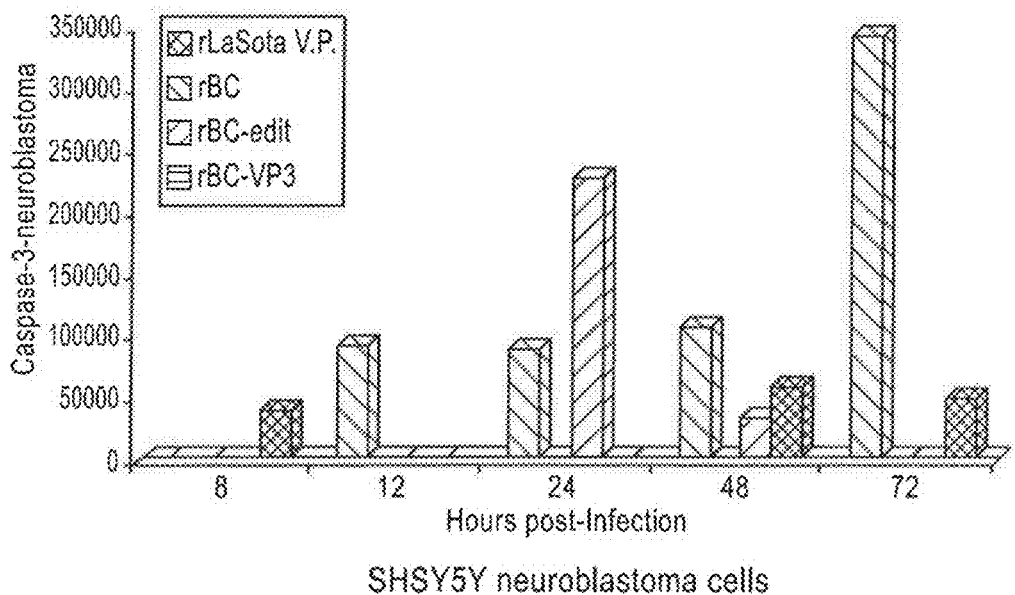
Fig. 36 Kinetics of Caspase-9 activation

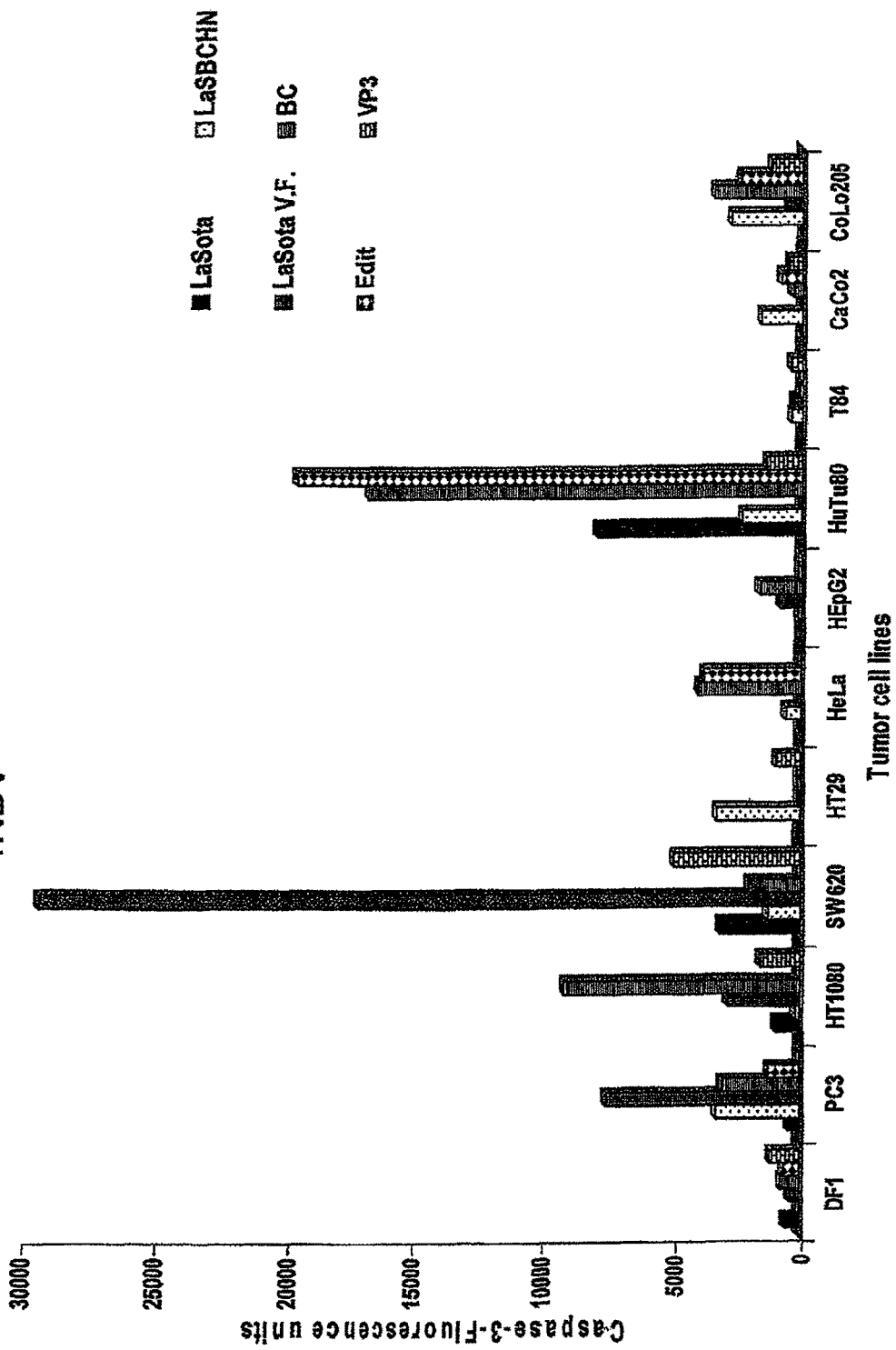

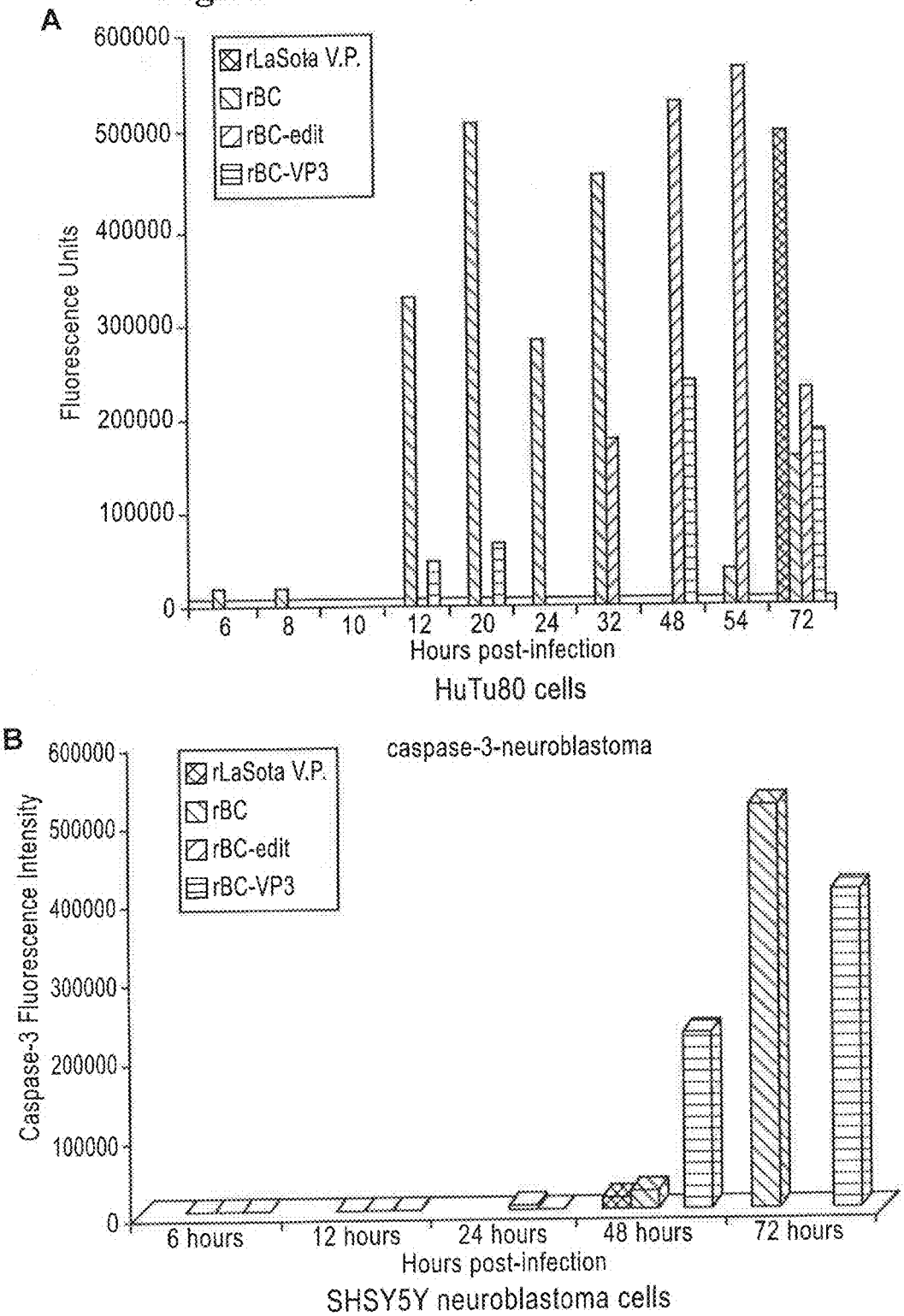
Fig. 38 Kinetics of caspase-3 activation

SEQUENCE LISTING

```
<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: PRIMER

<400> SEQUENCE: 1
gaaaggccta tggtcgagcc cccaag                                        26

<210> SEQ ID NO 2
<211> LENGTH: 27
<212> TYPE: DNA
<213> ORGANISM: Artificial Sequence
<220> FEATURE:
<223> OTHER INFORMATION: PRIMER

<400> SEQUENCE: 2
ttagcattgg acgatttatt gctgagc                                       27
```

GENETICALLY-ENGINEERED NEWCASTLE DISEASE VIRUS AS AN ONCOLYTIC AGENT, AND METHODS OF USING SAME

CROSS-REFERENCE TO RELATED APPLICATION

This is a Divisional Application, which claims the benefit of pending U.S. patent application Ser. No. 11/808,003, filed Jun. 5, 2007, which claims priority to U.S. Provisional Patent Appl. No. 60/803,924 filed Jun. 5, 2006. These prior applications are hereby incorporated by reference herein in their entirety.

BACKGROUND OF THE INVENTION

1. Field of the Invention

The present invention relates generally to recombinant strains of avian paramyxoviruses (APMV) and their use as oncolytic agents. In particular, the present invention is directed towards recombinant Newcastle disease virus (NDV) that exhibits enhanced oncolytic efficacy, and particularly to recombinant NDV that incorporates one or more additional therapeutic transgenes. The present invention also relates to methods of treating cancer by administering recombinantly-produced NDV to a patient. The present invention further relates to methods of providing targeted delivery of a recombinant NDV to specific sites in a patient, as well as methods of identifying recombinant NDV useful as oncolytic agents.

2. Description of Related Art

Naturally occurring or engineered oncolytic viruses (OVs) are emerging as novel tools for selective growth in and killing of a variety of tumor cells. OVs are multimodal therapeutics that can be engineered to have the tumor specificity of a small molecule, the potent cell killing ability of a chemotherapeutic agent, the ability to arouse the host immune system against tumor antigens, and an innate capacity to stimulate the production of host cytokines that have potential anticancer activity (Bell et al., "Oncolytic viruses: programmable tumour hunters," *Curr Gene Ther* 2:243-54 (2002); Kruyt et al., "Toward a new generation of conditionally replicating adenoviruses: pairing tumor selectivity with maximal oncolysis," *Hum Gene Ther* 13:485-95 (2002)). Among the OVs, the avian paramyxovirus Newcastle disease virus (NDV) is considered to be a very promising oncolytic agent (Reichard et al., "Newcastle disease virus selectively kills human tumor cells," 7 *Surg Res* 52:448-53 (1992); Lorence, et al., "Complete regression of human fibrosarcoma xenografts after local Newcastle disease virus therapy," *Cancer Res* 54:6017-21 (1994)).

The mechanism of viral oncolytic activity involves the induction of multiple caspase-dependent apoptotic pathways, and occurs despite normal IFN responses. Several viruses, including NDV, have been found to induce apoptosis in infected cells (Lam et al., "Apoptosis as a cause of death in chicken embryos inoculated with Newcastle disease virus," *Microb Pathog* 19:169-74 (1995)). It has been shown that the tumoricidal activity of NDV on human monocytes is mediated by TRAIL, and TRAIL expression is independent of virus replication (Washburn et al., "TNF-related apoptosis inducing ligand mediates tumoricidal activity of human monocytes stimulated by Newcastle disease virus," *J Immunol* 170:1814-21 (2003)). However, the exact cellular pathways involved in virus-induced apoptosis and the mechanistic basis of oncolysis are still incompletely understood.

Apoptosis is a multi-step, multi-pathway cell-death program that is inherent in every cell of the body. The apoptotic pathways leading to cell death can generally be divided into two nonexclusive signaling cascades (Igney et al., "Death and anti-death: tumour resistance to apoptosis," *Nat Rev Cancer* 2:277-88 (2002)). In both pathways, cysteine aspartyl-specific proteases (caspases) that cleave cellular substrates are activated, and this leads to the biochemical and morphological changes characteristic of apoptosis. Both the intrinsic and the extrinsic pathways converge on downstream "executioner" caspases, mainly caspase-3, and caspase-6, and -7, which are responsible for the cleavage of structural cytoplasmic and nuclear proteins, with consequent cell collapse and death (Rathmell et al., "The central effectors of cell death in the immune system," *Annu Rev Immunol* 17:781-828 (1999)). Activation of the death receptor and mitochondrion-associated death pathways are not mutually exclusive and these pathways may interact (cross-talk) at many levels.

The mitochondrion apoptotic pathway (intrinsic pathway) initiates with signaling from pro-apoptotic proteins from the Bcl-2 family such as Bax, which trigger the release of cytochrome c in the induction phase. This in turn triggers the release of a second mitochondrion-derived activator of caspase (Smac/DIABLO), as well as apoptosis-inducing factor (AIF), and endonuclease G in the cytosol. (Du et al., "Smac, a mitochondrial protein that promotes cytochrome c-dependent caspase activation by eliminating IAP inhibition," *Cell* 102:33-42 (2000); Verhagen et al., "Identification of DIABLO, a mammalian protein that promotes apoptosis by binding to and antagonizing IAP proteins," *Cell* 102:43-53 (2000)). Cytosolic cytochrome c triggers the formation of a multimeric Apaf-1/cyt c/dATP/procaspase-9 protein complex termed the apoptosome, and the apoptosome then activates caspase-3, which in turns activates the caspase cascade and the degradation phase of apoptosis (Igney et al., supra). Caspase activation and the activity of already active caspases can be inhibited by the inhibitor of apoptosis proteins' (IAPs). Cytochrome c becomes a key regulator in the effector phase because once it is released from the mitochondria the cell is irreversibly committed to death.

The death receptor apoptotic pathway (extrinsic pathway) is initiated by binding of death activators (i.e., FasL, TNF) to their respective transmembrane death receptors (i.e., the tumor necrosis factor receptor (TNF-R) superfamily, which includes CD95 (Fas/APO-1), TNF-RI, DR3, DR4 (TRAIL-R1) and DRS (TRAIL-R2) receptors) (Ichikawa et al., "Tumoricidal activity of a novel anti-human DR5 monoclonal antibody without hepatocyte cytotoxicity," *Nat Med* 7:954-60 (2001); Krammer, "CD95(APO-1/Fas)-mediated apoptosis: live and let die," *Adv Immunol* 71:163-210 (1999); Nagata, "Apoptosis by death factor," *Cell* 88:355-65 (1997)). Apoptosis initiated via death receptors involves the adaptor molecule FADD and subsequent proximity induced activation of caspase-8, an initiator caspase (Ha et al., "A novel family of viral death effector domain-containing molecules that inhibit both CD-95- and tumor necrosis factor receptor-1-induced apoptosis," *J Biol Chem* 272:9621-4 (1997)). The activation of caspase-8, which is similar to caspase-9 in the intrinsic pathway, leads to activation of effector caspases and the degradation phase of apoptosis.

In addition, there is a third pathway that does not use caspases called the Apoptosis-Inducing Factor (AIF) pathway that occurs in neurons. Under an inducing signal, AIF located in the intermembrane space of the mitochondria is released and migrates into the nucleus. Once inside the nucleus it binds to DNA and triggers the destruction of DNA and the degradation phase of apoptosis.

Viruses that induce death receptor-dependent apoptosis include HIV (Miura et al., "Critical contribution of tumor necrosis factor-related apoptosis-inducing ligand (TRAIL) to apoptosis of human CD4+T cells in HIV-1-infected hu-PBL-NOD-SCID mice," *J Exp Med* 193:651-60 (2001)), measles virus (Vidalain et al., "Measles virus induces functional TRAIL production by human dendritic cells," *J Virol* 74:556-9 (2000)), influenza A virus (Nichols et al., "Human lymphocyte apoptosis after exposure to influenza A virus," *J Virol* 75:5921-9 (2001)), reovirus (Clarke et al., "Reovirus-induced apoptosis is mediated by TRAIL," *J Virol* 74:8135-9 (2000)), and lyssa virus (Kassis et al., "Lyssavirus matrix protein induces apoptosis by a TRAIL-dependent mechanism involving caspase-8 activation," *J Virol* 78:6543-55 (2004)). A number of viruses have been found to cause relocalization of proapoptotic mitochondrial proteins into the cytosol. Among these are HIV (Fern et al., "Mitochondrial control of cell death induced by HIV-1-encoded proteins," *Ann N Y Acad Sci* 926:149-64 (2000)), influenza A virus (Chen et al., "A novel influenza A virus mitochondrial protein that induces cell death," *Nat Mod* 7:130612 (2001)), HSV-I (Zhou et al., "Wild-type herpes simplex virus 1 blocks programmed cell death and release of cytochrome c but not the translocation of mitochondrial apoptosis-inducing factor to the nuclei of human embryonic lung fibroblasts," *J Virol* 74:9048-53 (2000)), hepatitis B virus (Terradillos et al., "The hepatitis B: virus X protein abrogates Bcl-2-mediated protection against Fas apoptosis in the liver," *Oncogare* 21:377-86 (2002)), reovirus (Kominsky et al., "Reovirus-induced apoptosis requires both death receptor- and mitochondrial-mediated caspase-dependent pathways of cell death," *Cell Death Differ* 9:926-33 (2002)), and West Nile virus (Parquet et al., "West Nile virus-induced bax-dependent apoptosis.," *FEBS Lett* 500:17-24 (2001)).

Apoptin (viral protein 3—VP3) is a gene product derived from the Chicken Anemia Virus (CAV), which appears to have innate-specific p53-independent, Bcl-2-enhanced pro-apoptotic activity. (Danen-van Oorschot et al., "Apoptin induces apoptosis in human transformed and malignant cells but not in normal cells," *Proc. Natl. Acad. Sci. USA* 94:5843-5847 (1997); Danen-van Oorschot et al., "Importance of nuclear localization of apoptin for tumor-specific induction of apoptosis," *J. Biol. Chem.* 278:27729-27736 (2003); Oro et al., "The tumor specific pro-apoptotic factor apoptin (VP3) from chicken anemia virus," *Curr. Drug Targets* 5:179-190 (2003); Huang et al., "Apoptin, a protein derived from chicken anemia virus, induces p53-independent apoptosis in human osteosarcoma cells," *Cancer Res.* 55:486-489 (1995); Zhuang et al., "Differential sensitivity to Ad5 B1 B-21 kD and Bcl-2 proteins of apoptin-induced versus p53-induced apoptosis," *Carcinogenesis* 16:2939-2944 (1995)). Recent studies with apoptin have shown that it induces G2/M arrest by targeting and inhibiting the anaphase-promoting complex/cyclosome (APC/C). Delivery systems for apoptin include mammalian expression plasmids, HIV-TAT protein transduction domain fusion, autonomous parvovirus and adenoviral vectors.

Newcastle disease virus (NDV), an avian paramyxovirus, is replication-competent in human tumor cells, intrinsically oncolytic, and is currently being tested for use as an oncolytic agent. NDV has been used in the clinic as an experimental oncolytic agent for more than 30 years (Csatary, "Viruses in the treatment of cancer," *Lancet* 2:825 (1971); Lorence et al., "Newcastle disease virus as an antineoplastic agent: induction of tumor necrosis factor-alpha and augmentation of its cytotoxicity," *J Natl Cancer Inst* 80:1305-12 (1988)). NDV is a member of the family Paramyxoviridae and has been assigned to the genus Avulavirus in the subfamily Paramyxovirinae (Mayo, "A summary of taxonomic changes recently approved by ICTV," *Arch Virol* 147.1655-6 (2002)). It carries a serious respiratory and neurological disease in all species of birds, but infections in humans are rare, and any such infections typically result in no more than mild conjunctivitis.

NDV contains a single-stranded, negative-sense, nonsegmented RNA genome. The genomic RNA is 15,186 nucleotides in length (Krishnamurthy, et al., "Nucleotide sequences of the trailer, nucleocapsid protein gene and intergenic regions of Newcastle disease virus strain Beaudette C and completion of the entire genome sequence," *J Gen Virol* 79(10):2419-2424 (1998)). The genomic RNA contains six genes that encode at least seven proteins (Steward et al., "RNA editing in Newcastle disease virus," *J Gen Virol* 74 (Pt 12):2539-47 (1993)). The envelope of NDV contains two glycoproteins, the hemagglutinin-neuraminidase (HN) and fusion (F) proteins. The F glycoprotein mediates fusion of the viral envelope with cellular membranes (Choppin et al., "The role of viral glycoproteins in adsorption, penetration, and pathogenicity of viruses," *Rev Infect Dis* 2:40-61 (1980)). In common with other paramyxoviruses, NDV also produces two additional proteins, V and W, from the P gene by alternative mRNAs that are generated by RNA editing (Griffin, "Neuronal cell death in alphavirus encephalomyclitis," *Curr Top Microbiol Immunol* 289:57-77 (2005); Ichikawa et al., "Tumoricidal activity of a novel anti-human DR5 monoclonal antibody without hepatocyte cytotoxicity," *Nat Med* 7:954-60 (2001); Lana et al., "Characterization of a battery of monoclonal antibodies for differentiation of Newcastle disease virus and pigeon paramyxovirus-1 strains.," *Avian Dis* 32:273-81(1988); Rathmell et al., "The central effectors of cell death in the immune system," *Ann Rev Immunol* 17:781-828 (1999); Sangfelt et al., "Induction of apoptosis and inhibition of cell growth are independent responses to interferon-alpha in hematopoietic cell lines," *Cell Growth Differ* 8:343-52 (1997)).

NDV has been shown to be tumor-selective in replication, and cytolytic in infected tumor cells, while normal human cells are unaffected (Reichard et al., "Newcastle disease virus selectively kills human tumor cells," 7 *Surg Res* 52:448-53 (1992)). One genetic defect that is common among tumor cells is diminished IFN "responsiveness" (Stojdl et al., "Exploiting tumor-specific defects in the interferon pathway with a previously unknown oncolytic virus," *Nat Mod* 6:821-5 (2003)). NDV is a potent IFN inducer, and the tumor selectivity is therefore considered to be due to defective interferon response in tumor cells (Reichard et al., supra). Also, activating mutations in ras genes have been found in >30% of cancers, and constitutive ras pathway signaling brought about by oncogenic changes in upstream and downstream elements arises in an even greater proportion of human tumors. It has been demonstrated that some naturally occurring strains of NDV replicate well in tumors with ras gene activation, and are oncolytic in those tumors (Reichard et al., supra).

NDV strains are known to evoke cellular apoptosis (Lam et al., "Apoptosis as a cause of death in chicken embryos inoculated with Newcastle disease virus," *Microb Pathog* 19:169-74 (1995); Washburn et al., "TNF-related apoptosis-inducing ligand mediates tumoricidal activity of human monocytes stimulated by Newcastle disease virus," *J Immunol* 170:1814-21 (2003)). It has been suggested that TNF-$\alpha$ might be involved in the tumoricidal activity of NDV-activated murine macrophages and human peripheral blood mononuclear cells (Lorence et al., "Newcastle disease virus as an antineoplastic agent: induction of tumor necrosis factor-alpha and augmentation of its cytotoxicity," *J Natl Cancer Inst* 80:1305-12 (1998); Washburn et al., supra). It is also claimed that the cell-to-cell contact killing of tumor cells by NDV-stimulated macrophages is mediated by TRAIL (Washburn et al., supra). Most of these studies tested the apoptotic response of NDV-activated human cells on human tumor cells. On the other hand, direct infection studies with NDV strain MTH/68 in PC12 rat phaeochromocytoma cells indicated that major mitogen-activated protein kinase pathways (including the stress inducible c-Jun N-terminal kinase pathway and p38 pathway) or mechanisms regulated by reactive oxygen species have no role in virus-induced apoptosic cell death (Fabian et al., "Induction of apoptosis by a Newcastle disease virus vaccine (MTH-68/H) in PC12 rat phaeochromocytoma cells," *Anticancer Res* 21:125-35 (2001); Stojdl et al., "Exploiting tumor-specific defects in the interferon pathway with a previously unknown oncolytic virus," *Nat Mod* 6:821-5 (2000)).

U.S. Pat. No. 6,896,881 discloses compositions and methods for treating a patient having a tumor, in order to reduce tumor size, by administering replication-competent Paramyxoviridae virus comprising two or more of a) a nucleic acid sequence encoding a heterologous polypeptide that is detectable in a biological fluid of the patient, where detection of the heterologous polypeptide is indicative of Paramyxoviridae virus growth in the patient and reduction in tumor size; b) a recombinant F protein, H protein, or M protein of Paramyxoviridae virus that increases fusogenicity of virus with cells; c) a nucleic acid sequence encoding a cytokine; and d) a Paramyxoviridae virus that is specific for cells of the tumor. The patent provides examples based only on the use of a recombinant measles virus.

U.S. Pat. No. 6,428,968 discloses compositions and methods for killing tumor cells in a patient, including administering both a chemotherapeutic agent and an oncolytic virus (other than an adenovirus) to a patient who has tumor cells. The agent and virus exhibit oncolytic activities that are at least additive, and that may be synergetic. The oncolytic virus may be a herpes simplex virus (type 1 or 2), a vaccinia virus, a vesicular stomatitis virus, or a Newcastle disease virus. The compositions and kits comprise a chemotherapeutic agent and an oncolytic virus (other than an adenovirus), either in admixture or separately.

U.S. Published Application No. 2004/0131595 discloses use of a negative-stranded RNA virus to treat a mammalian subject having a carcinoid tumor. The virus may be a Paramyxovirus, and may be a Newcastle disease virus.

U.S. Published Application No. 2003/0165465 discloses viruses that are able to replicate and kill neoplastic cells that have a deficiency in the IFN-mediated antiviral response. Such viruses may be used in treating neoplastic diseases, including cancer and large tumors. RNA and DNA viruses, including Paramyxoviruses, such as Newcastle disease virus, are stated to be useful in this regard.

U.S. Published Application No. 2003/0040498 discloses oncolytic activity of RNA-based vectors derived from poliovirus, termed replicons, which are genetically incapable of producing infectious virus. The replicons cytopathic in vitro for human tumor cells originating from brain, breast, lung, ovaries and skin (melanoma). Injection of replicons into established xenograft flank tumors in scid mice resulted in oncolytic activity and extended survival. Inoculation of replicons into established intracranial xenografts tumors in scid mice resulted in tumor infection and extended survival. Histological analysis was conducted in order to demonstrate that replicons infected tumor cells at the site of inoculation, and then diffused to infect tumor cells which had metastasized from the initial site of implantation.

With the availability of a reverse genetics system for NDV, it is now possible to manipulate the genome of NDV, engineer additional genes, and retarget the virus to specific receptors (Krishnamurthy et al., "Recovery of a virulent strain of Newcastle disease virus from cloned cDNA: expression of a foreign gene results in growth retardation and attenuation," *Virology* 278:168-82 (2000); Huang et al., "High-level expression of a foreign gene from the most 3'-proximal locus of a recombinant Newcastle disease virus," *J Gen Virol* 82:1729-36 (2001); Bian et al., "Tumor-targeted gene transfer in vivo via recombinant Newcastle disease virus modified by a bispecific fusion protein," *Int J Oncol* 27:377-84 (2005)). However, there is still a need in the art for compositions comprising oncolytic viruses, such as NDV, and methods of using them to treat cancer in patient suffering therefrom. There is particularly a need in the art for genetically-engineered oncolytic viruses, such as NDV, which incorporate additional therapeutic transgenes into their genomes. Such genetically-engineered oncolytic viruses may be used in accordance with methods for providing targeted delivery of the oncolytic viruses to specific sites and/or specific tumors within the body of a patient.

SUMMARY OF THE INVENTION

Among other things, the present invention provides recombinant oncolytic APMV, such as NDV, compositions comprising them, and methods of using them to treat cancer in patient suffering therefrom. The present invention also provides genetically-engineered oncolytic APMV, such as NDV, which incorporate additional therapeutic transgenes into their genomes. Such genetically-engineered oncolytic viruses may be used in accordance with methods for providing delivery of the oncolytic viruses to specific tumors within the body of a patient. The present invention further includes methods of identifying recombinant APMV, such as NDV, which are useful as oncolytic agents.

Thus, one embodiment of the invention is directed to a recombinant Newcastle disease virus (rNDV) strain, wherein said rNDV has been genetically-modified to include one or more transgenes that induce apoptosis in one or more tumor cell lines, selected from the group consisting of transgenes that induce production of pro-apoptotic proteins, transgenes that activate tumor suppressing genes; and transgenes that activate pro-apoptotic proteins.

Another embodiment of the invention is directed to an oncolytic composition including one or more of these recombinant NDV strains and optionally one or more pharmaceutically-acceptable excipients.

Another embodiment of the invention is directed to a method for lysing tumor cells, including providing an oncolytically-effective amount of one or more of the rNDV strains directly to said tumor cells. In accordance with one aspect, the tumor cells may be lysed in vitro. In accordance with another aspect, the one or more rNDV strains may be administered directly into a tumor in a patient.

Another embodiment of the invention is directed to a method for treating cancer in a patient suffering therefrom, including the step of administering directly into a tumor present in said patient a therapeutically-effective amount of a composition comprising one or more of the rNDV strains.

Yet another embodiment of the invention is directed to a method for identifying an rNDV strain that is oncolytically-effective against a tumor cell line, including the steps of isolating a tumor cell line from a tumor; infecting said tumor cell line with an rNDV strain; and detecting that said rNDV has induced apoptosis in said tumor cell line by conducing an assay for one or more metabolic indicators of cell death.

Other novel features and advantages of the present invention will become apparent to those skilled in the art upon examination of the following or upon learning by practice of the invention.

BRIEF DESCRIPTION OF THE DRAWINGS

For a more complete understanding of the present invention, the needs satisfied thereby, and the objects, features, and advantages thereof, reference now is made to the following description taken in connection with the accompanying drawings.

Figure 2:
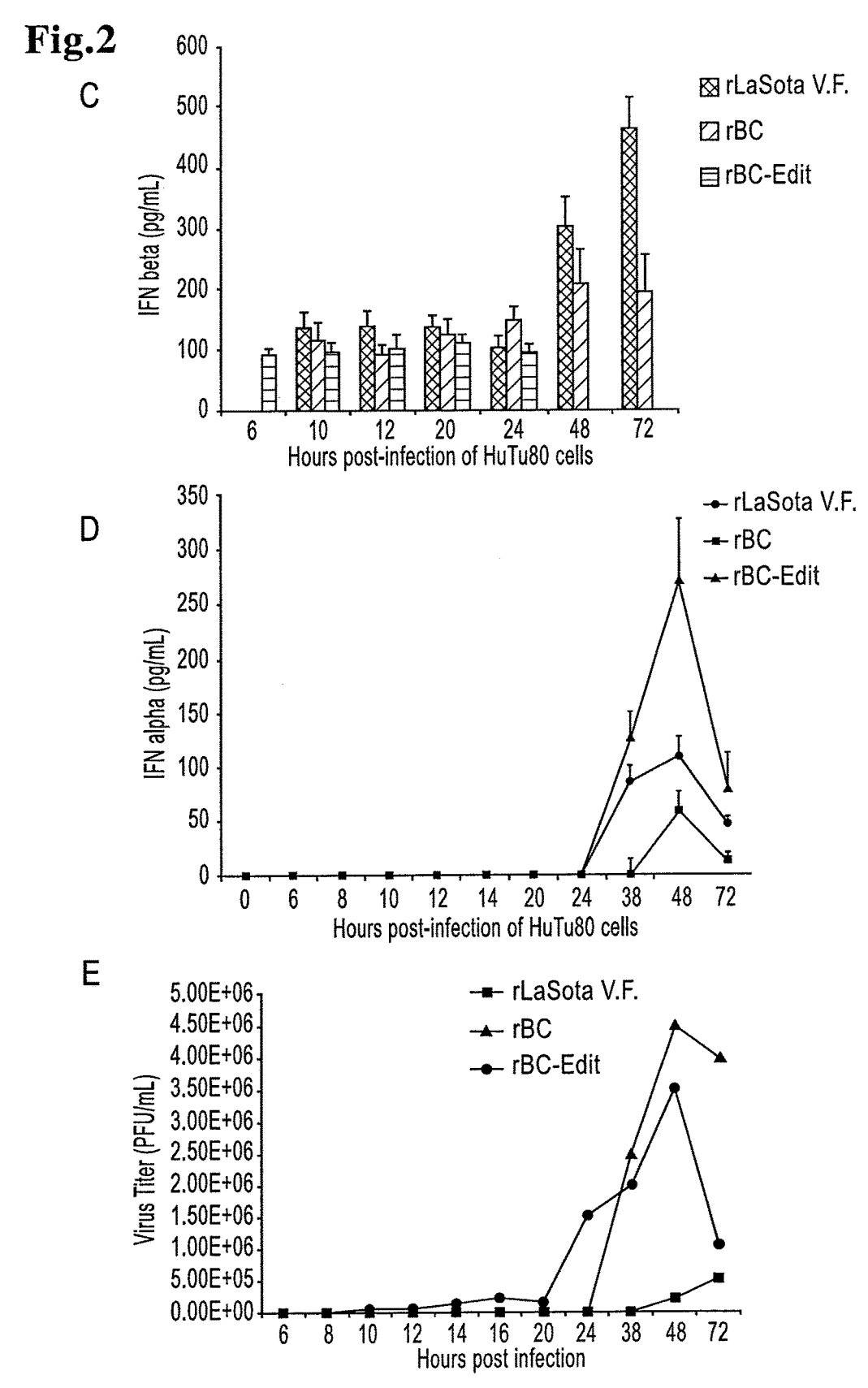

FIG. 2. Interferon induction and virus replication by rNDV in normal and human tumor cells. DF1 chicken embryo fibroblast cells, normal and human tumor cells were either mock infected or infected with rLaSota V.F., rBC, or rBC-Edit strains of NDV at 10 MOI without IFN-pretreatment. Culture supernatants at indicated time points were tested for IFN-β and IFN-α by human IFN ELISA and virus content from infected HuTu 80 cells was assessed by a plaque assay on DF1 cells. IFN-β production in rNDV infected cells at 48 h post-infection (A); IFN-α production at 48 h post-infection (B); time course-analysis of IFN-β production in HuTu 80 cells (C); time course-analysis of IFN-α production in HuTu 80 cells (D). Multi-cycle virus replication of rNDV in HuTu 80 cells (E). Results represent mean values+SEM from two independent experiments.

FIG. 13. Interferon sensitivity of recombinant NDV.

FIG. 14. Interferon-beta production in tumor cells by rNDV.

FIG. 15. Time course of interferon-beta production in HuTu80 tumor cells.

FIG. 16. Interferon-alpha production by rNDV in tumor cells.

FIG. 17. Time course of interferon-alpha production in HuTu80 cells by rNDV.

FIG. 18. RANTES induction by recombinant NDV.

FIG. 19. Induction of IP-10 by rNDV in tumor cells.

FIG. 20. Expression of interferon regulatory factors (IRFs) in DF1 chicken embryo fibroblast cells. Cell lysates were prepared from rNDV infected cells (10 MOI) and electrophoresed on 4-20% SDS-PAGE gels and transferred to nitrocellulose membrane and probed with anti-IRF-3 antibodies (Santa Cruz Biotech). IRF-3 expression in DF1 (A); IRF-7 expression (B); IRF-3 in MCF-7 cells (C); and IRF-7 in MCF-7 cells (D).

FIG. 21. Expression of STAT1-alpha in HuTu80 cells after infection with rNDV.

Figure 22:
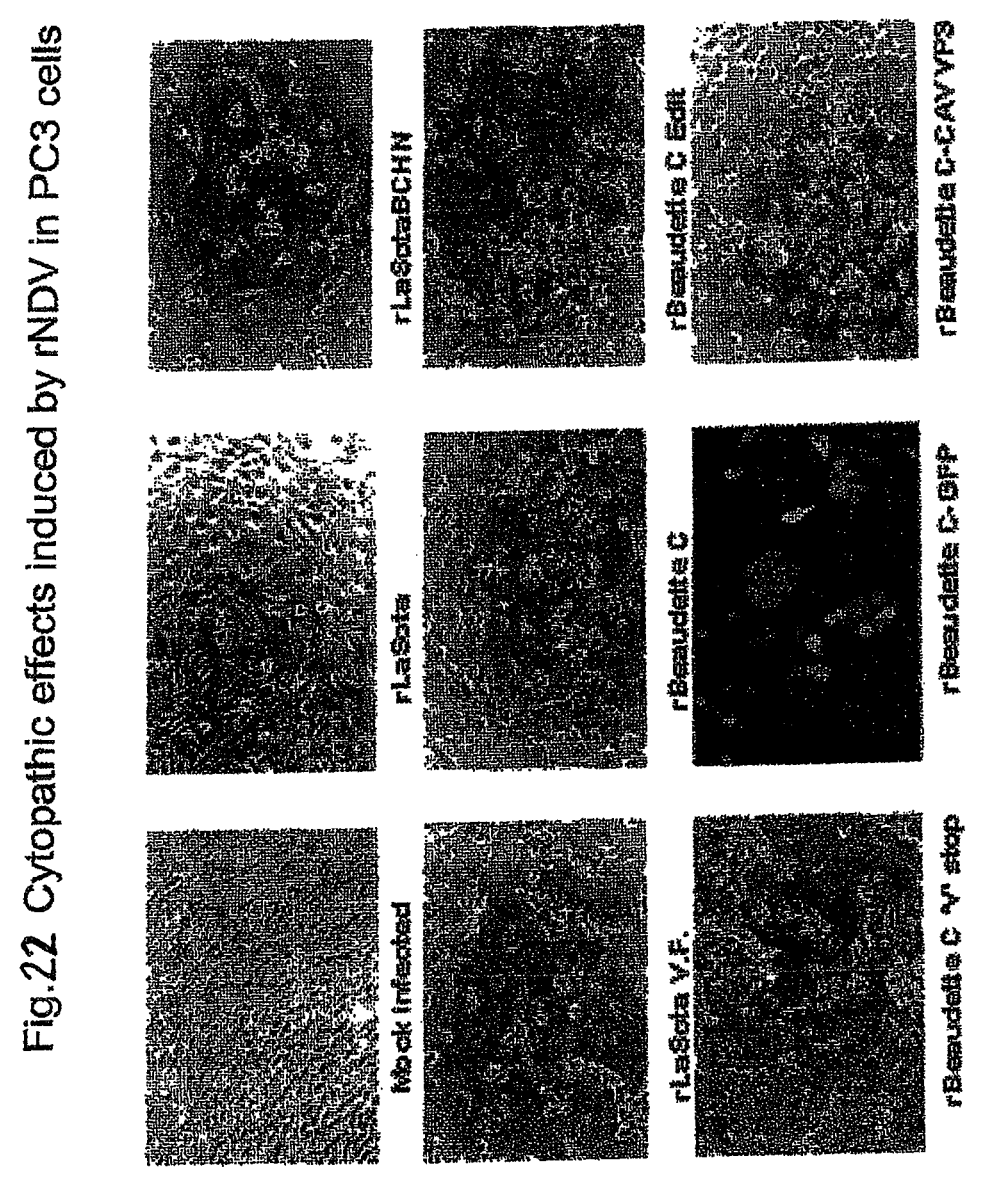

FIG. 22. Cytopathic effects induced by rNDV in PC3 cells.

FIG. 23. Interferon-beta production in normal SV-HUC1 cells by rNDV.

Figure 24:
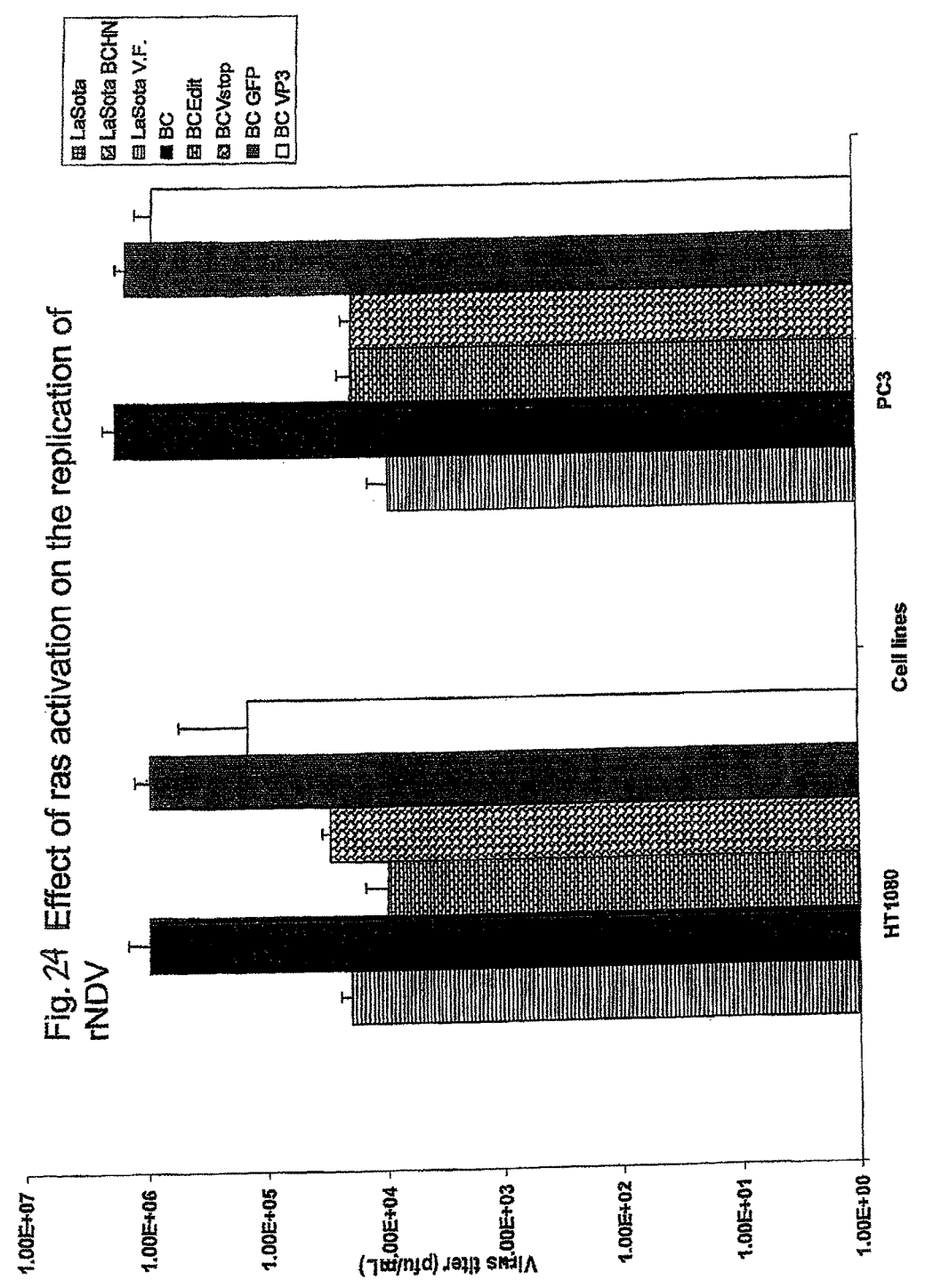

FIG. 24. Effect of ras activation on the replication of rNDV.

Figure 25:
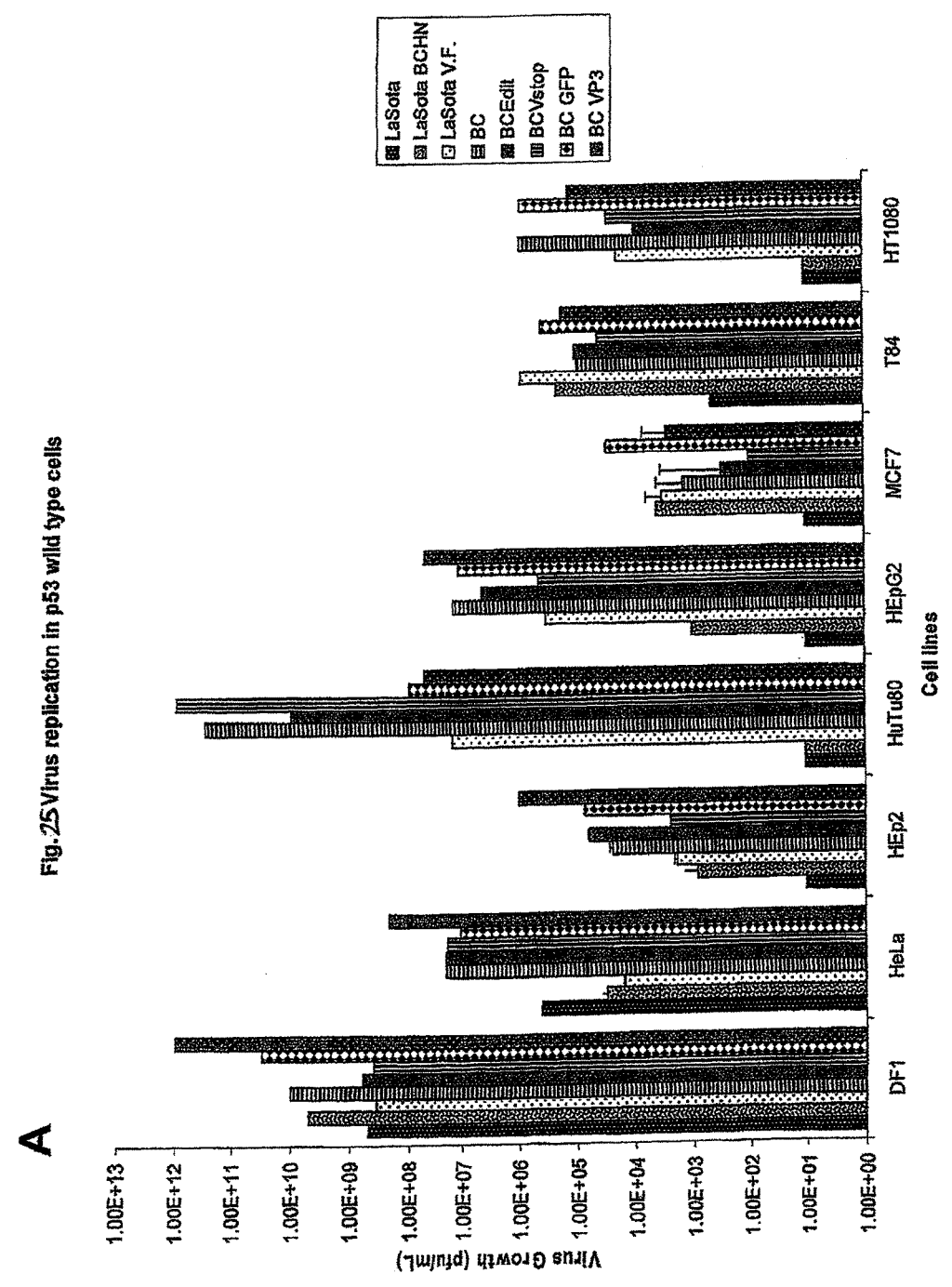

FIG. 25. Virus replication in p53 wild type cells (A). Virus replication in p53 mutant cell lines (B). Multistep growth curve in HuTu80 cells (C).

FIG. 26. Annexin V staining in rNDV infected cells 6 hours post-infection (PI).

FIG. 27. Apoptotic DNA laddering in tumor cell lines after infection with rNDV in HuTu80 cells.

FIG. 28. TNF-alpha induction by rNDV in HuTu80 cells.

FIG. 29. TNF-alpha induction by rNDV in normal human cells (SV-HUC1).

FIG. 30. Soluble TRAIL induced by rNDV in tumor cell lines.

FIG. 31. Surface expression of TRAIL in rNDV-infected HuTu80 cells.

FIG. 32. Caspace-8 induction by rNDV in various tumor cell lines.

FIG. 33. Kinetics of caspase-8 induction by rNDV in HuTu80 cells.

FIG. 35. Caspase-9 activation in tumor cells.

FIG. 36. Kinetics of Caspase-9 activation in HuTu80 cells (A); and SHSY5Y neuroblastoma cells (B).

FIG. 37. Caspase-3 activation in tumor cells by rNDV.

FIG. 38. Kinetics of Caspase-3 activation in HuTu80 cells (A); and SHSY5Y neuroblastoma cells (B).

DETAILED DESCRIPTION OF PREFERRED EMBODIMENTS

Figure 1:
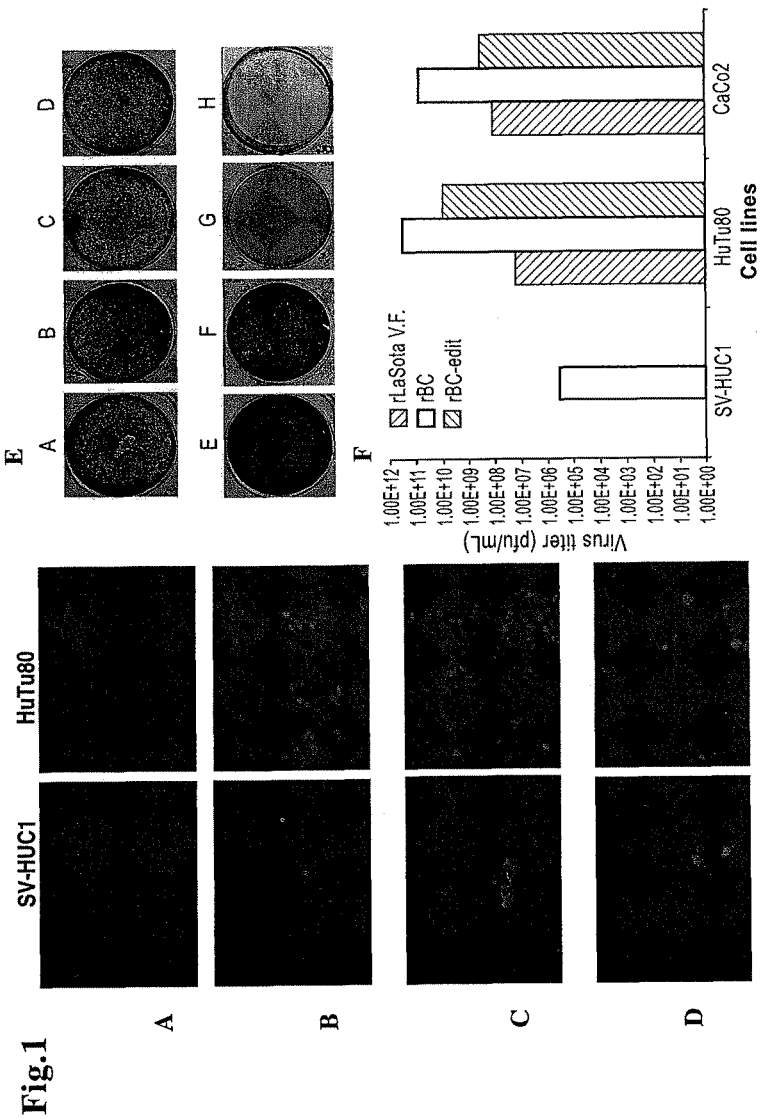
FIG. 1. Virus replication and spread of NDV differ in normal human epithelial cells and HuTu 80 tumor cells. SV-HUC-1, normal, immortalized human uroepithelial cells and HuTu 80 intestinal epithelial tumor cells were infected with rBC-EGFP virus at 0.01 MOI. Panels A-D: Right panels indicate SV-HUC-1 cells and left panels indicate HuTu 80 cells. Mock-infected cells (A), expression of EGFP in few virus-infected normal cells against extensive EGFP fluorescence in virus-infected HuTu80 cells by 12 h post-infection (B), absence of virus spread and replication in normal cells against extensive EGFP and virus spread in tumor cells by 24 h post-infection (C), and expression of EGFP in few cells with absence of viral spread in normal human cells at 48 h while complete destruction of monolayer with clumps of dead cells expressing EGFP in HuTu 80 tumor cells (D) are seen. Panel E: The mock and rNDV infected cells in 6-well plates were stained with 1% crystal violet at 48 h post-infection. Top panel represent SV-HUC-1 cells and bottom panels represent HuTu 80 cells mock infected or infected with 0.01 MOI of rLaSota V.F., rBC, and rBC-edit viruses, respectively from right to left. In contrast to normal cells, there was a complete destruction of monolayer of tumor cells with detachment from the culture dish, seen as unstained areas. Panel F: Multi-cycle replication of rNDV was assessed by infecting cells at 0.01 MOI. Culture supernatants were assayed for virus content by a plaque assay on DF1 cells at 48 h post-infection. Results represent mean values+SEM from two independent experiments. For comparison, virus replication in IFN-responsive HuTu80 and IFN-resistant CaCo2 cells is shown from 0.01 MOI infection.
Figure 3:
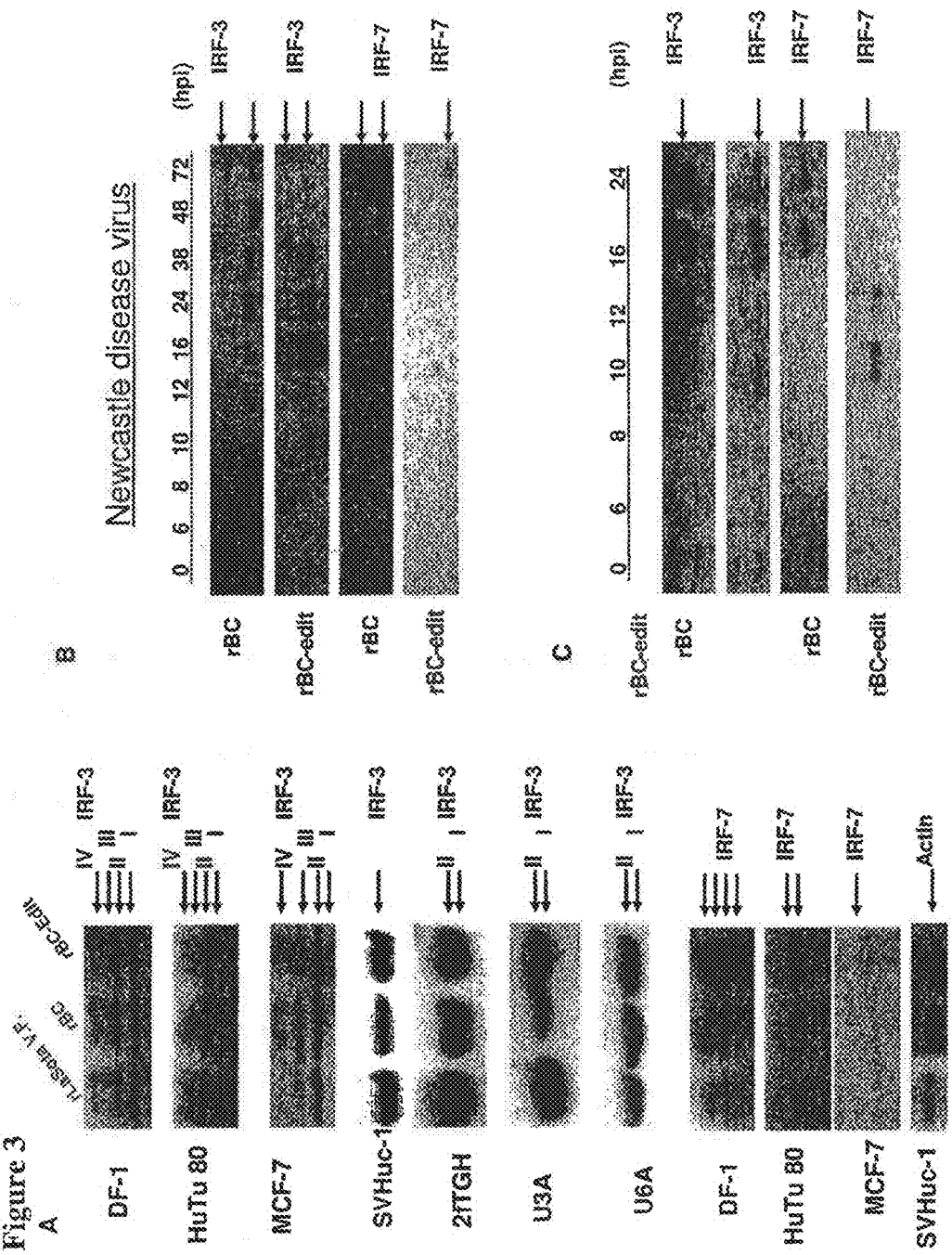
FIG. 3. NDV exploits tumor specific defects in IFN pathway for exerting its oncolytic effect. DF1 chicken embryo fibroblast cells or human tumor cells were either mock infected or infected with rLaSota V.F., rBC, or rBC-Edit strains of NDV at 10 MOI. Total cell lysates (20 µg) were subjected to SDS-PAGE (4-20%) electrophoresis and transferred to nitrocellulose membrane and probed with anti-IRF-3 and anti-IRF-7 antibodies at 48 h post-infection by immunoblotting. IRF-3 hyperphosphorylation in DF-1, MCF-7 breast cancer cells, HT1080 human fibrosarcoma, SV-HUC-1, 2fTGH, U3A, and U6A cells and IRF-7 expression in DF1, HuTu 80, and MCF-7 cells are shown. IRF-7 expression was not detectable in 2fTGH, U3A, and U6A cells (A). Time-course analysis of IRF-3 hyperphosphorylation and IRF-7 expression in HuTu 80 cells following rNDV infection. Cytoplasmic extracts were probed with anti-IRF-3 and anti-IRF-7 antibodies (B). Nuclear extracts were probed with anti-IRF-3 and anti-IRF-7 antibodies (C). hpi: hours post-infection. Blots were reprobed with actin to ensure equal loading.
Figure 4:
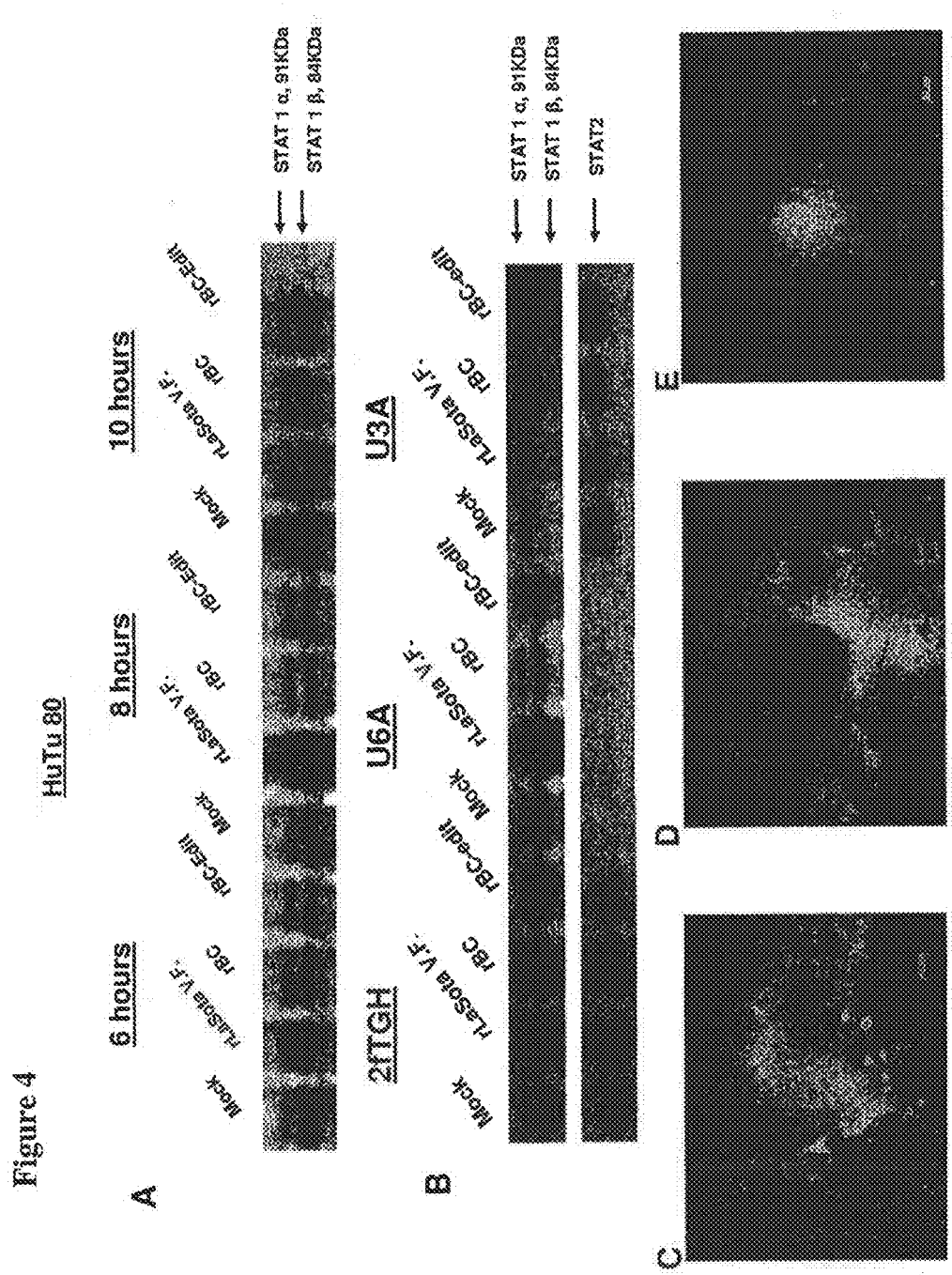
FIG. 4. STAT expression in human tumor cells. HuTu 80 human intestinal epithelial cells were either mock infected or infected with rLaSota V.F., rBC, or rBC-Edit strains of NDV at 10 MOI. Total cell lysates were assayed for STAT1 at indicated times post-infection by immunoblotting (A). 2fTGH, U3A, and U6A human fibrosarcoma cells were either mock infected or infected with rLaSota V.F., rBC, or rBC-Edit strains of NDV at 10 MOI. Total cell lysates were assayed for STAT1 and STAT2 at 48 h post-infection by immunoblotting (B). Virus replication indicated by EGFP expression in mutant ras-activated and wild type ras tumor cells. 2fTGH cells, active p21 ras (C), U3A cells, active p21 ras (D), U6A cells, active p21 ras (E).
Figure 5:
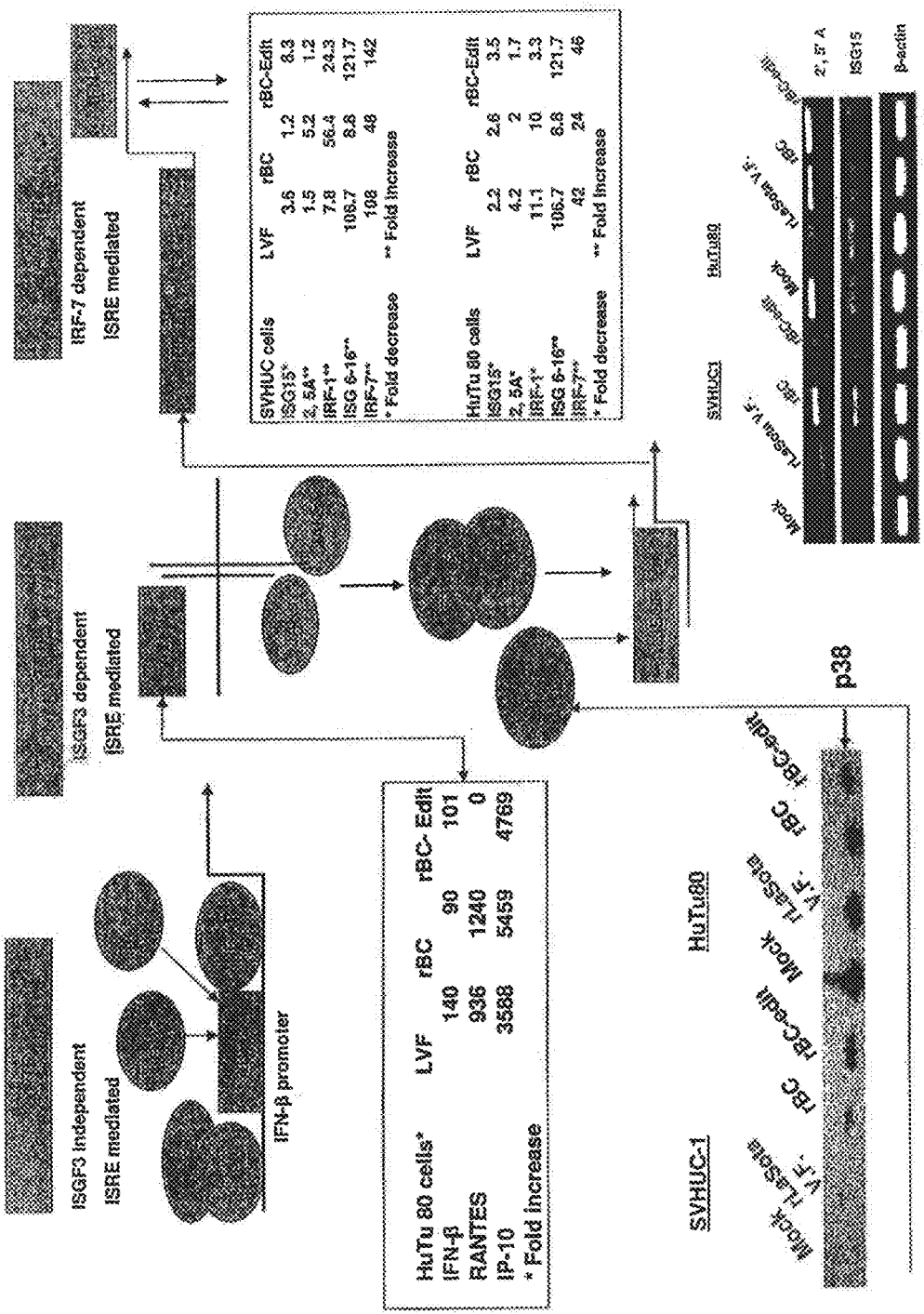
FIG. 5. IFN-α responsive genes induced after rNDV infection in normal and tumor cells. The failure of secondary and tertiary transcriptional responses to NDV aids in tumor selectivity and oncolysis. Primary response to viral infection is mediated by IRF-3 leading to stimulation of the IFN-β promoter. IFN-β is then translated and secreted to stimulate in an autocrine fashion, JAK/STAT signaling to form ISGF3 complexes in the nucleus, which mediates the induction of the secondary transcriptional responses. Without the consequent expression of IRF-7 in cells infected with rNDV, the tertiary transcriptional wave, which includes almost all IFN-α genes, can not take place. In the absence of IFN-α and IFN-α responsive antiviral genes, virus replication is enabled in tumor cells. In normal human cells, the transcriptional events proceed unhampered resulting in a robust antiviral state preventing virus replication. IFN-α responsive antiviral genes were detected by RT-PCR of cell lysates infected with rNDV at 48 h post-infection. Fold-increase of different antiviral mediators such as ISG15, 2', 5' A, IRF-1 and ISG 6-16 mRNA levels compared to mock infected cells is shown. SV-HUC1 normal human cells (A), HuTu 80 tumor cells. Values represent average fold increase over mock infected cells from two independent experiments. RT-PCR products of 2, 5 A and ISG 15 analyzed in 2% agarose gels are shown along with β-actin for comparison. p38 MAPK expression in mock-infected or rNDV-infected normal and tumor cells.
Figure 6:
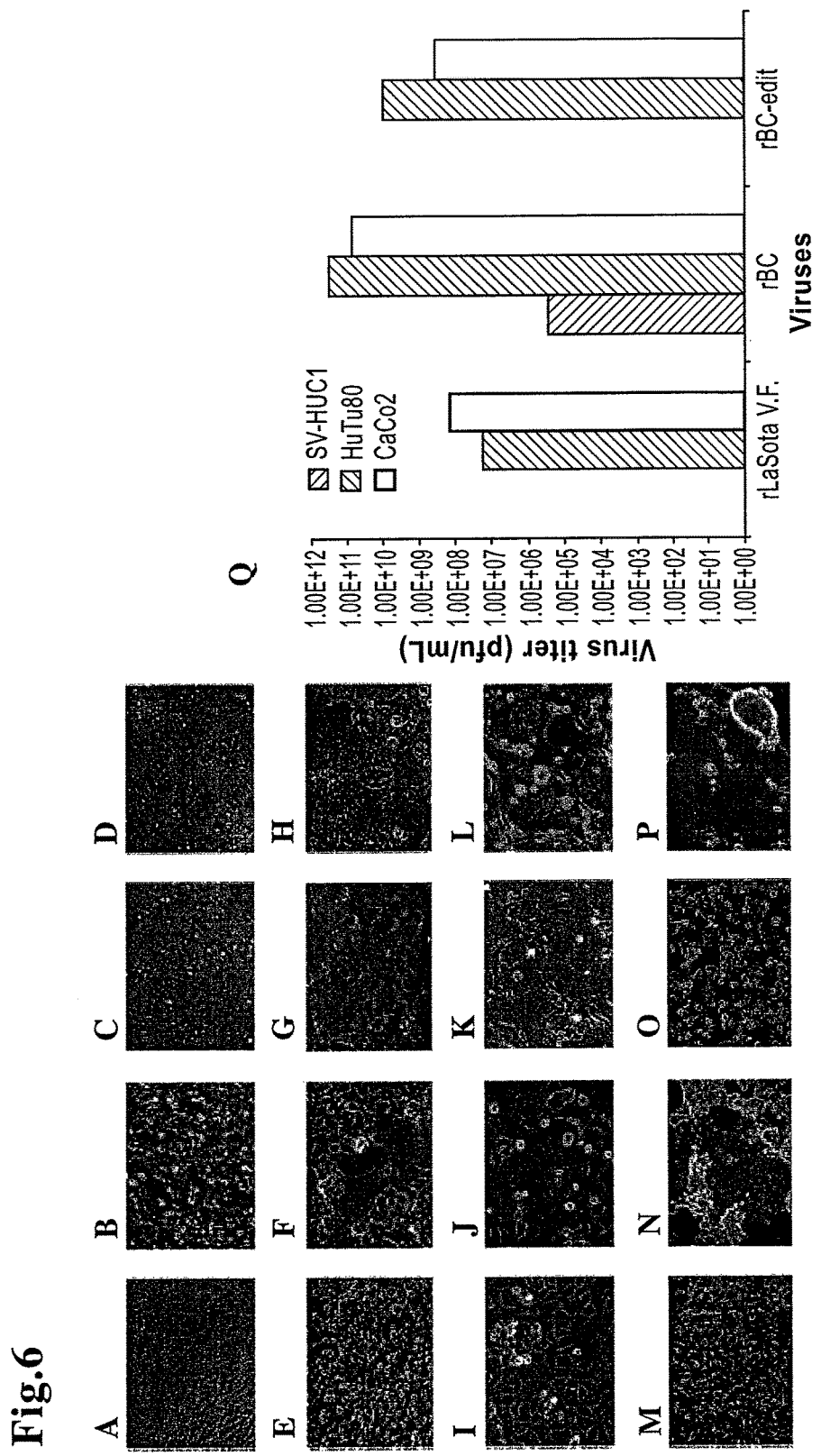
FIG. 6. NDV is cytolytic to human tumor cells and noncytolytic in normal human cells. Shown are CPE induced by rNDV in chicken embryo fibroblast and human tumor cells. DF1 chicken embryo fibroblast cells and human tumor cell lines were either mock infected or infected with rLaSota V.F., rBC, or rBC-Edit strains of NDV at an MOI of 0.01. CPE in the form of cell fusion, syncytium formation, rounding, and destruction of the monolayer in different cells are shown. (A and B) Mock-infected and rBC-Edit-infected HEpG2 cells. (C and D) Mock-infected and rBC-Edit-infected HT1080 cells. (E and F) Mock-infected and rBC- Edit-infected PC3 prostate cancer cells. (G and H) Mock-infected and rBC-Edit-infected CaCo2 colon cancer cells. (I and J) Mock-infected and rBC-Edit-infected HuTu80 intestinal epithelial cells. (K and L) Mock-infected and rBC-Edit-infected DF1 chicken embryo fibroblast cells. (M and N) Mock-infected and rBC-Edit-infected 2frGH human fibrosarcoma cells. (O and P) Mock-infected and rBC-Edit-infected U3A human fibrosarcoma cells. Magnification, ×40. (Q) SV-HUC1 uroepithelial cells were either mock infected or infected with rLaSota V.F., rBC, or rBC-Edit strains of NDV at MOIs of 0.01, 1.0, or 10. Culture supernatants were assayed for virus content by a plaque assay in DF1 cells at 48 h postinfection, and results of virus titer determination at an MOI of 0.01 were compared with those for viruses assayed under similar conditions in HuTu80 and CaCo2 cells. Results represent mean values+SEM from two independent experiments.
Figure 7:
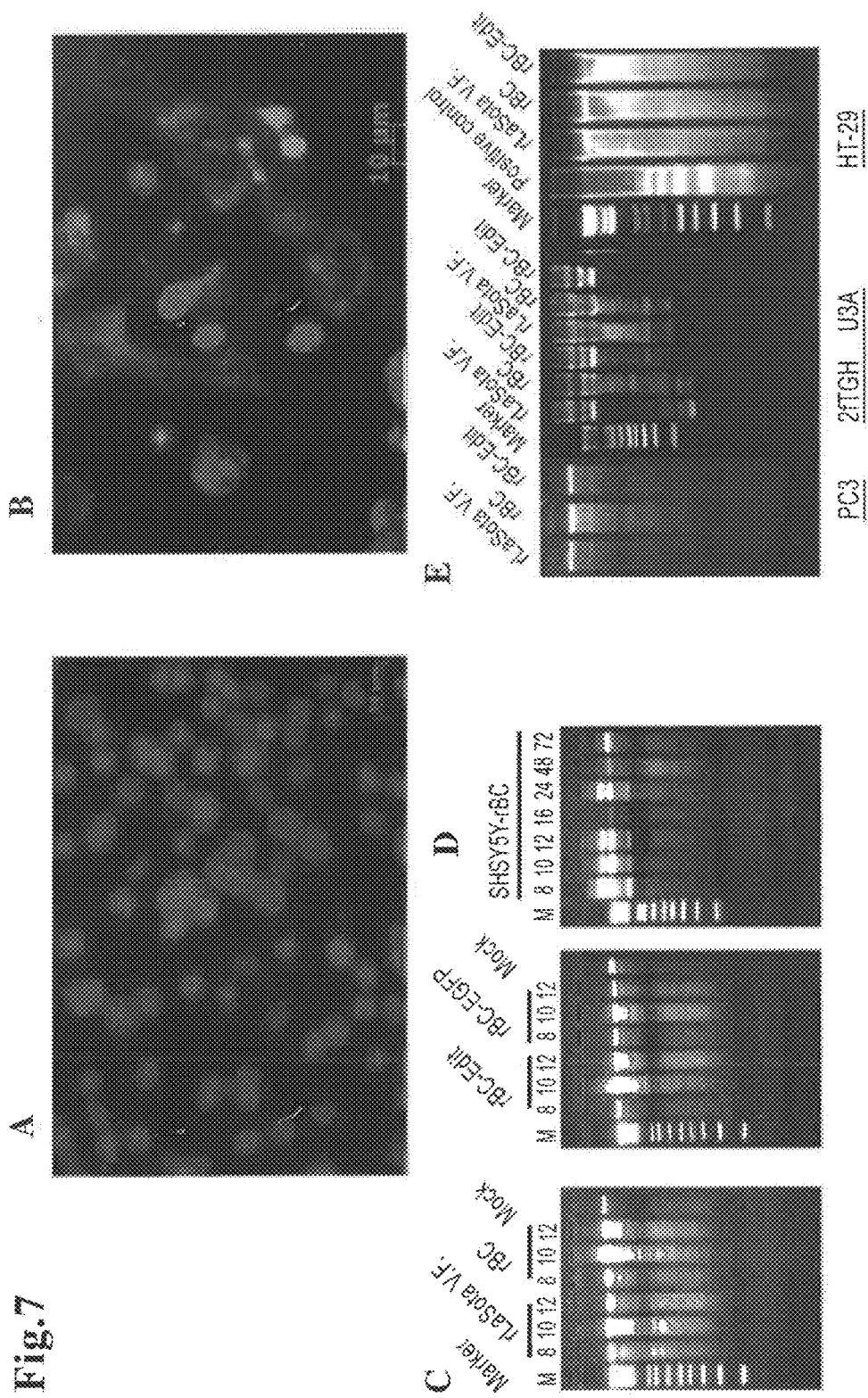
FIG. 7. Morphological features of apoptosis in rNDV-infected human tumor cells. Cells were either mock infected or infected with rLaSota V.F., rBC, rBC-Edit, or rBC-EGFP strains of NDV at an MOI of 0.01. At 6 and 14 h postinfection, apoptotic cell death was visualized by staining the infected cells with DAPI (1 μg/ml). (A) Condensation of chromatin and nuclear fragmentation of rNDV-infected HuTu80 cells. (B) Fluorescein isothiocyanate-annexin V (10 mg/ml) staining of NDV-infected HuTu80 cells. (B) Phosphatidyl serine externalization to the outer leaflet of the infected cell membrane is evident by green fluorescence of the cell membrane. (C) DNA laddering of infected cells was examined by using an apoptotic DNA laddering kit (Roche) per the manufacturer's instructions. Intranucleosomal DNA fragmentation is evident as a laddering pattern of the cellular DNA in rNDV-infected HuTu80 cells at 8, 10, and 12 h postinfection. (D) DNA laddering of SH-SY5Y neuroblastoma cells at 8, 10, and 12 h postinfection. (E) DNA laddering of rNDV-infected PC3, 2fTGH, U3A, and HT29 cells at 12 h postinfection.
Figure 8:
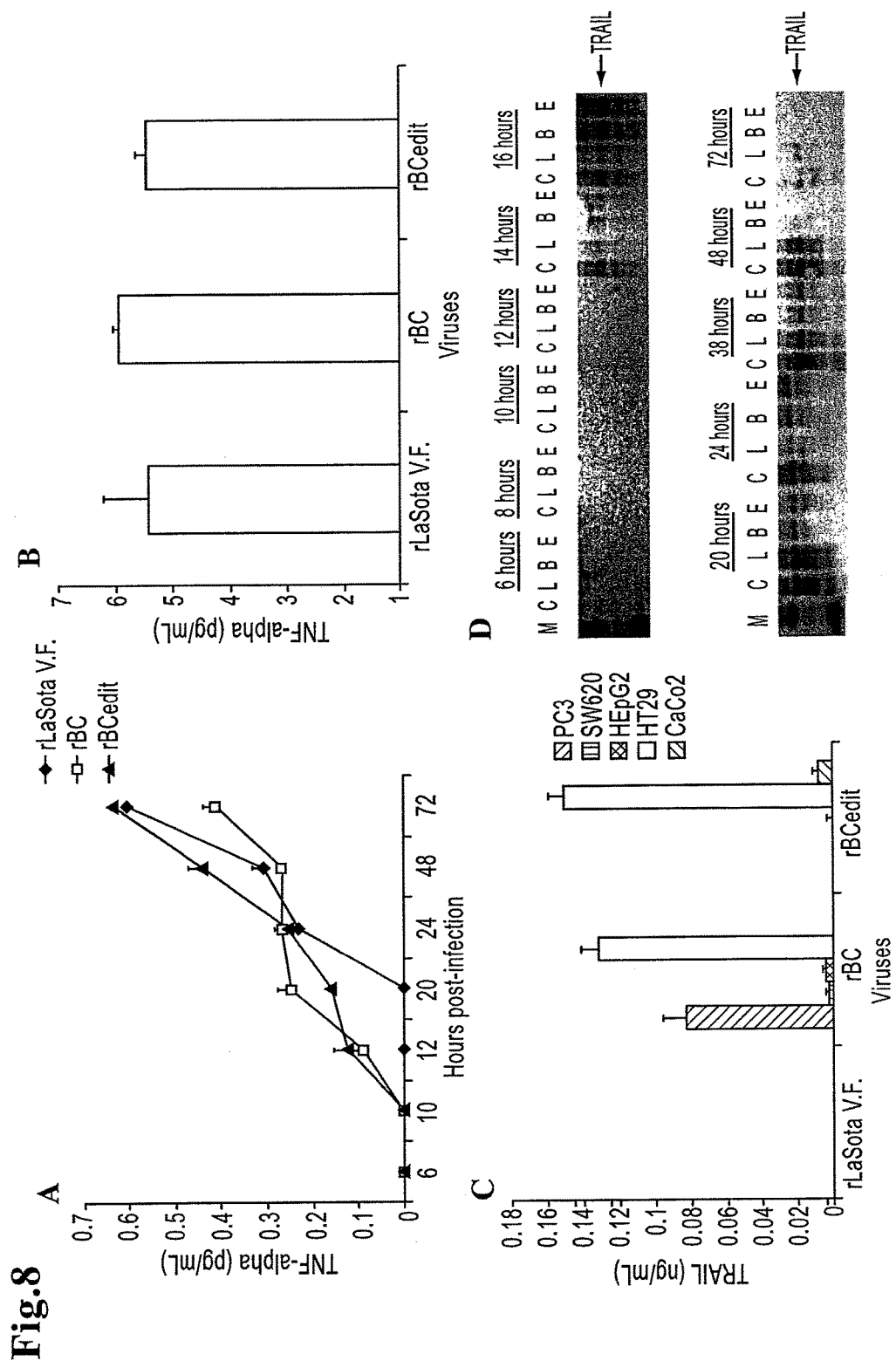
FIG. 8. Apoptotic signaling in rNDV-infected cells. DF1, SV-HUC1, and human tumor cells were either mock infected or infected with rLaSota V.F., rBC, or rBGEdit strains of NDV at an MOI of 0.01. Culture supernatants were assayed by ELISA for TNF-a production at 48 h postinfection in HuTu80 cells (A) and SV-HUC1 cells (B). Soluble TRAIL expression was assayed by ELISA in various tumor cells at 48 h postinfection (C), and surface expression of TRAIL was examined in HuTu80 cells by immunoblotting with anti-TRAIL antibody at the indicated times postinfection (D). C, mock infected; L, rLaSota V.F. infected; B, rBC infected; E, rBGEdit infected; M, molecular weight marker. ELISA results represent mean values+SEM from two independent experiments.
Figure 9:
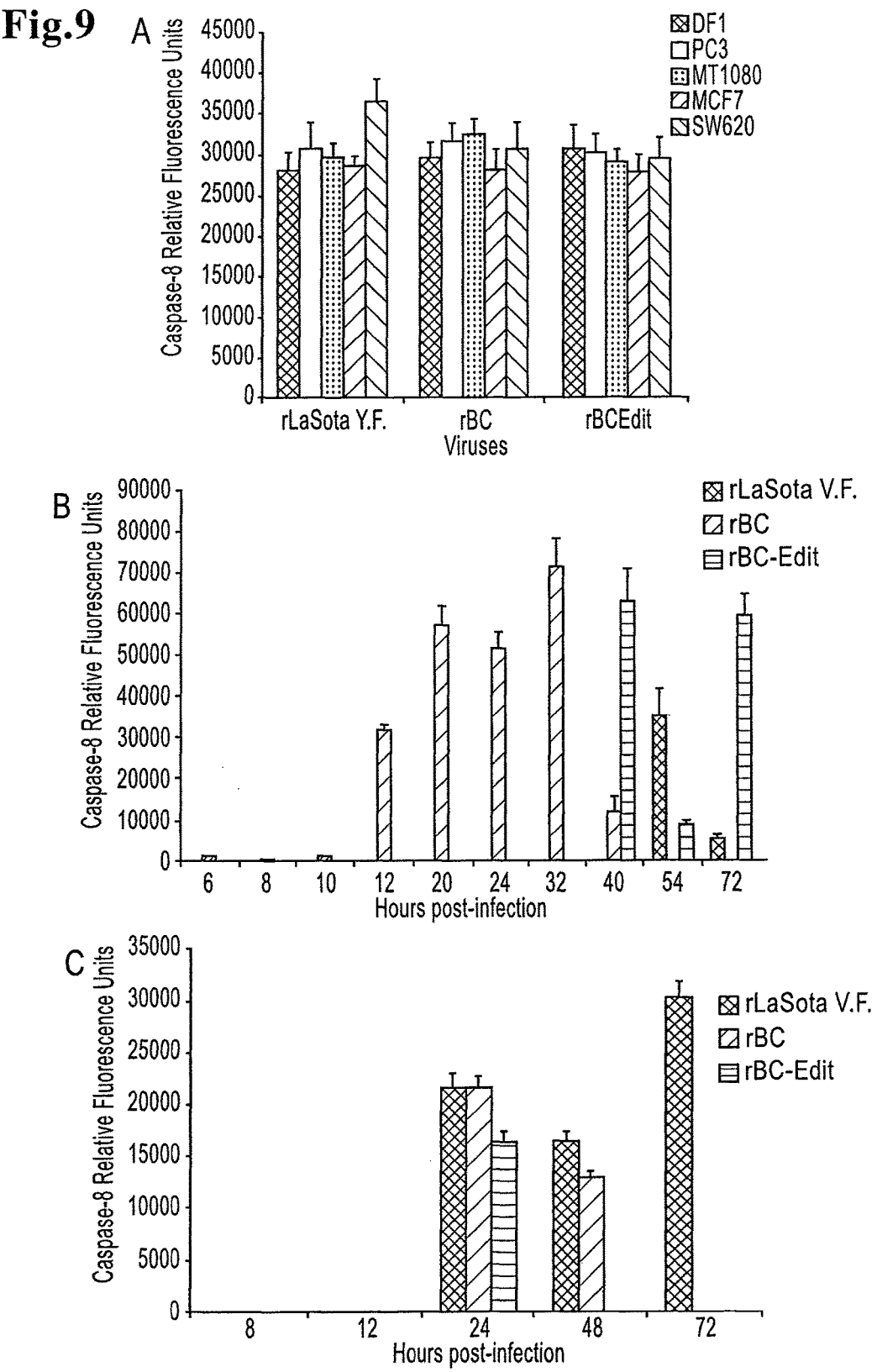
FIG. 9. Caspase-8 expression in NDV-induced apoptosis of tumor cells. DF1 and various human tumor cells were either mock infected or infected with rLaSota V.F., rBC, or rBC-Edit strains of NDV at an MOI of 0.01. Culture supernatants were assayed by ELISA for caspase-8 production at 48 h postinfection. The relative fluorescence units over mock-infected controls are shown for DF1 and a few representative human tumor cells for caspase-8 (A). (B) Kinetics of caspase-8 induction in HuTu80 cells. (C) Caspase-8 production in caspase-8-methylated SH-SY5Y neuroblastoma cells. Results represent mean values+SEM from two independent experiments.
Figure 10:
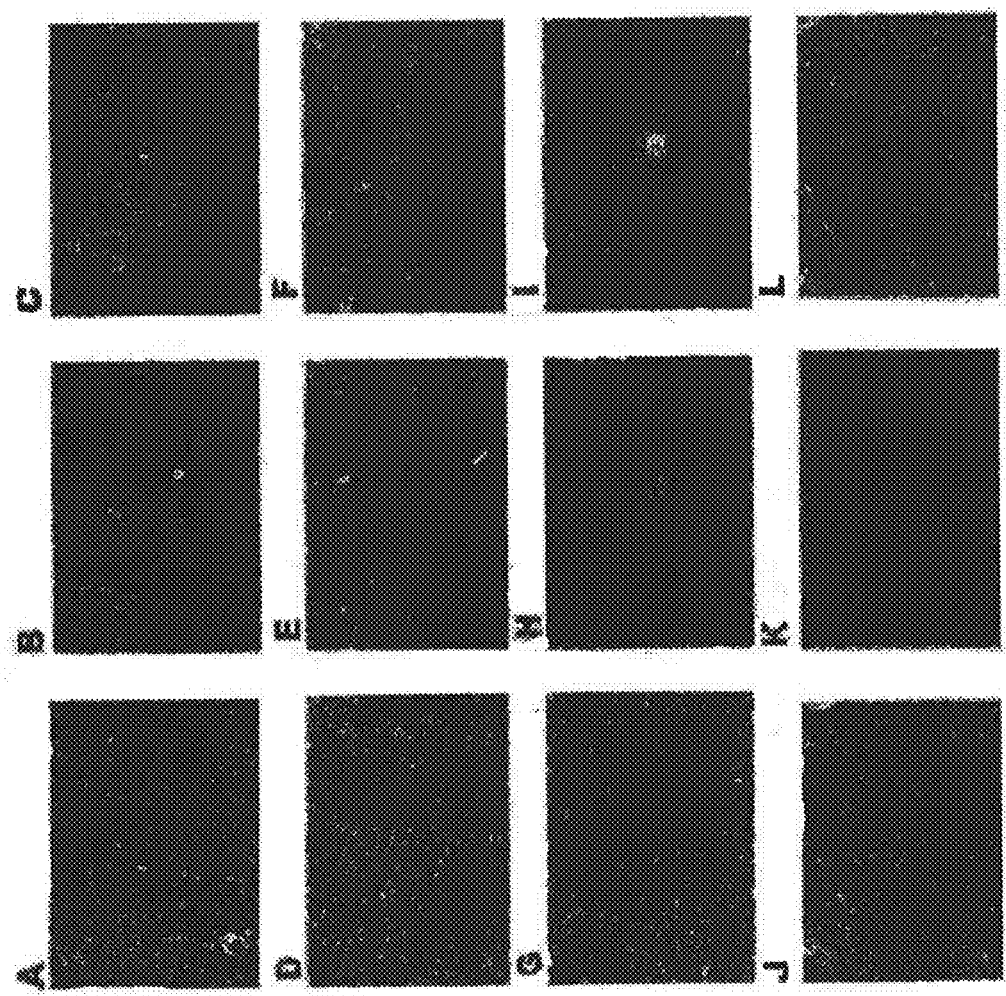
FIG. 10. Disruption of mitochondrial membrane potential in rBC-EGFP-infected tumor cells was examined by staining with DAPI and MitoTracker Red CMX-Ros. NDV-infected cells which had a disruption of the A>l,m and were undergoing apoptosis were shown by the diffuse cytoplasmic pattern of CMX-Ros with condensed chromatin. Tumor cells were infected with rBC-EGFP virus, treated 24 h postinfection with MitoTracker Red CMX-Ros for 2 h, and fixed later. Syncytium formation, EGFP expression, and mitochondrial membrane disruption in rBC-EGFP-infected cells are shown. (A) CaCo2 colon carcinoma cells, bright field; magnification, ×40. (B) Epifluorescence microscopy, ×40. (C) Diffuse staining of cytoplasm with MitoTracker Red merged with fluorescent image, ×40. (D) HEpG2 hepatocarcinoma cells, bright field, ×40. (E) Epifluorescence, ×40. (F) Diffuse cytoplasmic staining of MitoTracker Red with EGFP expression, ×40. (G) PO prostate cancer cells, bright field, ×40. (H) Epifluorescence, ×40. (I) Diffuse cytoplasmic staining of MitoTracker Red with EGFP expression, ×40. (J) HuTu80 cells, uninfected control cells, bright field, ×40. (K) Epifluorescence, ×40. (L) Punctuate cytoplasmic staining with MitoTracker Red, ×40.
Figure 11:
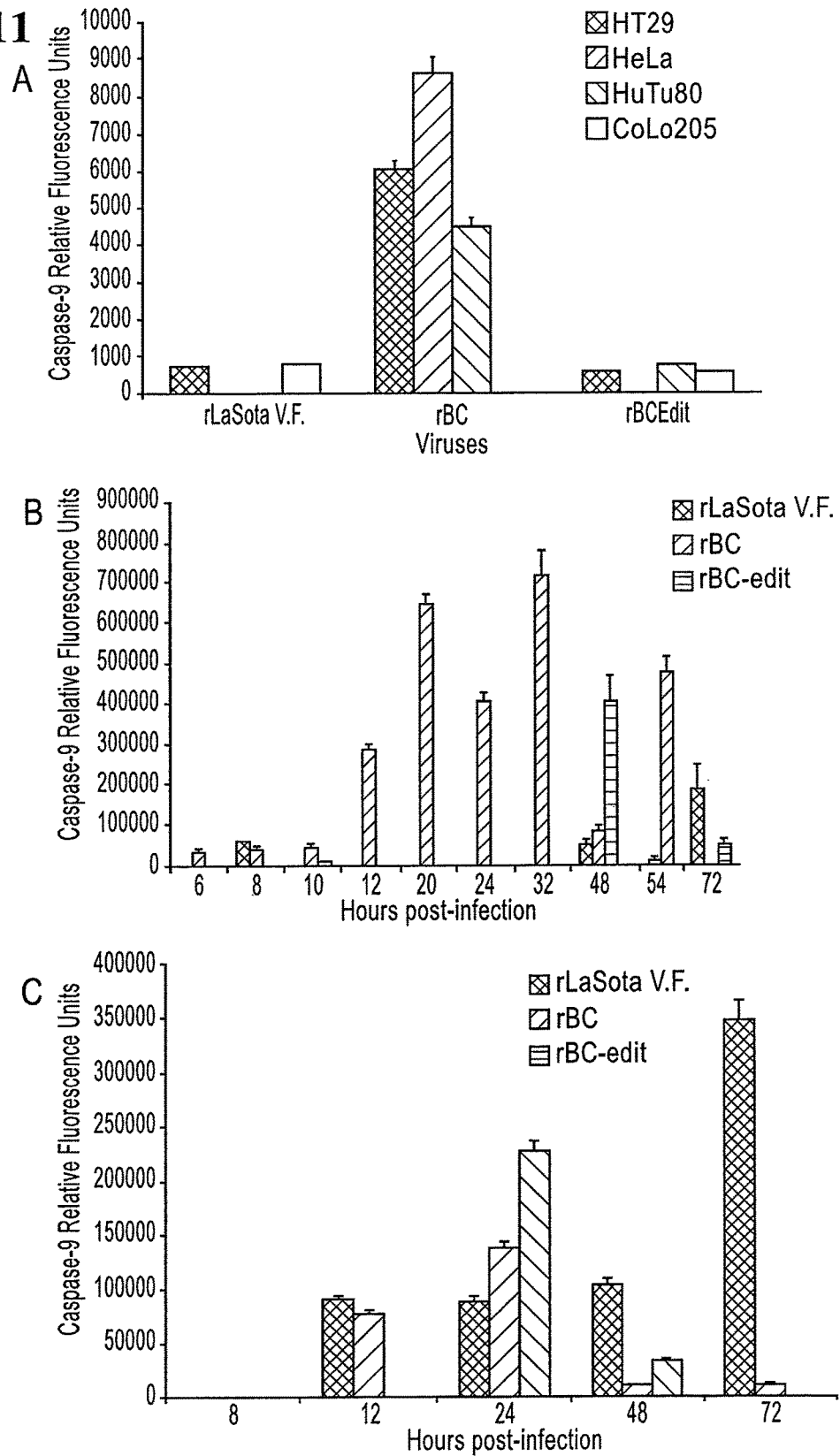
FIG. 11. Caspase-9 expression in NDV-induced apoptosis of tumor cells. DF1 and various human tumor cells were either mock infected or infected with rLaSota V.F., rBC, or rBC-Edit strains of NDV at an MOI of 0.01. Culture supernatants were assayed by ELISA for caspase-9 production at 48 h postinfection. (A) The relative fluorescence units over mock-infected controls are shown for DF1 cells and a few representative human tumor cells for caspase-9. (B) Kinetics of caspase-9 production in HuTu80 cells. (C) Caspase-9 production in SH-SY5Y neuroblastoma cells. Results represent mean values+SEM from two independent experiments.
Figure 12:
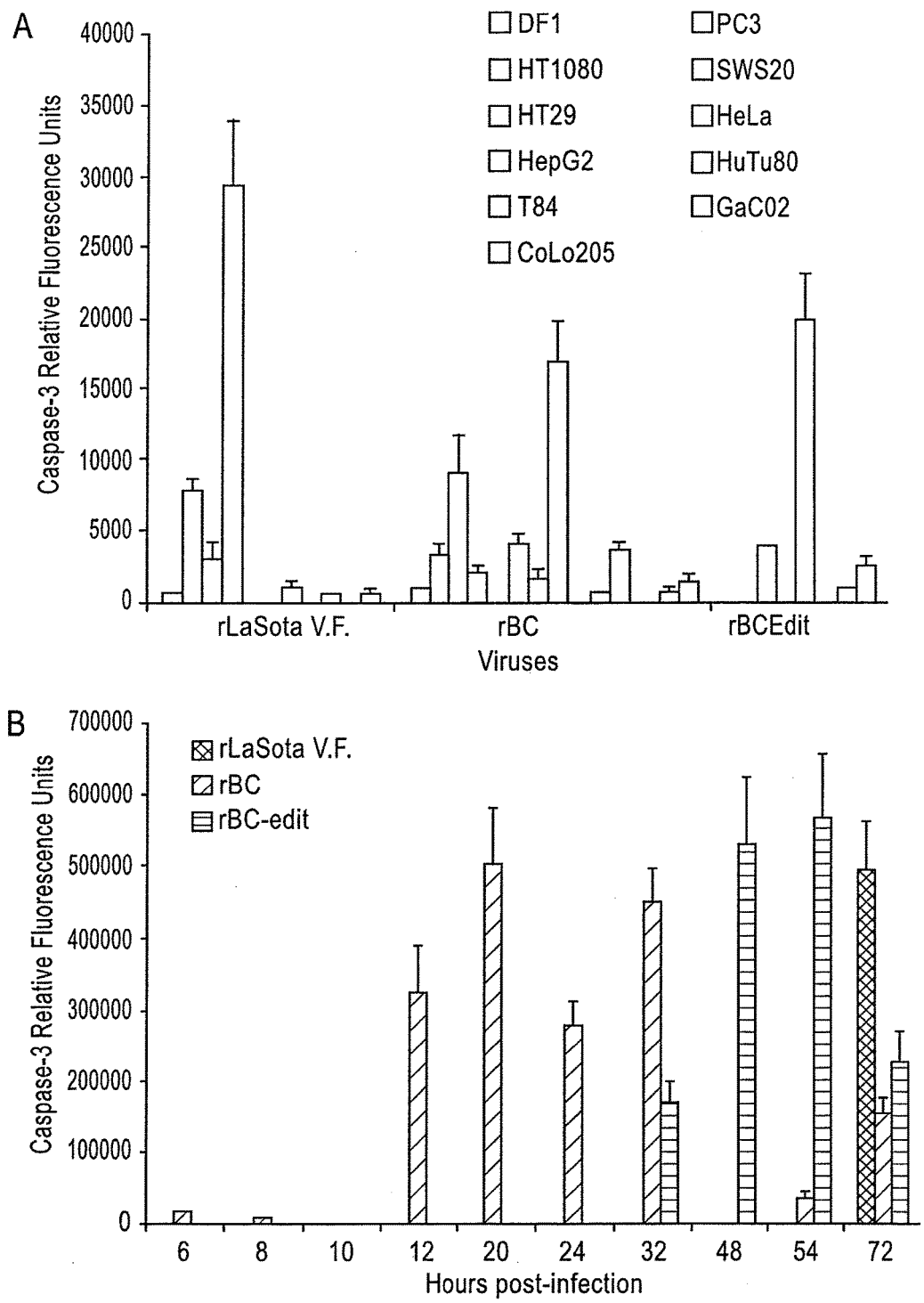
FIG. 12. Effector caspase-3 expression in NDV-induced apoptosis of tumor cells. DF1 and various human tumor cells were either mock infected or infected with rLaSota V.F., rBC, or rBC-Edit strains of NDV at an MOI of 0.01. Culture supernatants were assayed by ELISA for caspase-3 production at 48 h postinfection. (A) The relative fluorescence units over mock-infected controls are shown for DF1 and a few representative human tumor cells for caspase-3. (B) Kinetics of caspase-3 production in HuTu80 cells. (C) Caspase-3 production in SH-SY5Y neuroblastoma cells. Results represent mean values+SEM from two independent experiments. Broad-spectrum caspase inhibitor does not prevent replication of NDV in human tumor cells. HuTu80 cells were pretreated for 1 h with 100 μM Z-VAD-FMK prior to infection with rLaSota V.F., rBC, or rBC-Edit (MOI=1) virus or mock infection. Results represent mean values+SEM from two independent experiments.
Figure 12:
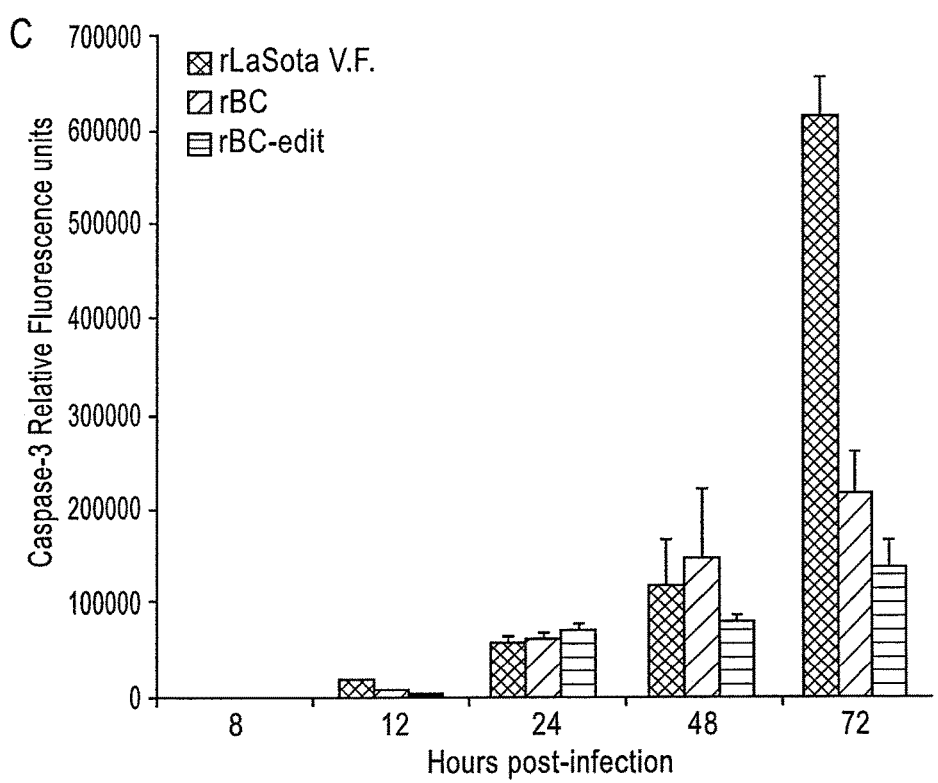

The present invention relates to recombinant oncolytic avian paramyxoviruses (APMV), such as Newcastle disease virus (NDV), compositions comprising them, and methods of using them to treat cancer and/or tumors in patient suffering therefrom. The present invention also provides recombinant oncolytic viruses, such as NDV, which incorporate additional therapeutic transgenes into their genomes. Such genetically-engineered oncolytic viruses may be used in accordance with methods for delivering the oncolytic viruses to specific sites and/or specific tumors within the body of a patient. The present invention further relates to methods of identifying recombinant viruses that are useful as oncolytic agents. Preferred embodiments of the present invention and their features and advantages may be understood by referring to FIGS. 1 through 38.

Newcastle disease virus (NDV), an avian paramyxovirus (APMV), is tumor-selective and intrinsically oncolytic. One aspect of the present invention relates to genetically-modified, recombinant NDV strains (rNDVs) that are cytotoxic to human tumor cell lines of ecto-, endo-, and mesodermal origin. Although the embodiments described herein are directed to rNDV, the present invention is not limited in application to NDV. The present invention also encompasses the use of other oncolytic, recombinant paramyxoviruses. The Paramyxoviruses include subfamily Paramyxovirinae, which includes genus Avulavirus (type species Newcastle disease virus), genus Henipavirus (type species Hendravirus; others include Nipahvirus), genus Morbillivirus (type species Measles virus; others include Rinderpest virus, Canine distemper virus, phocine distemper virus), genus Respirovirus (type species Sendai virus; others include Human parainfluenza viruses 1 and 3, as well some of the viruses of the common cold), genus Rubulavirus (type species Mumps virus; others include Simian parainfluenza virus 5, Menangle virus, Tioman virus), and genus TPMV-like viruses (type species Tupaia paramyxovirus). Subfamily Pneumovirinae includes genus Pneumovirus (type species Human respiratory syncytial virus, others include Bovine respiratory syncytial virus), and genus Metapneumovirus (type species Avian pneumovirus). Additional unassigned Paramyxoviruses include Fer-de-Lance virus, Nariva virus, Tupaia paramyxovirus, Salem virus, J virus, Mossman virus, and Beilong virus. The compositions and methods described herein may be carried out in any viruses in the Paramyxovirus family, including those that are presently-known, and those yet to be discovered.

As used herein, the term "recombinant" refers to a virus that has been altered by genetic engineering, by modification or manipulation of the genetic material found in the virus such that it is not identical to the naturally-occurring virus, or a naturally-occurring variant of the virus. According to one aspect of the invention, a recombinant Newcastle disease virus (rNDV) strain, which induces apoptosis in one or more tumor cell lines, is provided. According to a presently preferred embodiment, the rNDV may include cloned cDNA derived from a naturally-occurring NDV, such as NDV strains Beaudette C and LaSota.

The recombinant oncolytic viruses, such as rNDV, may be genetically-modified to include one or more transgenes that provide the rNDV with a property that is beneficial for the study of the virus and its effects, or is beneficial for the use of the recombinant oncolytic virus as a therapeutic agent. For example, the genetic modification may increase the production of interferon (IFN) by the infected cell, or increase viral resistance to IFN produced by the infected cell by modifying and/or deleting the V protein. The recombinant oncolytic viruses, such as rNDV, may also be genetically-modified to exhibit reduced pathogenicity in a natural host as compared to non-genetically-modified oncolytic viruses.

The recombinant oncolytic viruses may also be beneficially modified to exhibit enhanced induction of apoptosis, for example by modifying V protein expression, hemagglutinin expression, and/or apoptin expression. Enhanced expression of other proteins associated with apoptosis may also be provided by incorporating transgenes having oncolytic activity, preferably the viral fusion, hemagglutination and neuraminidase proteins. Also included within the scope of the invention are transgenes that induce the production of pro-apoptotic proteins such as cytokines, fas ligands, FADD, caspases-8, -9, -3, Smac/DIABLO, cytochrome c, IFN-beta, RANTES, IP-10, TNF-alpha, CD95 ligands, and TRAIL in tumor cells; that activate tumor suppressing genes such as p53 in tumor cells; or that activate caspases-8, -9, -3, Smac/DIABLO, cytochrome c present in tumor cells. Modifications to the recombinant oncolytic viruses of the present invention, and particularly to the rNDVs, may encompass any modification that results in activation of the mitochondrial cell death pathway, the death receptor-dependent apoptosis pathway, and/or the Apoptosis-Inducing Factor (AIF) pathway in a tumor cells. Without wishing to be bound by any particular theory, it is believed that the cytotoxicity of the recombinant viruses of the present invention to tumor cells is due to multiple caspase-dependent pathways of apoptosis.

The recombinant oncolytic viruses, such as rNDV, may also be modified to include one or more reporter genes that allow infected tumor cells to be identified. The reporter gene may be any gene that is produces detectable evidence of its expression, and is not natively-expressed in the cells to be infected by the recombinant oncolytic viruses, since the expression of the reporter is being used as a marker for successful infection. Commonly used reporter genes that induce visually identifiable characteristics usually involve fluorescent proteins, and examples include the gene that encodes green fluorescent protein (GFP), which causes cells that express it to glow green under UV light, and the enzyme luciferase, which catalyzes a reaction with a luciferin to produce light. Recombinant oncolytic viruses that are modified with such reporter genes permit infected tumor cells to be directly visualized. Other indirect visualization techniques that rely on affinity-binding with a fluorescently-labeled probe may also be used in accordance with the present invention. Preferably, any reporter genes that are incorporated into the recombinant oncolytic viruses of the present invention do not affect the ability of the virus to infect the tumor cells or to cause apoptosis in the tumor cells.

The recombinant oncolytic viruses, such as rNDV, may further include one or more genetic modifications to influence the ability of an infected tumor cell line to replicate in vitro. Such modifications may affect the ability of the cells to replicate in cell culture, including, but not limited to, trypsin dependence.

The recombinant oncolytic viruses, such as rNDV, which are provided in accordance with the present invention may also be used in a method for lysing tumor cells. These methods include the step of administering a therapeutically-effective amount of one or more recombinant oncolytic virus strains that is oncolytically-effective against the tumor cells. These methods may be used to provide targeted delivery of an oncolytic agent to a tumor site in a patient, or for use in lysing tumor cells in vitro. Presently preferred methods of lysing tumor cells are accomplished by use of an rNDV, particularly an rNDV that has been genetically-modified to affect its V protein expression, fusion protein expression, hemagglutinin expression, and/or apoptin expression. Enhanced expression of other proteins associated with apoptosis may also be provided in the genetically-modified rNDV, for example by incorporating transgenes that induce the production of pro-apoptotic proteins such as cytokines, fas ligands, FADD, caspases-8, -9, -3, Smac/DIABLO, cytochrome c, IFN-beta, RANTES, IP-10, TNF-alpha, CD95 ligands, and TRAIL in tumor cells; that activate tumor suppressing genes such as p53 in tumor cells; or that activate caspases-8, -9, -3, Smac/DIABLO, cytochrome c present in tumor cells.

The methods of lysing tumor cells in accordance with the invention may be extended to methods of reducing the size of a tumor in a patient following administration of the compositions of the invention. In the context of this aspect of the invention, "reducing the size of a tumor" refers to any decrease in the size of a tumor following administration of a recombinant paramyxovirus relative to the size of the tumor prior to administration of the recombinant virus. A tumor may be considered to be reduced in size if it is at least 10% smaller, 25% smaller, 50% smaller, up to 100% smaller (i.e., no tumor remaining) as measured by determination of tumor mass or size, either measured directly in vivo (i.e., by measurement of tumors directly accessible to physical measurement, such as by calipers) or by measurement of the size of an image of the tumor produced, for example by X-ray or magnetic resonance imaging.

Also provided in accordance with one aspect of the present invention is a composition comprising one or more recombinant oncolytic viruses, such as rNDV, and one or more pharmaceutically-acceptable carriers and/or excipients. Suitable pharmaceutically-acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the composition. The recombinant oncolytic viruses can be used in a composition with an adjuvant such as alum hydroxide, emulsions or submicron emulsions (for example, those described in U.S. Pat. Nos. 5,576,016, 5,662,932, 5,716,637, 5,961,970), or known pharmaceutical carriers, such as human serum albumin.

Presently-preferred compositions include an rNDV that has been genetically-modified to affect its V protein expression, fusion protein expression, hemagglutinin expression, and/or apoptin expression. Enhanced expression of other proteins associated with apoptosis may also be provided in the genetically-modified rNDV, for example by incorporating transgenes that induce the production of pro-apoptotic proteins such as cytokines, fas ligands, FADD, caspases-8, -9, -3, Smac/DIABLO, cytochrome c, IFN-beta, RANTES, IP-10, TNF-alpha, CD95 ligands, and TRAIL in tumor cells; that activate tumor suppressing genes such as p53 in tumor cells; or that activate caspases-8, -9, -3, Smac/DIABLO, cytochrome c present in tumor cells.

Preferably, the compositions are suitable for administration to an animal suffering from cancer, and are particularly suitable for administration to a human. The compositions containing a recombinant oncolytic virus may be provided in any suitable administration form, such as a suspension, an emulsion, a spray, a solution or any other formulation according to principles well known in the art. The compositions of the invention may be adapted for any suitable route of administration, including but not limited to intravenous, oral, buccal, intranasal, inhalation, topical application to a mucosal membrane or injection, including intradermal, intrathecal, intracisternal, intralesional or any other type of injection. For all forms of delivery, the recombinant oncolytic virus is most preferably formulated in a physiological salt solution, e.g. HANKS balanced salt solution.

The recombinant oncolytic viruses and compositions of the present invention may be administered in accordance with a method for treating cancer. According to this aspect of the invention, the recombinant oncolytic viruses or compositions containing them are administering to a patient in a therapeutically-effective amount. The recombinant oncolytic viruses or compositions containing them may be administered to the patient through any suitable route, as described above. One particularly preferred embodiment utilizes injection of rNDV or a composition comprising rNDV directly into a tumor or adjacent to the tumor.

According to another embodiment of the present invention, the method for treating cancer includes the step of administering to a patient (through any suitable route, as described above) a therapeutically effective amount of at least one recombinant oncolytic virus, or a composition containing at least one recombinant oncolytic virus. The recombinant oncolytic viruses or composition containing them is preferably rNDV, and is more preferably an rNDV that has been genetically-modified to affect its V protein expression, fusion protein expression, hemagglutinin expression, and/or apoptin expression. Enhanced expression of other proteins associated with apoptosis may also be provided in the genetically-modified rNDV, for example by incorporating transgenes that induce the production of pro-apoptotic proteins such as cytokines, fas ligands, FADD, caspases-8, -9, -3, Smac/DIABLO, cytochrome c, IFN-beta, RANTES, IP-10, TNF-alpha, CD95 ligands, and TRAIL in tumor cells; that activate tumor suppressing genes such as p53 in tumor cells; or that activate caspases-8, -9, -3, Smac/DIABLO, cytochrome c present in tumor cells.

Treatment of patients with cancer, in accordance with embodiments of the present invention, can be systemic, where the above-described compositions or even whole, isolated recombinant oncolytic viruses and/or proteins isolated from the viruses are administered to the patient. The form of administration may be intravenous, oral, buccal, intranasal, inhalation, topical application to a mucosal membrane, or injection, including intradermal, intrathecal, intracisternal, intralesional or any other type of injection. Preferably, rNDV, and is more preferably an rNDV that has been genetically-modified to affect its V protein expression, fusion protein expression, hemagglutinin expression, or apoptin expression, is administered locally and directly to a tumor or in its vicinity. Typically, the form of local administration is by injection, for example, intralesional injection.

A method of treating a patient with cancer in accordance with the invention may be evaluated for effectiveness by determining whether the patient exhibits any decrease in the size of a tumor following administration of the compositions or recombinant oncolytic viruses of the present invention, relative to the size of the tumor prior to administration of the compositions or recombinant oncolytic viruses. A tumor may be considered to be reduced in size if it is at least 10% smaller, 25% smaller, 50% smaller, up to 100% smaller (i.e., no tumor remaining) as measured by determination of tumor mass or size, either measured directly in vivo (i.e., by measurement of tumors directly accessible to physical measurement, such as by calipers) or by measurement of the size of an image of the tumor produced, for example by X-ray or magnetic resonance imaging.

In accordance with this aspect of the invention, a therapeutically-effective amount of the compositions and/or recombinant oncolytic viruses may be any amount that results in reduction in the size of a tumor present in a patient with cancer. The therapeutically-effect amount may also be any amount that results in a reduction in any symptoms experienced by the patient with cancer prior to the initiation of treatment. The compositions and/or recombinant oncolytic viruses of the present invention do not affect normal cellular processes and are thus not expected to be toxic to normal cells. Therefore, it would appear that there is no upper limit to the dose level which can be administered. Thus, to produce the same oncolytic effect achieved through intraneoplastic innoculation of virus by an intravenous route, significantly higher amounts of virus should be and could be administered. However, out of an abundance of caution, the appropriate dose level should be the minimum amount which would achieve the desired oncolytic effect. Further, it should be noted that the compositions and/or recombinant oncolytic viruses of the present invention can be administered repeatedly, depending upon the effect of the initial treatment regimen. If the patients's immune response to a particular composition and/or a specific recombinant oncolytic virus initially limit its effectiveness, additional administrations of compositions and/or recombinant oncolytic viruses having different serotypes and/or transgenes can be made.

All types of cancers may be included within the scope of the methods of treatment of the present invention. As non-limiting examples, the following cancers can be treated according to the present invention: glioblastomas, lung carcinomas, breast cancers, prostate cancers, melanomas, leukemias, and sarcomas.

The compositions may also be beneficially administered in combination with one or more chemotherapeutic agents and/or immunomodulating agents in order to increase the effectiveness of the anti-tumor or anti-cancer therapy. This embodiment is also included within the scope of the methods of treating cancer that are disclosed herein. When provided, the chemotherapeutic agents and/or immunomodulating agents are administered in accordance with standard dosing information known to those skilled in the art, which will necessarily vary based on the patient being treated, and the type of cancer from which the patient is suffering. In preferred embodiments of the invention, the administration of the compositions or recombinant oncolytic viruses in conjunction with chemotherapeutic and/or immunomodulating agents may result in an improved treatment outcome, as compared to treatment with the chemotherapeutic and/or immunomodulating agents alone, or may allow for a reduction in the dosage amount of the chemotherapeutic and/or immunomodulating agents, thereby reducing side-effects experienced by the patient.

Another aspect of the present invention is a method for identifying recombinant oncolytic viruses, such as rNDV, that are oncolytically-effective against a tumor cell line. This method includes the steps of isolating a tumor cell line from a tumor using methods known to those skilled in the art, and infecting the tumor cell line with a recombinant oncolytic virus strain in accordance with the examples described herein. In order to assess whether the strain is oncolytically-effective against the tumor cell line, an assay may be conducted to detect whether the tumor cell line has undergone apoptosis. Such an assay may detect one or more metabolic indicators of cell death that may be released by the cell upon lysis. Presently preferred methods are directed to the identification of rNDVs that are oncolytically-effective against a tumor cell line.

In accordance with certain aspects of the present invention, it has been discovered that NDV triggers apoptosis by activating the mitochondrial/intrinsic pathway, and that it acts independently of the death receptor/extrinsic pathway. Caspase-8 methylated SH-SY5Y neuroblastoma cells are equally sensitive to NDV as other caspase-8 competent cells. This demonstrates that NDV is likely to act primarily through the mitochondrial death pathway. NDV infection results in the loss of mitochondrial membrane potential and subsequent release of the mitochondrial protein cytochrome c, but the second mitochondrion-derived activator of caspase (Smac/DIABLO) is not released. In addition, early activation of caspase-9 and -3 is observed upon NDV infection. By contrast, cleavage of caspase-8, which is predominantly activated by the death receptor pathway, is a TRAIL-induced late event in NDV-mediated apoptosis of tumor cells. Without wishing to be bound by theory, it appears that the death signal(s) generated by NDV-infected tumor cells ultimately converges at the mitochondria, and that they act independently of the death receptor pathway.

Genetically-modified NDV with deficiencies in interferon antagonism or with additional genes were developed in order to monitor viral infection of tumor cells through enhanced GFP expression, or to incorporate a therapeutic suicidal transgene (Chicken anemia virus apoptotic protein "apoptin"). These genetically engineered NDV replicated in tumor cell lines of ecto-, endo-and mesodermal origin, and induced potent cytotoxicity, while remaining non-cytotoxic to normal human cells. NDV exploits tumor-specific defects in the interferon signaling pathway to exert its tumor selectivity and oncolysis. The mechanism of cytotoxicity in these cell lines is found to be due to multiple caspase-dependent pathways of apoptosis. In addition, it was found that NDV-induced apoptosis is initiated by the intrinsic mitochondrial pathway and amplified by the death receptor signals. Moreover, expression of apoptin from recombinant NDV (rNDV) enhanced the cytotoxicity significantly. Recombinant NDV strain "LaSota" mutant with a virulent fusion protein cleavage site motif efficiently killed 85% of the cell lines tested, including colon cancer cell lines.

The oncolytic potential of rNDV with deficiencies in replicative abilities, cell and tissue tropism, and interferon antagonism was explored in chicken cells. In addition, a reporter (EGFP) gene was engineered to permit virus tracking, and a therapeutic suicidal (apoptin) transgene was incorporated into rNDV, in order to demonstrate the oncolytic efficacy in a range of tumor cells. rNDV that are attenuated for the natural host were also tested to assess their tumor selectivity and cytotoxic capabilities. Such cytotoxicity studies, which are further described in the illustrative applications section, suggest that rNDV is a potent cytotoxic agent specifically against cancer cells and could be developed as a cancer gene therapy agent, either alone or in combination with therapeutic transgenes.

Considerable evidence exists that the ability of a virus to selectively kill tumor cells may be determined by cancer-specific defects in innate anti-viral responses. Defects or downregulation of components of the interferon pathway may be a common feature of a broad range of malignancies, and these defects may be responsible for the tumor specificity demonstrated by a variety of oncolytic viruses. NDV tumor cell activity may be based on cancer-specific defects in the interferon pathway, and without wishing to be bound by theory, it appears from the experiments carried out in the development of the rNDVs of the present invention that defects in the tumor cells in mounting an IFN-α defense, as compared to normal cells, is a primary mechanism by which NDV attains tumor selectivity. In most body cells, activation of latent IRF-3 triggers expression of only a small subset of IFN genes, in particular, IFN-β. This early IFN acts in an auto- or paracrine manner by JAK/STAT signaling to stimulate the synthesis of IRF-7, which controls transcription of many additional members of the IFN-α gene family. The presence or absence of an IFN-α response largely determines the outcome of infection, and in the experiments described herein, all of the tested strains induced a primary transcriptional wave of IFN-β synthesis.

Because NDV replicates in cancers of very diverse origin, it is likely that the virus exploits cellular signals that commonly occur in transformation and carcinogenesis. In fact, the results set forth herein support the hypothesis that NDV exploits specific defects in the interferon pathway to exert its oncolytic activity, rather than through ras activation-induced permissiveness. This is consistent with the finding that robust stimulation of interferon by NDV in normal cells successfully prevents the virus from being cytolytic.

The ability to engineer NDV also affords a viable system for studying the mechanistic basis of tumor selectivity and oncolysis by NDV. To this end, several recombinant NDV (rNDV) with or without transgenes were developed, and their replication and cytotoxicity was studied in a variety of tumor cell lines. This study incorporated NDV strains with the following properties (a) low-pathogenic strain to the natural host that only replicates in the presence of exogenous trypsin in cell culture, (b) low-pathogenic strain with mutation in the F protein to allow replication in cell culture without exogenous trypsin, (c) low pathogenic strain with HN protein replaced from a moderately pathogenic strain, (d) moderately pathogenic strain with intact IFN antagonistic function, (e) moderately pathogenic strain with a defect in IFN antagonism, and (f) a moderately pathogenic strain that expresses enhanced GFP or chicken anemia virus (CAV) apoptotic protein "apoptin" (viral protein 3, VP3). See Table 1. Presently-preferred rNDV strains include, but are not limited to, rLaSota V.F., rBC-VP3 and rBC-Edit. These recombinant viruses have a number of properties which makes them suitable as oncolytic viruses for tumor therapy: (a) they are non-pathogenic to humans, and it is likely that they would be associated with few side effects; (b) because multiple serologically defined types exist for avian paramyxoviruses (APMV), different serotypes (APMV-2 through 9) can be engineered to deliver therapeutic transgenes; (c) It is possible to construct rNDV with multiple transgenes to enhance oncolytic efficacy; and (d) they could be engineered for targeting to specific sites.

The tumor selectivity of NDV and apoptin were utilized in order to develop an rNDV that exhibits enhanced oncolytic efficacy. The predominantly mitochondrial apoptotic pathway of apoptosis induced by NDV was augmented by the expression of apoptin. rNDV-apoptin proved to be an efficient oncolytic agent to tumors of ecto-, meso-, and endodermal origin, with a very low EC50 (over all EC50=0.012), except in mammary and colon carcinoma cell lines.

Studies reveal that a non-pathogenic NDV (rLaSota V.F.) with modified fusion protein cleavage site showed cytotoxicity against a wide range of tumor cells (86%) while a moderately pathogenic NDV (rBC) was cytolytic in only 57% of the tested tumor cells. However, the rBC virus efficiently lysed tumor cells at a relatively lower MOI. Engineering an additional reporter transgene into the rBC virus did not lower its oncolytic efficacy as the cytotoxic range and effective concentration to lyse tumor cells of rBC and rBC-EGFP viruses were similar. The differences in the cytotoxic abilities of rLaSota V.F. and rBC against tumor cells were observed despite their similar F protein cleavage site sequences.

Because the virulence of NDV differs in the natural host (chickens), the observed differences in tumor cell cytotoxicity might be a reflection of the differences in the other major NDV surface glycoprotein, the hemagglutinin (HN) protein. The HN protein has been shown to mediate apoptosis in NDV-infected cells (Zeng et al., "Induction of interferon-alpha and tumor necrosis factor-related apoptosis-inducing ligand in human blood mononuclear cells by hemagglutinin-neuraminidase but not F protein of Newcastle disease virus," *Virology* 297:19-30 (2002)). There are 17 amino acid differences in the HN protein between rLaSota and rBC viruses that might contribute to these differences. Since all strains of NDV enter all types of cells using sialic acid receptors, the observed differences in cytotoxicity against tumor cells by these viruses are likely due to HN protein functional differences that do not alter receptor specificity. It is highly likely that these differences could be due to a difference in receptor avidity resulting from the amino acid differences in the HN protein.

It is also possible that other viral proteins such as the V and L proteins may be responsible for differences in cytotoxicity in rNDV. The rBC-edit virus shows a wider spectrum of cytotoxicity with a very low MOI. This could be due to the absence of expression of the V protein, which functions as an antiapoptotic protein.

In the experiments conducted herein, NDV activated caspase-8, despite TRAIL-resistance and caspase-8 methylation in neuroblastoma cells, and did not inhibit NDV-mediated apoptosis. Despite TRAIL-resistance, the rBC-edit virus and rLaSota V.F. virus were apoptotic in HT-29 and CaCo2 cells, but the rBC virus was non-cytolytic in these cells, probably due to the potent and apoptotic activity of the V protein. These results confirm the finding that NDV-induced TRAIL only potentiates the intrinsic apoptosic pathway.

The presence of the general caspase inhibitor z-VAD-fmk during the infection cycle prevented apoptosis and delayed cell death, but did not inhibit CPE induced by the virus after 48 h PI. In addition, activation of caspases in NDV-infected cells is not a requirement for viral replication, since caspase inhibitors had no effect on virus replication. These data show that NDV kills cancer cells primarily by activation of the mitochondrial death pathway and, furthermore, they indicate that the caspase-8/9 independent signal-amplification loop is not important for NDV-induced death. While caspase-8 may play a role in amplifying effector caspase activation, this appears to be unnecessary for NDV-induced apoptosis. The delay in TRAIL expression also supports this view.

It has also been discovered that IFN-sensitive rNDV that replicates in tumor cells, but not in normal cells, is a better oncolytic agent than its parental type. These strains were chosen to detect the differences in cell death pathways induced by low-pathogenic and moderately-pathogenic NDV strains in tumor cells. The IFN-sensitive virus lacks the expression of the antiapoptotic and IFN antagonistic V protein and replicates only in cells that lack a functional IFN system. The rNDV that expresses EGFP was used to prove that oncolytic rNDV is a trackable virus in vivo and could be exploited to study the mechanism of cell death in vitro.

Figure 18:
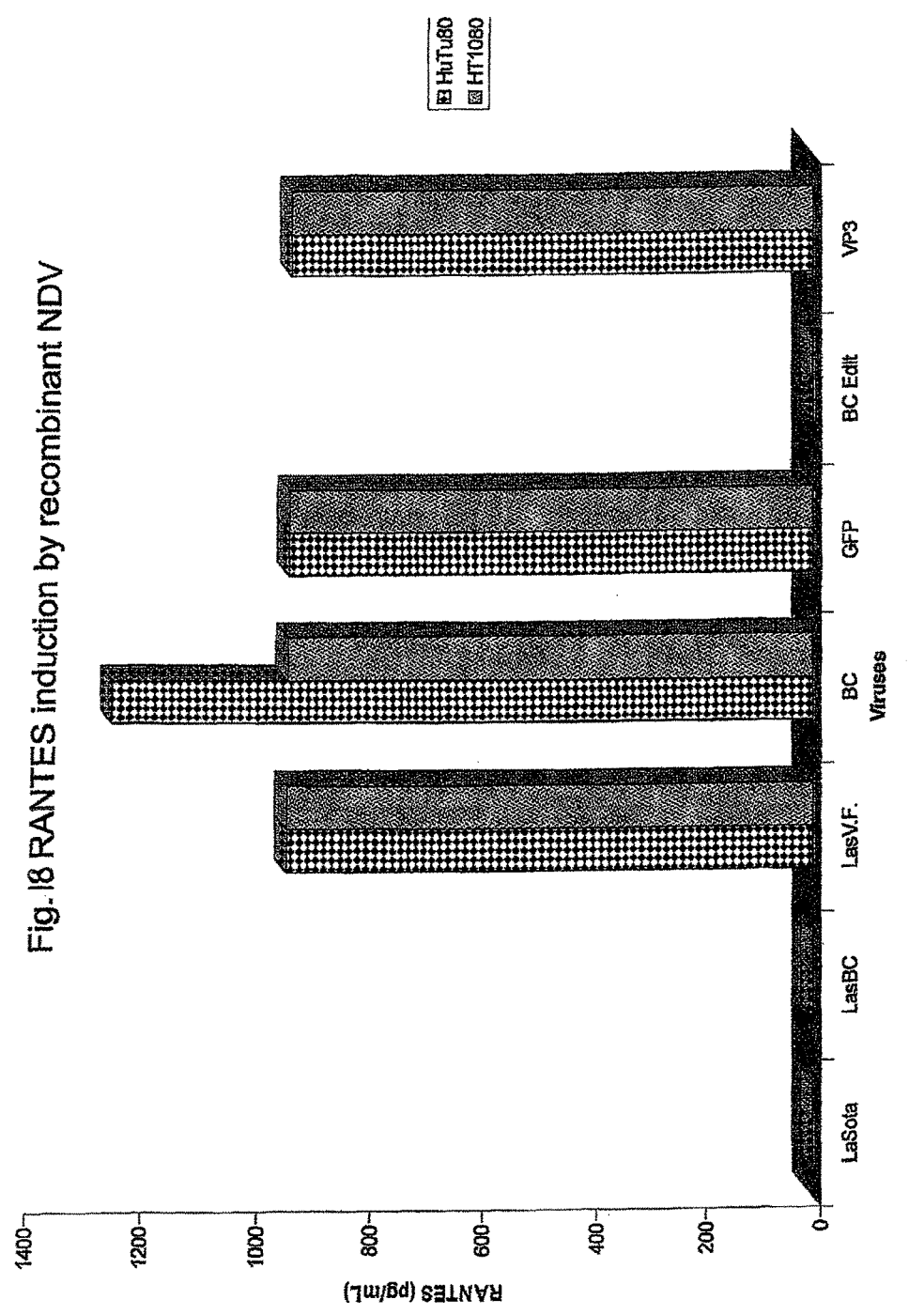

Primary response genes, such as IFN-β, appear to be induced by rNDV in all the cell lines tested. RANTES, another primary response gene was induced only in the fibroblast cell lines (FIG. 18). IP-10 was induced in fibroblast cell lines such as HT1080, prostate cancer epithelial cell line PC3, HuTu 80 intestinal epithelial cells, and colon cancer cell lines CaCo2 and HT29 (FIG. 19).

Figure 20:
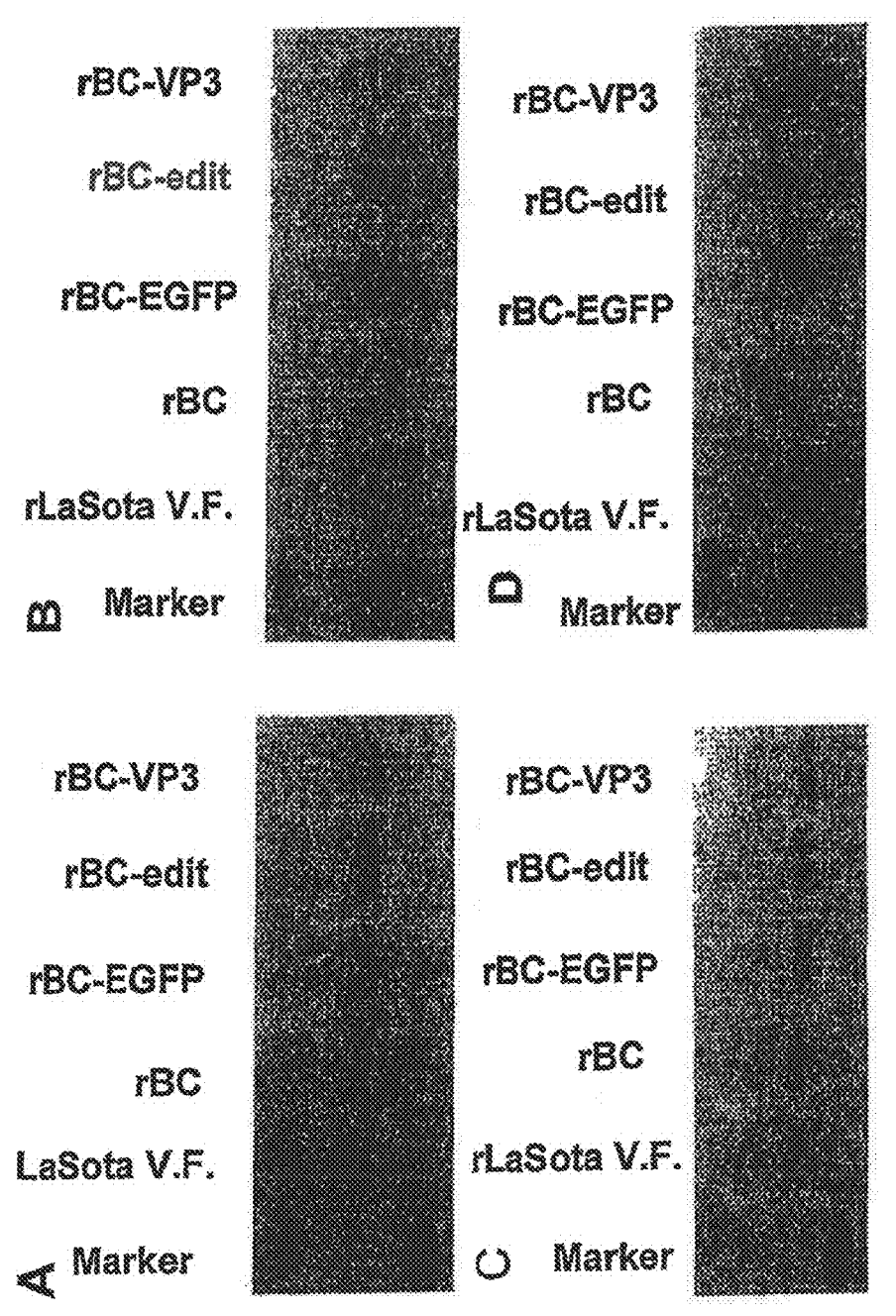

Secondary response genes that require the production of IFN-β protein and the autocrine or paracrine activation of the JAK/STAT pathway were differentially induced by IFN-resistant and IFN-sensitive (V defective) viruses depending on the cell lines (see IRF-7 in FIG. 20). No impairment in the induction of JAK/STAT pathway (see STAT 1 or STAT 2 in FIG. 21) was observed in tumor cells and, therefore, the signaling block must be downstream of the JAK/STAT pathway. As a consequence of impaired IRF-7 production, tertiary response genes like IFN-α were not induced in many of the cell lines. These results indicate that rNDV trigger activation of IRF-3 and the subsequent transcription of a cohort of genes to induce the primary antiviral state, but through coordinated expression of viral gene products either blunts secondary and tertiary responses or exploits the tumor specific defects in the IFN pathway. The absence of tertiary response (IFN-α) fails to fortify the primary antiviral state, thus permitting virus replication.

Particularly preferred embodiments of the present invention will now be described with respect to the following non-limiting illustrative examples. Although each of the embodiments above has been described as being applied to NDV, the present invention is not limited in application to NDV. The following illustrative examples of the present invention can also be used to produce oncolytic viruses derived from any Paramyxovirus strain, for example.

ILLUSTRATIVE EXAMPLES

Experimental Procedures

Cells. DF 1 chicken embryo fibroblast, HeLa, HEpG2, CaCo 2, and HuTu80 cells were grown in Dulbecco's modified Eagle's medium (DMEM) with 10% fetal calf serum (FCS), 100 µg/ml penicillin and 0.1 µg/ml streptomycin (Invitrogen, Grand Island, N.Y.). T84 colon cancer and SH-SY5Y neuroblastoma cells were grown in a 1:1 mixture of DMEM and Hams F12 with 10% FCS and antibiotics. THP-1, CCRF-CEM, PC 3, SW 620, MCF 7, CoLo 205, HT29, and HT1080 cells were grown in RPMI-1640 medium supplemented with 10% FCS and antibiotics. The cells were grown at 37° C. with 5% $CO_2$ in a humidified incubator.

Viruses. The plasmid pNDVfl expressing the full-length antigenome of moderately pathogenic NDV strain Beaudette C (BC) and avirulent NDV strain LaSota have been described previously (Huang et al., "High-level expression of a foreign gene from the most 3'-proximal locus of a recombinant Newcastle disease virus," *J Gen Virol* 82:1729-36 (2001); Krishnamurthy et al., "Recovery of a virulent strain of Newcastle disease virus from cloned cDNA: expression of a foreign gene results in growth retardation and attenuation," *Virology* 278:168-82 (2000)) and were used to construct mutants, chimeric viruses or viruses with additional transgenes. The construction and recovery of P gene editing mutant (rBC-edit) recombinant LaSota (rLaSota), and recombinant LaSota with Virulent Fusion protein cleavage site (rLaSota V.F.), have been described in detail elsewhere (Huang et al., "High-level expression of a foreign gene from the most 3'-proximal locus of a recombinant Newcastle disease virus," *J Gen Virol* 82:1729-36 (2001); Huang et al., "Newcastle disease virus V protein is associated with viral pathogenesis and functions as an alpha interferon antagonist," *J Virol* 77:8676-85 (2003); Panda et al., "Role of fusion protein cleavage site in the virulence of Newcastle disease virus," *Microb Pathog* 36:1-10 (2004)). The plasmid pNDVfl expressing the full-length antigenome of NDV Beaudette C was used to construct the P gene editing mutant. The AscI-SacII fragment containing the P gene editing site from pNDVf1 was subcloned into pGEM-7Z (+) (Promega, Madison, Wis.) between XbaI and HindIII by using a specific primer pair with XbaI and HindIII site overhangs. Mutations were introduced into the P gene editing site by PCR using a phosphorylated primer pair to amplify the plasmid pGEM-7Z (+) containing the AscI-SaCII insert. The primer pair P3 (5'-$^{2282}$gAAaGGCCTATG-GTCGAGCCCCCAAG$^{2307}$-3) and P4 (5'-$^{2281}$TTAGCAT-TGGACGATTTATTGCTGAGC$^{2255}$-3) was used to introduce two nucleotide changes to disrupt the P gene editing site. The mutations introduced were silent with regard to the P reading flame. The mutated AscI and SacII fragments were excised to replace the corresponding counterpart in pNDVfl. Recombinant BC-EGFP was constructed by inserting an extra cistron-encoding EGFP between the P and M gene sequences. Briefly, by site-directed mutagenesis, an Xba I site was created in the non-coding region of the P gene in the SacII-Not I fragment of the NDV antigenome. Subsequently, the EGFP coding sequence was amplified from pEGFP (Clontech, Mountain View, Calif.) by PCR with an Xba I overhang at both ends and with authentic NDV gene start and gene stop sequences. The EGFP cistron was digested with Xba I and cloned into the SacII-Not I subclone. The plasmid pBCEGFP was constructed by re-inserting the SacII-NotI fragment into the plasmid pNDVfl. The presence of the EGFP gene was confirmed by sequencing the respective full-length clone. The rescue procedure for obtaining the recombinant viruses from the infectious full-length clones of NDV has been described in detail elsewhere (Huang et al., "High-level expression of a foreign gene from the most 3'-proximal locus of a recombinant Newcastle disease virus," *J Gen Virol* 82:1729-36 (2001); Krishnamurthy et al., "Recovery of a virulent strain of Newcastle disease virus from cloned cDNA: expression of a foreign gene results in growth retardation and attenuation," *Virology* 278:168-82 (2000)). Briefly, HEp-2 cells at 80 to 90% confluence in a six-well plate were infected with vaccinia MVA-T7 virus at 1 focus-forming unit per cell. The cells were then transfected with the three expression plasmids encoding the NP, P, and L proteins of NDV strain Beaudette C or LaSota and a fourth plasmid containing the mutated NDV cDNA. Three days after transfection, the cell culture supernatant was harvested, briefly clarified, and then used to infect fresh HEp-2 cells. Three days later, the supernatant was harvested and passed on to the DFI cells until virus-specific CPE appeared The recovered viruses were plaque purified on DFI cells and propagated in 9-day-old embryonated SPF chicken eggs for use as virus stocks.

Sequence analysis of recovered viruses. Virus stocks were propagated twice in DF1 cells before sequence analysis. Total RNA from infected cells was prepared using Trizol (Invitrogen). The nucleotide sequence of the region of the P gene that contains the editing site was analyzed by sequencing a reverse transcriptase PCR (RT-PCR) fragment obtained using specific primers described earlier (Huang et al, 2003), and the presence of the inserts (EGFP or apoptin) in the recombinant viruses were verified by sequencing the RT-PCR fragments with respective P and M gene or HN and L gene specific internal primers.

Interferon Assays. The relative sensitivity of the parental and P gene mutant viruses to exogenously added recombinant chicken IFN-α (chIFN-α) was measured on DF1 cells. Briefly, cells in six-well culture dishes at 70 to 80% confluence were incubated with chIFN-α (a gift from Dr. Philip I. Marcus, University of Connecticut) at various concentrations. After 24 h of incubation at 37° C., the cells were infected with rBC, rBC-v Stop, or rBC-edit at an MOI of 0.01 in a volume of 100 μl. vesicular stomatitis virus (VSV) strain Indiana, a known IFN-sensitive virus, was included as a positive control. Cells were adsorbed with virus for 2 h, the residual virus in the inoculum was removed, and then cells were incubated for 48 h in medium containing 5% fetal calf serum. The virus yields in the culture supernatants were determined by plaque assay in DFI cells. (FIG. 13)

IFN-α levels were measured using a human interferon alpha multi-subtype ELIZA kit (41105-1; PBL BioMedical) per manufacture's instructions. Various cell lines were infected with rNDV at an MOI of 10. One hundred microliter of culture supernatant in triplicate was collected at 48 h post-infection and incubated in a 96-well microliter plate along with standards supplied by the manufacturer. In addition, a kinetic assay of IFN-α expression was performed in HuTu80 cells with rNDV strains. (FIG. 16) Cells were infected with rNDV (rLaSota V. F., rBC, rBC-edit, and rBC-VP3) at an MOI of 10 and the levels of IFN-α in the culture supernatants collected at 0, 6, 8, 10, 12, 14, 20, 24, 28, 38, 48, and 72 h post-infection were measured by ELISA as described above. (FIG. 17) IFN-β production was measured at 48 h post-infection in culture supernatants (in triplicate) using a human IFN-β ELISA kit (41100-1; PBL Biomedical). (FIG. 14) Samples were processed as per manufacturer's instructions and then read on a VICTOR multilabel plate reader. The kinetics of IFN-β production were assayed in culture supernatants collected at 0, 6, 8, 10, 12, 14, 20, 24, 28, 38, 48, and 72 h post-infection from HuTu 80 cells infected with rNDV at 10 MOI, using the same IFN-β kit as described. (FIG. 15)

Western blot analysis. Chicken embryo fibroblast (DFI) cells or tumor cell lines in 10 cm dishes were infected with rNDV at an MOI of 5. One hour after infection, the media were removed and replaced with OptiMEM for the remaining duration of the experiment. Virus infected cells were harvested at the indicated times, pelleted by centrifugation, washed with ice-cold phosphate-buffered saline, and lysed by sonication in 150 μl of lysis buffer (1% NP40, 0.15 M NaCl, 5.0 mM EDTA, 0.01 M Tris (pH 8.0), 1.0 mM PMSF, 0.02 mg/ml leupeptin, 0.02 mg/ml trypsin inhibitor). Lysates were cleared by centrifugation (15,000×g, 2 min), normalized for protein content, mixed 1:1 with sample buffer, boiled for 5 min, and stored at -70° C. To prepare mitochondrial-free extracts, cells were pelleted, washed twice in ice-cold PBS, and incubated on ice for 30 min in buffer containing 220 mM mannitol, 68 mM sucrose, 50 mM PIPES-KOH (pH 7.4), 50 mM KCl, 5 mM EDTA, 2 mM $MgCl_2$, 1 mM DTT, and protease inhibitors cocktail (Roche, Indianapolis, Ind.). Lysates were centrifuged at 14,000 xg for 15 min at 4° C. to remove debris. Supernatants and mitochondrial pellets were prepared for electrophoresis as above. Proteins were separated by 10% SDS-PAGE and transferred to nitrocellulose membrane for immunoblotting. Blots were then probed with the specific antibodies. Proteins were visualized using the TMB membrane substrate (Kirkegaard and Peary Laboratories, Gaithersburg, Md.). The following antibodies were used for immunoblotting: Statlα (sc-345; Santa Cruz Biotechnology, Inc., Santa Cruz, Calif.), Stat 2 (sc-476; Santa Cruz), monoclonal anti-human TRAIL/TNFSF10 (MAB687; R&D Systems, Minneapolis, Minn.), anti-cytochrome C (sc-13561; Santa Cruz), NDV MCA (monoclonal antibody cocktail directed against the NDV HN protein), and Actin (sc-8432; Santa Cruz).

WST-1 assay. A colormetric assay for analyzing the cell viability was based on the cleavage of the tetrazolium salt WST-1 by mitochondrial dehydrogenases. In each experiment, the best cell line was seeded into 96-well plates at $1\times10^4$ cells/well in growth medium (DMEM+10% FCS or RPMI+10% FCS; Invitrogen). Following overnight incubation (37° C., 5% $CO_2$), media were removed by aspiration and to each well 20 μl of virus containing OptiMEM (Invitrogen) was added, ranging in 10-fold increments from 0.01 to 10 MOI or negative control media with no virus. Each virus dose was tested in replicates of six. After 60 min incubation to allow virus attachment, 80 μl of growth medium was added to each well, and the plates were incubated for another 48 h. Cell viability was measured by adding 10 μl of WST-1 (Roche) reagent/well. An expansion of the number of viable cells increases the overall activity of mitochondrial dehydrogenases. This leads to an increase in the amount of formazan dye that is formed and directly correlates with the number of metabolically active cells in the culture. The formazan dye produced by metabolically active cells was quantified 2 h after the addition of WST-1 reagent, by measuring in a scanning multiwell spectrophotometer at 450 nm. Background absorbance was subtracted using the control media and WST-1 reagent.

RT-PCR of NDV HN. RNA was extracted from tumor cells infected with lNDV strains (MOI 10) 48 h post-infection using Trizol (Invitrogen) according to manufacturer's instructions. One microgram of RNA was reverse transcribed with NDV HN-specific primer and Superscript reverse transcriptase (Invitrogen). For Taq PCR, 2 microliter of the cDNA was used as the template and amplified using NDV-HN primers (primer sequences available upon request).

Annexin V staining and DNA laddering. Nuclei of rNDV infected tumor cells were visualized after cell fixation in 4% paraformaldehyde, permeabilization with 90/10 mixture of ice-cold acetone and water, and DNA staining with 1.0 microgram of 4',6-diaimidino-2-phenylindole (DAPI) (Sigma-Aldrich, St. Louis, Mo.). Externalization of phosphatidyl serine from the inner to the outer leaflet of the cell membrane in rNDV infected tumor cells was detected using Annexin V-FITC kit (BD Biosciences, San Jose, Calif.) as per manufacturer's instructions at 6 and 14 h PI. Propidium iodide was used as the vital dye to differentiate live, dead and apoptotic cells by epifluorescence microscopy (Axiovert 200, Carl Zeiss, Thornwood, N.Y.). Intranucleosomal DNA fragmentation in infected cells was detected by using the Apoptotic DNA ladder kit (Roche). A kinetic assay of DNA fragmentation was performed in HuTu80 cells at 8, 10, 12, 24, and 48 h PI.

TNF-α and TRAIL. TNF-α production by rNDV in SV-HUC1 and tumor cell lines was tested at 48 h PI using human TNF-α Quantikine ELISA kit (HSTA00C; R&D systems). The time-course of TNF-α induction by rNDV strains (MOI 10) was followed in HuTu 80 cells at 6, 10, 2, 20, 24, 48, and 72 h PI using the above ELISA kit. The TRAIL ActivELISA kit (Imgenex, San Diego, Calif.) was used to detect the soluble form of TRAIL (sTRAIL) by a sandwich ELISA protocol according to the manufacturer's recommendations. Culture supernatants (48 h PI) from rNDV-infected (MOI 10) DF1 or tumor cells or standard dilutions of recombinant soluble TRAIL were tested in triplicate using the TRAIL, ActivELISA kit. sTRAIL is captured on the microtiter plate using an anti-TRAIL antibody. The amount of bound TRAIL was then detected by TRAIL specific detecting antibody followed by incubation with alkaline phosphatase-conjugated secondary antibody and color reaction with p-nitrophenyl phosphate. Optical density was measured at 405 nm and compared with those for the standard dilutions.

Caspase assay. The BD APOAlert™ Caspase fluorescent assay kits (BD Biosciences) for caspases-3, -8, -9 were employed to detect the activation of different caspases in infected cell lysates. DF 1 cells and various tumor cell lines were infected with rNDV strains (MOI 10), and harvested at 48 h PI and tested for activated caspases using fluorogenic substrates as per manufacturer's instructions. In time-course experiments with HuTu80 cells, $1\times10^6$ cells/time point were used. Cells were centrifuged at 200×, g, supernatants were removed, and the cell pellets were frozen at 70° C. until all the time points were collected. Assays were performed in 96-well plates and analyzed using a fluorescent plate reader (PerkinElmer, Boston, Mass.). The Caspase-3 and Caspase-8 fluorescent assay kits detect the emission shift of 7-amino-4-trifluoromethyl coumarin (AFC). The AFC substrate conjugate usually emits blue light ($\lambda$max=400 nm); however, cleavage of the substrate by the appropriate caspase liberates AFC, which fluoresces yellow-green ($\lambda$max—505 nm). Similarly, the Caspase-9 Fluorescent Assay Kit detects the emission shift of 7-amino-4-methyl coumarin (AMC). The LEHD-AMC conjugate emits in the UV range ($\lambda$max=380 nm); however, free AMC fluoresces blue-green at 440 nm upon liberation by caspase-9. The amount of fluorescence detected is directly proportional to amount of caspase activity. Results of all experiments are reported as means+S.E.M.

Caspase Inhibition. The selective inhibitors Ac-DEVD-CHO (inhibitor of caspases 3, 7 and 8), Z-IETD-fmk (inhibitor of caspases 6, 8, 9 and 10) and Ac-LEHD-CHO (inhibitor of caspase-9) were used for caspase inhibition experiments. For apoptosis-inhibition assays, HuTu 80 cells were incubated with one of the following inhibitors: 600 μM Ac-DEVD-CHO, 600 μM Ac-LEHD-CHO or 120 μM Z-IETD-fmk for 3 h or for 1 h with 100 μM Z-VAD-fmk prior to infection with rBC-EGFP (MOI 1), rLaSota V.F., rBC, or rBC-Edit viruses. Control cultures were treated with the appropriate amount of DMSO (0.1%, final concentration), used as a solvent for peptide inhibitors. After virus adsorption for 1 h, the media were removed and replaced with OptiMEM. The infected cells were monitored for either EGFP expression or CPE, and virus production at 6, 8, 10, 12, 14, 16, 20, 24, 38, 48, and 72 h PI. Apoptosis induction in these cells was evaluated using apoptotic DNA ladder kit (Roche) for intranucleosomal DNA fragmentation at the time points indicated above.

Mitochondrial membrane stability assay. To detect mitochondrial membrane integrity, tumor cells were cultured on 2A-well cell culture plates. Fifteen minutes before fixation, the Mito Tracker Red (750 nM) (CMX Ros; Molecular Probes, Eugene, Oreg.) dye was added to the culture medium. Accumulation of the dye was allowed to occur for 20 min at 37° C. Then, the cells were fixed with 496 paraformaldehyde for 15 min and permeabilized with a 90/10-acetone/water solution during 2 min at −20° C. After 3 washes, cells were labeled with or without DAPI and mounted in buffered glycerol and analyzed by epifluorescence microscopy. Mitotracker Red fluorescence was induced by illumination at 543 nm and was detected using a 560-nm long pass filter.

Results

Figure 13:
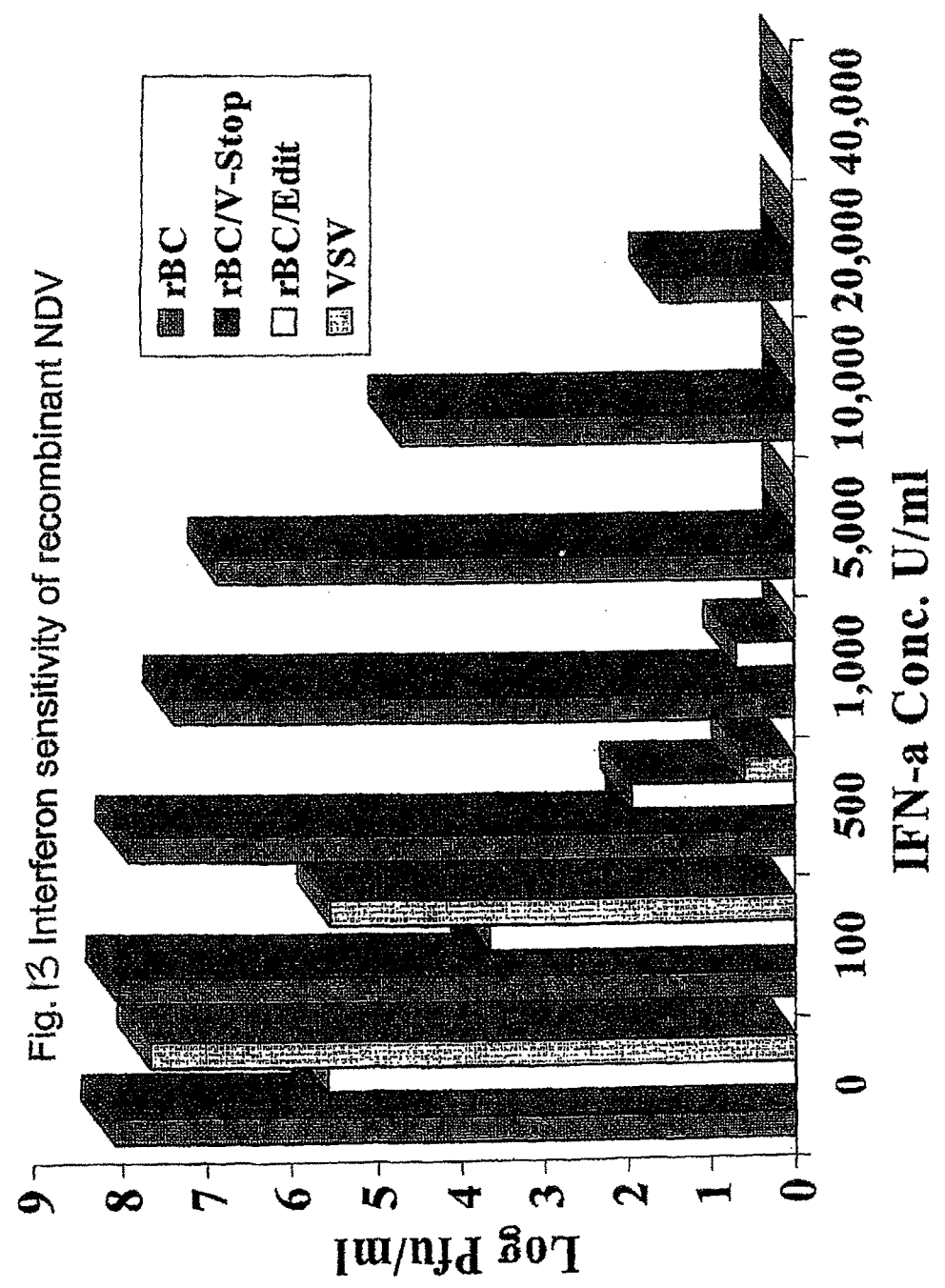

Rescue of Newcastle disease viruses from cloned cDNAs and expression vectors. By reverse genetics technology, several rNDV expressing additional genes as transcriptional units were recovered (Huang et al., "High-level expression of a foreign gene from the most 3'-proximal locus of a recombinant Newcastle disease virus," *J Gen Virol* 82:1729-36 (2001); Krishnamurthy et al., "Recovery of a virulent strain of Newcastle disease virus from cloned cDNA: expression of a foreign gene results in growth retardation and attenuation," *Virology* 278:168-82 (2000)), including one carrying EGFP. The recombinant viruses used in this study are shown in Table 1. The recovered recombinant viruses exhibited all of the biological phenotypes of their parental natural isolates. The rBC-EGFP virus stably expressed EGFP even after ten passages in 9-11 day-old embryonated chicken eggs and fifteen passages in DFI cells. The V mutants yielded 100-fold lower titers than the wild-type virus in interferon-competent chicken embryo fibroblast (DF1), cells while in interferon defective Vero cells, the growth kinetics and magnitude of these viruses were similar to that of rBeaudette C virus. The alteration of the protease cleavage site of the F protein of rLaSota virus to that of rBeaudette C virus resulted in a virus which did not require exogenous protease for propagation in cell culture and whose in vitro growth kinetics was very similar to that of rBeaudette C virus. The V protein defective viruses and the rLaSota V. F. virus were potent inducers of IFN in a bioassay employing vesicular stomatitis virus and they were highly sensitive to exogenously added IFN-α, The rBeaudette C virus is a poor inducer of IFN and is more resistant to the action of IFNα/β (FIG. 13). The chicken anemia virus (CAV) VP3 gene expression was confirmed with polyclonal antibody against CAV and the virus grew at least one log higher than the parental strain in DF1 cells.

TABLE 1

| Recombinant Viruses | |
|---|---|
| Virus | Additional/replaced/mutated gene |
| Recombinant Beaudette C (rBC) | None |
| Recombinant LaSota (rLaSota) | None |
| Recombinant LaSota V.F. (rLaSotaVF) | Virulent Fusion (V.F.) protein cleavage site |
| Recombinant Beaudette C-Edit (rBC-Edit) | V protein edit site mutant |
| Recombinant Beaudette C-V stop (rBC CV) | V protein defective mutant |
| Recombinant LaSota BC HN (rLaSota BCHN) | Beaudette C HN |
| Recombinant Beaudette C GFP (rBC-EGFP) | Enhanced Green fluorescent protein |
| Recombinant Beaudette C-VP3 (rBC-VP3) | Chicken anemia virus (CAV) apoptin gene |

Attenuation of NDV is dependent Upon its ability to antagonize interferon-alpha. Earlier studies demonstrated that V protein defective rNDV exhibit impaired growth in chicken embryo (CE) cell cultures, but replicated similar to the parental type in Vero cells, suggesting virus replication as a function of host cell IFN competence. Transient expression of the carboxyl-terminal portion of the V protein abolished the growth defect in interferon-competent CE cells. The parental virus grew to high titers in chicken embryos of different gestational ages, whereas the mutant viruses showed an age-dependent phenomenon, growing to a lower titer in more-developed embryos, corresponding to their ability to induce IFN. An interferon (IFN) sensitivity assay confirmed that the parental virus was more resistant to the antiviral effects of IFN than the mutant viruses. Moreover, infection with the parental virus resulted in STAT1 protein degradation, but not with the mutant viruses (Huang et al, 2003). These findings indicate that the V protein of NDV possesses the ability to inhibit alpha IFN and that the IFN inhibitory function lies in the carboxyl-terminal domain. Pathogenicity studies in chickens, the natural host, indicated that the V protein of NDV significantly contributes to the virus virulence, and V protein defective viruses are attenuated. The V protein of NDV is an IFN antagonist (38, Huang et al. 2003), and it selectively degrades the cellular STAT-1 protein for blocking IFN-alpha expression in virus infected cells (Luang et al, 2003). Addition of an apoptotic gene as an extra cistron in the rBC-edit or rBC-V stop viruses (V-defective viruses) resulted in the reversion of those respective P gene editing sites to that of the wild type with a functional V protein expression. The V protein of NDV has been reported to be antiapoptotic (Park et al., "Newcastle disease virus (NDV)-based assay demonstrates interferon-antagonist activity for the NDV V protein and the Nipah virus V, W, and C proteins," *J Virol* 77:1501-11 (2003)). It appears that the V protein is a multifunctional protein with a major role in the attenuation of NDV to its natural host.

Recombinant NDV trigger antiviral responses in infected cells. NDV has been reported to replicate selectively in tumor cells as against normal human cells. This tumor selectivity has been attributed to the antiviral action of interferon in normal human cells. In order to understand the mechanistic basis of virus replication in tumor cells by rNDV, a combination of assays was used to detect early signaling events triggered by these viruses that lead to transcriptional activation of antiviral and other cellular genes. V protein deleted-rBC-edit and rLaSota V.F. viruses induced at least twenty to thirty times higher levels of IFN alo in chicken embryo fibroblast cells in a bioassay employing VSV (Huang et al, 2003). All the tested strains induced interferon-beta (IFN-(3) by ELISA in all the cancer cell lines tested at 48 h post-infection with no significant differences between the strains. The presence or absence of V protein in NDV did not alter the rate of induction of IFN-β in any of the cancer cell lines (250 pg/mL by rBC-edit virus in HT-29 cells to 1250 μg/mL by rBC virus in CaCo2 cells) or in DFI cells (FIG. 14). Kinetic assays indicated that rBC-edit virus induced IFN-β as early as 6 h PI and sustained up to 48 h. With other rNDV, there was a delay in the induction of IFN-6, with increasing levels of detectable IFN between 48-72 h PI (FIG. 15). But, despite higher levels of IFN-β virus replication was not impaired in any of these cell lines (Table 2). Highest levels of IFN-α were produced in PC3 cells and in moderate amounts in HuTu 80 fibroblast cells after rNDV infection (FIG. 16). In PC3 cells, IFN antagonist V protein-defective NDV induced the higher levels of IFN-α than its parental type. Kinetic assays of IFN-α in HuTu 80 fibroblast cells revealed that IFN-α was induced late in the replication cycle (38 h PI) and rBC-edit virus induced at least 2-4 fold higher IFN-α than the parental rBC with intact IFN antagonistic activity (FIG. 17). Fortification of the IFN-β induced antiviral state by the induction of members of the IFN-α family seems to be necessary to prevent virus replication in cancer cells. RANTES, another primary response gene was induced only in the fibroblast cell lines (FIG. 18). IP-10 was induced in fibroblast cell lines such as HT1080, prostate cancer epithelial cell line PC3, HuTu 80 intestinal epithelial cells, and colon cancer cell lines CaCo2 and HT29 (FIG. 19). Secondary response genes that require the production of IFN-β protein and the autocrine or paracrine activation of the JAKISTAT pathway were differentially induced by IFN resistant and IFN-sensitive (V defective) viruses depending on the cell lines (see IRF-7 in FIG. 20). No impairment in the induction of JAK/STAT pathway was shown in tumor cells (see STAT 1 or STAT 2 in FIG. 21), and therefore the signaling block must be downstream of the JAK/STAT pathway. As a consequence of impaired IRF-7 production, tertiary response genes like IFN-α were not induced in many of the cell lines. These results indicate that rNDV trigger activation of IRF-3 and the subsequent transcription of a cohort of genes to induce the primary antiviral state but through coordinated expression of viral gene products either blunts secondary and tertiary responses or exploits the tumor specific defects in the IFN pathway. The absence of tertiary response (IFN-α) failed to fortify the primary antiviral state, thus permitting virus replication. In fact, it has been shown by elegant deletion experiments that in the absence of adaptor molecules such as FADD, RIP1 or TBK-1, downstream IFN signaling events after IRF-3 phosphorylation may be compromised, resulting in enhanced VSV replication.

Recombinant NDV strains are highly lytic for members of the NCI Panel and Other cancer cell lines. To assess the oncolytic properties of the rNDV strains, representative cell lines from the NCI-60 human tumor cell panel and other tumor cell lines (15 cell lines from a spectrum of malignancies) were infected with either recombinant LaSota (rLaSota), rLaSota with Beaudette C fusion protein cleavage site (rLaSota V.F.), rLaSota with Beaudette C hemagglutinin (rLaSota BCHN), rBC, rBC with chicken anemia virus apoptin gene insert (rBC-VP3), rBC with enhanced green fluorescent protein (rBC-EGFP), or rBC with a V-protein edit site mutant (rBC-Edit) viruses, and assayed for metabolic cell death by the WST-1 assay 48 h later. The rNDVs were able to infect and induce cytolysis in a wide range of tumor cell types (Table 2). The rLaSota virus was cytotoxic only to HeLa and HEpG2 cells and required an MOI of 10 and 1.0, respectively, for cytolysis. On the other hand, the rLaSota V.F. virus was cytotoxic (mean $EC_{50}$-0.84) to twelve of the fourteen tested cell lines except T84 colon cancer cells and MCF-7 breast carcinoma cells, while the IFN-sensitive rBC-edit virus was cytolytic to ten out of fourteen cell lines (mean $EC_{50}$=0.12). The mean $EC_{50}$ of rBC-VP3 virus was extremely low (0.012) for most of the cancer cell types, except for some of the colon cancer cells. Human tumor cells of neuroectodermal, mesenchymal, and epithelial origins could be infected and lysed by rNDV. Cytopathic effects (CPE) in rNDV infected cells were cell-to-cell fusion with syncytia formation, rounding and increased granularity of cells leading to destruction of monolayer of adherent cells or cytotoxicity of suspension cells (FIG. 22). The parental rBC and rBC-EGFP viruses were cytolytic to eight of the fourteen tested cell lines (mean $EC_{50}$=0.22 and 0.27, respectively). The CPE in rNDV infected cells were cell-to-cell fusion with syncytia formation, rounding and increased granularity of cells leading to destruction of monolayer of adherent cells (FIG. 6A-P) or granularity and cell death in suspension cells such as THP-1 and CCRF-CEM. In SV-HUC1 immortalized human uroepithelial cells, NDV replication was severely restricted (FIG. 6Q) and no CPE was observed up to an MOI of 10. As the rLaSota virus was found to be poorly cytolytic in WST-1 cytotoxic assay, it was not studied further.

Replication of rNDV is suppressed in normal cells. The data indicated that all strains of rNDV replicate to high levels in most of the malignant cell lines, inducing cytolysis while producing significant levels of IFN-β. Since IFN pathway is defective in many transformed cell lines (James C D et al, 1991), the IFN-β produced by rNDV following infection fails to exert significant antiviral activity that would impede viral replication. However, because normal cells retain regular IFN responses, it is plausible, that such cells should be considerably resistant to rNDV as IFN-β produced by the rNDV can function in a manner involving autocrine and paracrine mechanisms to exert a potent antiviral state. Naturally occurring oncolytic strains of NDV have shown to be replication-selective in tumor cells and replication-incompetent in normal human cells (Reichard et al, 1992) and this has been attributed to the IFN-competency of normal cells (Lorence et al, European patent). To confirm this, the susceptibility of non-tumorigenic, SV-40 immortalized SV-HUC 1 uroepithelial cells was examined (Reznikoff et al, 1990 U.S. Pat. No. 4,980,290, ATCC #CRL-9520). The cell viability after infecting with different MOI of rNDV was tested by the WST-1 assay at 48 h PI. No CPE was observed in these cells after infection with rMV. Moreover the viability of these cells following infection was invariable at up to 72 h PL. In these cells, the titers of infectious NDV were at least four-to-ten logs lower than what was obtained in tumor cells. The rBC-edit virus replicated ten-logs higher in HuTu 80 tumor cells than SV-HUCI cells. All the rNDV strains induced higher levels of IFN-β in these cells, and V-deleted virus induced at least two-fold higher levels of IFN-β (FIG. 23), suggesting that V-protein of NDV probably blocks IFN-β induction, upstream of IRF-3 phosphorylation. RIG-I; a DEXD/H box RNA helicase has recently shown to be required for efficient IFN-βinduction by NDV (Yoneyama et al, 2004). All rNDV strains induced IFN-α to significant levels with no remarkable differences. Similarly, all rNDV induced INF-α in moderate levels at 48 h PI with no significant differences among them. These results would suggest that rNDV inhibits its own replication in normal, non-transformed cells through activation of IFN antiviral pathway and is tumor selective due to defects in the IFN pathway in tumor cells. Given these results, defects or down-regulation of components of the IFN pathway may be a common feature of a broad range of malignancies (Wong et al, 1997; Abril et at 1996; Sun et al, 1998; Shimada et al, 1998; Strong et al, 1998; Stojdl et al, 2000; Stojdl et al, 2003), and these defects may be responsible for the tumor selectivity demonstrated by a variety of oncolytic viruses (Cassady et al, 1998; Lorene et al, 1994 (fibrosarcoma); Lorene et al, 1994 (neuroblastoma); Stojdl et al, 2000; Stojdl et al, 2003). ras activation or p53 status does not dictate NDV permissiveness and cytotoxicity.

ras Activation or p53 status does not dictate NDV Permissiveness and cytotoxicity. From the analysis of results of virus replication and cytotoxicity in various cell lines with or without ras activation, it appears that ras abetment is not a prerequisite for NDV replication and cytotoxicity (Table 3/FIG. 24). To demonstrate that NDV can successfully enter and produce transcripts and protein in both ras mutant or wild type cells (e.g., N-ras activated HT 1080 and ras-wild type PC3 cells), NDV transcripts and proteins were produced in these cells. To examine viral transcription, RNA was extracted for RT PCR to assess the presence of NDV transcripts. Infected cells supported the production of the NDV transcripts irrespective of whether they were ras-activated or not. To assess NDV protein synthesis, the cells were infected with rBC-EGFP virus or mock infected, and examined for EGFP expression by epifluoresoence microscopy. There was no selective preference in the expression of virally encoded EGFP with respect to ras activation in cancer cells (FIG. 22). Both types of cells allowed effective synthesis of viral proteins, as indicated by EGFP expression. To confirm that authentic NDV proteins are also expressed in these cells, rBC-infected cells were examined for the expression of NDV HN by an indirect inmunofluorescence, using anti HN monoclonal antibodies. Further, no significant increase in virus replication was observed in ras-transformed cells (FIG. 24) by a plaque assay in highly permissive DFI cells. On the contrary, the highest level of virus replication was observed in CaW cells with wild-type ras (Table 3). IFN-sensitive rBC-edit and rBC V stop viruses grew two logs lower than their parental type in both cell lines, suggesting that ras-mediated PKR inhibition does not provide selective advantage for tumor-specific replication. Further, the cytopathic effects (CPE) induced by rNDV in HT1080 and PC3 cells were determined. In both cell lines, irrespective of m.o.i. of infection (10 or 0.01), characteristic CPE in the form of syncytia and cell death was observed, suggesting that virus replication, release, and cell-to-cell spread is not hampered in the absence of ras activation. Similarly, no significant differences in viral protein expression or replication in cells with wild type or mutant p53 were observed (FIG. 25A-C). These studies show that ras oncogene activation and mutations in p53 gene do not confer enhanced susceptibility to NDV induced oncolysis.

Induction of apoptosis by rNDV mediates cytolysis in tumor cells. To determine the nature of rNDV induced cytolysis, work was conducted to examine whether rNDV is oncolytic through direct induction of apoptosis. Various tumor cells were infected with rNDV at 0.01 MOI, and examined for markers of apoptosis viz., morphological changes by DAPI staining, phosphatidyl serine externalization by Annexin V staining (FIG. 26), and intranucleosomal DNA fragmentation by DNA laddering techniques. In most cases, rNDV infection led to cell death characterized by several hallmarks of apoptosis, including morphological changes of rounding and refraction, loss of adherence, development of pyknotic nuclei (FIG. 7A), and phosphatidyl serine externalization (FIG. 7B). Apoptosis appeared from 6 h after rNDV infection, since then the cells displayed typical Annexin V-positive labeling. DNA laddering was observed in most of the cell lines following infection with rNDV as early as 8 h PI (FIGS. 7C-D and 27).

NDV induces apoptosis of tumor cells independent of IFN signaling. Many studies have shown that IPN-α activates an apoptosis program in several tumor cell lines and primary tumor cells (Chen et al., "A novel influenza A virus mitochondrial protein that induces cell death," *Nat Mod* 7:130612 (2001), Pokrovskaja et al., "Alternative signaling pathways regulating type I interferon-induced apoptosis," *J Interferon Cytokine Res* 25:799-810 (2005), Sangfelt et al., "Induction of apoptosis and inhibition of cell growth are independent responses to interferon-alpha in hematopoietic cell lines," *Cell Growth Differ* 8:343-52 (1997)). In order to analyze the role of IFN in NDV induced apoptosis, cell lines that respond to exogenous or endogenous IFN or those that do not respond to IFN due to specific mutations or defects were infected. Apoptosis was induced in human tumor cells independent of IFN signaling, as apoptosis was detected in IFN responsive cell lines (e.g., HeLa, HT1080, 2fTGH) or IFN-unresponsive cell lines (e.g., PC3 and U3A) (FIG. 7E). Further, most of the tested human tumor cell lines were not able to produce IFN-α after NDV infection but showed NDV-induced apoptosis (data not shown).

Death receptor signaling in tumor cells following NDV Infection. To identify the signaling pathways that mediate apoptosis in tumor cells, the role of TNF-α and TRAIL, members of the death receptor pathway, was examined in NDV-induced apoptosis. rNDV induced TNF-α as early as 12 h PI, and the levels were increasing even at 72 h PI, irrespective of the strain of NDV (FIGS. 8A and 28) in tumor cells. However, the highest levels of soluble TNF-αremained below 1 pg/mL in tumor cell lines and 4 to 6 pg/mL in immortalized SV-HUCI, normal human cells (FIGS. 8B and 29). Even at 6 pg/mL concentration, no apoptosis was detected in SV-HUCI cells, suggesting that NDV induced TNF-α does not necessarily mediate apoptosis. TRAIL is a member of the TNF family and, together with its functional and decoy receptors, comprises one of the death receptor pathways for apoptosis. Soluble TRAIL was detected by ELISA in DF1 cells and only in some of the tumor cell lines (FIGS. 8C and 30). In TRAIL resistant colorectal cancer cells such as HT-29 and CaCo2, apoptosis was induced by rNDV. Surface expression of TRAIL was detected in many of the cancer cell lines at 48 h PI, suggesting that human TRAIL is essentially a membrane-bound protein. Time-course studies by Western blot in HuTu80 cells indicated that TRAIL expression commenced only at 14 h PI (FIGS. 8D and 31), suggesting that TRAIL-mediated apoptosis is a late event in NDV-infected cells. Treatment of rBC-EGFP-infected HuTu80 cells with anti-TRAIL antibody (MAB 687, R&D systems) inhibited apoptosis but not the viral replication of rBC-EGFP virus, demonstrable by EGFP expression and viral plaque assay.

Figure 34:
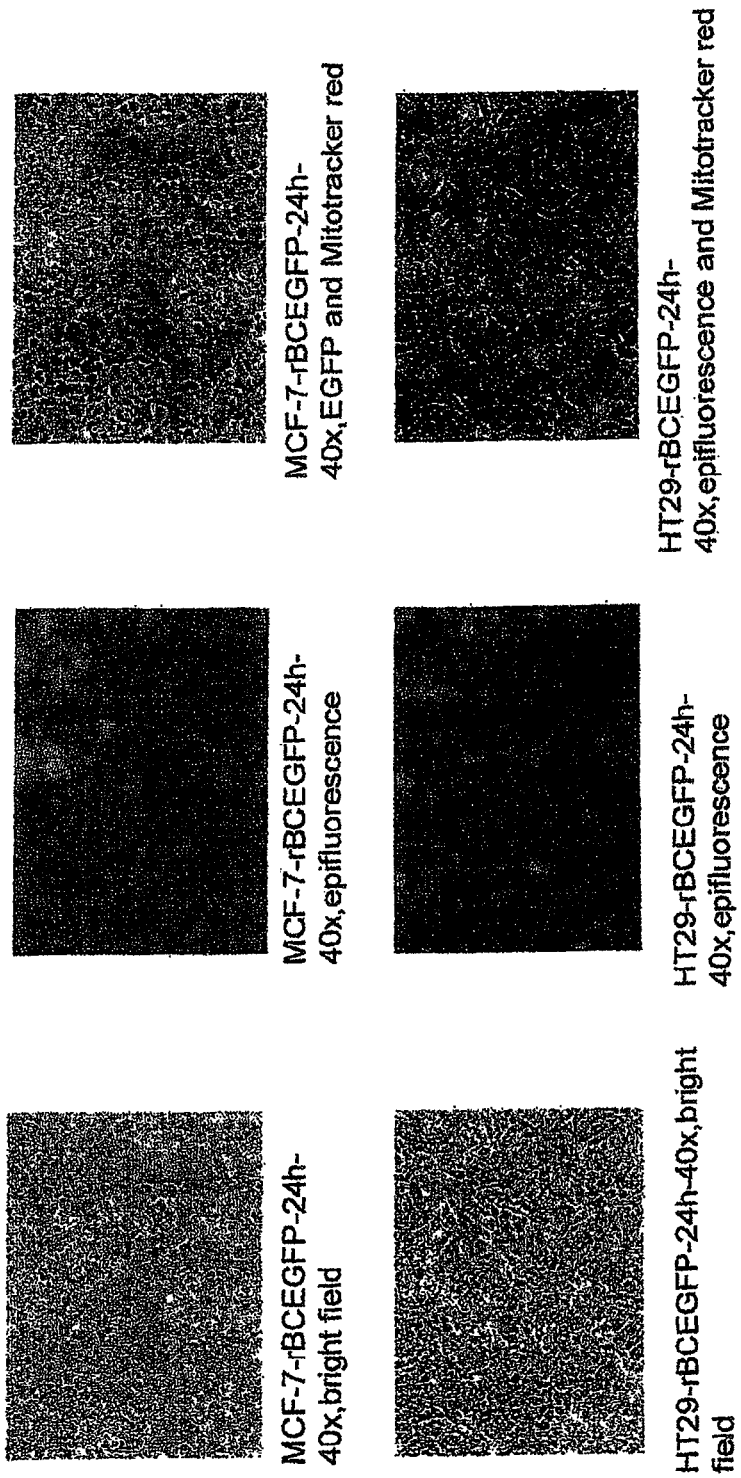
FIG. 34. Cytopathic effects, reporter gene expression, and mitochondrial membrane potential in rNDV infected tumor cells.

Caspase-8 is activated but dispensable for apoptosis Induction after NDV Infection of Tumor Cells. Death receptor signaling by ligand binding at the cell surface leads to the formation of death inducing signaling complex (DISC) and activation of caspase-8. Therefore, the activation of caspase-8 in NDV-infected cells was examined. NDV infection activated caspase-8 in many of the tumor cell lines at 48 h PI (FIGS. 9A and 32). Caspase-8 was activated independent of IFN responsiveness, indicating that cells respond to NDV with apoptosis either in the presence or absence of IFN signaling (Weaver et al., "Apoptosis is promoted by the dsRNA-activated factor (DRAF1) during vital infection independent of the action of interferon or p53," *FASEB J* 15:501-15 (2001)). Caspase-8 was activated in a bi-phasic manner commencing at 12 h with peak activation occurring at 32 h PI for the rBC virus in HuTu80 cells. Interestingly, rLaSota V.F. and rBC-edit viruses induced caspase-8 late in the infection cycle (FIGS. 9B and 33), following a similar biphasic activation, correlating with the onset of CPE. This bi-phasic activation indicated that other pathways might amplify caspase-8 induced pathways or caspase-8 is induced by additional pathways, operating independently of death receptor signaling. Further support for this assumption stemmed from the fact that rapid CPE and apoptosic DNA laddering was evident after rNDV infection in TRAIL-sensitive, caspase-8 methylated SHSY-5Y neuroblastoma cells (FIGS. 6 and 7D), and TRAIL-resistant CSCo2, and HT29 colon carcinoma cells (FIGS. 7E and 34). In CaCo2, and HT29 cells, apoptosis was induced by NDV without any caspase 8 activation. Loss of caspase-8 expression by gene methylation is suggested to be the reason for TRAIL resistance in neuroblastoma cells (Teitz et al., "Caspase 8 is deleted or silenced preferentially in childhood neuroblastomas with amplification of MYCN," *Nat Med* 6:529-35 (2000)). Caspase-8 activation in neuroblastoma cells commenced only after TRAIL expression was evident in NDV-infected cells (FIG. 9C). Recent evidence suggests that SH-SY5Y neuroblastoma cells become TRAIL sensitive and FADD-positive, and induce caspase-8 upon stimulation with TRAIL and IFN-γ (Johnsen et al., "Synergistic induction of apoptosis in neuroblastoma cells using a combination of cytostatic drugs with interferon-gamma and TRAIL," *Int J Oncol* 25:1849-57 (2004)). As these results suggested that caspase-8 is probably not the initiator caspase, evidence was sought to determine whether NDV infection activated intrinsic, mitochondrial-associated apoptosic signaling pathways may operate earlier than death-receptor pathways.

Mitochondrial membrane potential is not maintained following NDV Infection. Cell death at the mitochondrial level is initiated by perturbation of the mitochondrial membrane leading to the release of various proapoptotic factors. To identify the drop in mitochondrial membrane potential ($\Delta\psi_m$), mock and NDV-infected cells were stained with MitoTracker Red CMX-Ros dye (FIGS. 10A-I and 34). The CMX-Ros dye is taken up only by actively respiring mitochondria with intact $\Delta\psi_m$. The DNA-binding DAPI fluorophore was then used to delineate the nuclear morphology. NDV-infected cells which had a disruption of the $\Delta\psi_m$ and undergoing apoptosis were detected by the diffuse cytoplasmic pattern of CMX-Ros (FIGS. 10A-I and 34) with condensed chromatin. Cells with intact mitochondrial transmembrane potential displayed punctuate staining with CMX-Ros (FIG. 10J-L). Following a drop of $\Delta\psi_m$, cytochrome c can be released from mitochondria through the opened mitochondrial pores. Therefore, localization of cytochrome c after NDV infection was investigated. Mitochondrial and cytosolic extracts from mock and virus-infected cells were prepared by subcellular fractionation and analyzed by Western blot. In NDV-infected cells, the level of cytochrome c in cytosol increased two-fold compared to the level observed in mock infected cells (data not shown). These results indicate that cytochrome C is released from the mitochondria during apoptosis induced by NDV, and that the intrinsic mitochondrial pathway is initiated after infection with NDV.

Smac/DIABLO is not released from the mitochondria following NDV infection. Inhibitor-of-apoptosis proteins (IAPs) inhibit the enzymatic activity of caspases (Thornberry et al., "Caspases: enemies within," *Science* 281: 1312-6 (1998)). IAP-mediated inhibition of apoptosis is countered by Smac/DIABLO and Smac protein is secreted from mitochondria into the cytosol during apoptosis (Du et al., "Smac, a mitochondrial protein that promotes cytochrome c-dependent caspase activation by eliminating IAP inhibition," *Cell* 102:33-42 (2000); Verhagen et al., "Identification of DIABLO, a mammalian protein that promotes apoptosis by binding to and antagonizing IAP proteins," *Cell* 102:43-53 (2000)). Synthetic Smac mimic molecules have been shown to potentiate TRAIL, and TNF-a-mediated cell death (Fuida et al., "Smac agonists sensitize for Apo2L/TRAIL- or anticancer drug-induced apoptosis and induce regression of malignant glioma in vivo," *Nat Med* 8:808-15 (2002); Li et al., "A small molecule Smac mimic potentiates TRAIL- and TNF-alpha-mediated cell death," *Science* 305:1471-4 (2004)). Secretion of Smac into the cytosol after infecting HuTu 80 cells with rNDV was therefore examined. Mitochondrion-free lysates were prepared from both mock and NDV-infected cells at specified time points and analyzed by Western blot for the presence of cytosolic Smac/DIABLO. No Smac expression was detected in rNDV infected cells at various time points up to 48 h PI in HuTu 80 cells.

Caspase-9 is activated early after NDV infection. In the cytosol, cytochrome c forms an apoptosome with Apaf-1, procaspase-9, leading to the activation of caspase-9. Caspase-9 was found to be activated by a fluorogenic substrate assay in most of the tested cell lines (FIGS. 11A and 35) after rNDV infection. Significant levels of Caspase-9 were induced as early as 6 h PI in HuTu 80 cells, and it also followed a bi-phasic pattern of activation (FIGS. 11B and 36). Recombinant LaSota V.F. and rBC-edit viruses initiated low levels of caspase-9 between 8 and 10 h PI followed by another wave of significant induction after 48 h PI. Similarly, in SH-SY5Y neuroblastoma cells, caspase-9 activation occurred by 12 h after infection with rNDV (FIG. 11C). These results suggest that apoptosis in NDV-infected tumor cells probably commence intrinsically through the dsRNA intermediates and possibly through ER stress, leading to mitochondrial membrane destabilization and caspase-9 activation.

Effector caspase activation. Having shown that NDV infection resulted in the activation of both death-receptor and mitochondrion-associated pathways, the activation of caspase-3 was tested. As shown in FIGS. 12A and 37, caspase-3 activation was detected by a fluorogenic substrate assay in many of the cell lines associated with apoptosis. Caspase-3 followed a similar bi-phasic activation as that of Caspase-9 (FIGS. 12B and 38). In caspase-3 null, MCF-7 breast cancer cells, rNDV strains replicated, although at reduced efficiency, but failed to exert cytolysis ($EC_{50}>10$), consistent with the idea that caspase-mediated cell death is the predominant mechanism of oncolysis by NDV. In caspase-8 methylated SH-SY5Y neuroblastoma cells, caspase-3 was detected as early as 8 h PI, indicating that other initiator pathways are involved in effector caspase activation (FIG. 12C). IFN-sensitive rBC-edit virus induced caspase-3 in HuTu80 cells at 32 h PI while it induced caspase-9 as early as 10 h PI, but caspase-8 only at 48 h PI, reinforcing the view that intrinsic apoptosic pathways operate early in NDV-infected cells (FIG. 12B). Classically, caspase-8 has been viewed as an initiator caspase involved in death receptor signaling (Wilson, "Apoptosic signal transduction: emerging pathways," *Biochem Cell Biol* 76:573-82 (1998)). However, these results demonstrated that caspase-8 was activated only after caspase-9 and caspase-3 were activated. This time course suggested that caspase-8 was not the primary initiator caspase involved in NDV-mediated apoptosis. These results also suggest that caspase-8 activation probably occurs as an indirect effect of activation of caspases-9 and -3 (Wieder et al., "Activation of caspase-8 in drug-induced apoptosis of B-lymphoid cells is independent of CD95/Fas receptor-ligand interaction and occurs downstream of caspase-3," *Blood* 97:1378-87 (2001)) or through the death receptor pathway late in the infection. It is probable that other initiator caspases might be involved depending on the cell type and virus strain in effector caspase activation.

NDV induced apoptosis is caspase-dependent. To identify whether rNDV induced apoptosis is entirely dependent on caspase activation, HuTu80 epithelial cells were pretreated with a broad-specificity caspase inhibitor zVAD-fmk or with relatively specific inhibitors of caspase-9 (zLEHD-fmk), caspase-3 (zDEVD-fmk), and caspase-8 (zLETD-fmk) and infected with rBC-EGFP. The expression of EGFP was monitored by epifluorescence microscopy and virus content in the supernatant was determined by a plaque assay on DF1 cells, at specified intervals. The broad-specificity caspase inhibitor zVAD-fmk was able to inhibit rNDV-triggered cytolysis completely until 48 h, indicating that NDV-mediated cytotoxicity is caspase-dependent. But, after 48 h PI, CPE appeared in the form of syncytia, and cell rounding, indicating that rNDV can induce caspase-independent lysis, perhaps as a direct result of viral replication. Intranucleosomal DNA fragmentation assay of infected cells confirmed apoptosis. Furthermore, despite the block in apoptosis, titers of infectious virus in zVAD-fmk treated cells were similar to those in untreated cells (FIG. 2E), implying that apoptosis is not required by the virus as a mechanism to facilitate its replication. Caspase-8 and caspase-9 inhibitors also suppressed morphological and biochemical alteration of NDV-infected cells until 48 h PI. But, none of them were able to individually protect HuTu80 cells from rNDV-induced apoptosis, suggesting that rNDV triggers multiple caspase-dependent pathways in these cells. From the results above, it may be inferred that NDV triggers apoptosis by a rapid dissociation of the mitochondrion membrane potential, the release of cytochrome c, and the activation of caspase-9. Further, caspase-8 was detected late in the infection cycle, suggesting that multiple pathways that lead to the death of NDV-infected cells could be acting after an initial pro-apoptosic signal subsequent to the entry of the virus.

TABLE 2

Mutant NDV strains are highly lytic on members of the NCI panel and other cancer cell lines

| Cell line | rLaSota Sensitivity (%) | MOI | rLaSota V.F. Sensitivity (%) | MOI | rBeaudette C (rBC) Sensitivity (%) | MOI | rBC-EGFP Sensitivity (%) | MOI | rBC-edit Sensitivity (%) | MOI | rBC-CAV VP3 Sensitivity (%) | MOI |
|---|---|---|---|---|---|---|---|---|---|---|---|---|
| THP-1 | 0 | >10 | 100 | 0.0001 | 100 | 0.0003 | 100 | 0.001 | 100 | 0.04 | 100 | 0.014 |
| CCRF-CEM | 0 | >10 | 100 | 0.283 | 0 | >10 | 0 | >10 | 0 | >10 | 100 | 0.0697 |
| Leukemia cell lines | 0 | >10 | 100 (2/2)* | 0.142 | 50 (1/2) | 0.003 | 50 (1/2) | 0.001 | 50 (1/2) | 0.04 | 100 (2/2) | 0.8767 |
| Prostate cancer | 0 | >10 | 100 (1/1) | 0.0005 | 100 (1/1) | 0.0001 | 100 (1/1) | 0.01 | 100 (1/1) | 0.0019 | 100 (1/1) | 0.00004 |
| HT1080 | 0 | >10 | 100 (1/1) | 3.5562 | 100 (1/1) | 0.02 | 100 (1/1) | 0.01 | 0 | >10 | 0 | >10 |
| HuTu80 | 0 | >10 | 100 (1/1) | 0.21725 | 100 (1/1) | 0.007 | 100 (1/1) | 0.01 | 100 (1/1) | 0.019 | 100 | 0.0002 |
| Cervical cancer (HeLn) | 100 | 10 | 100 (1/1) | 0.01 | 100 (1/1) | 0.72 | 100 (1/1) | 1.0 | 100 (1/1) | 0.007 | 100 (1/1) | 0.00005 |
| Liver cancer | 100 | 1.0 | 100 (1/1) | 0.0164 | 100 (1/1) | 0.019 | 100 (1/1) | 0.1 | 100 (1/1) | 0.0022 | 100 (1/1) | 0.00006 |
| CaCo2 | 0 | >10 | 100 | 0.0573 | 0 | >10 | 0 | >10 | 100 | 0.00004 | 100 | 0.0099 |
| CoLo205 | 0 | >10 | 100 | 0.0076 | 0 | >10 | 0 | >10 | 0 | >10 | 0 | >10 |
| SW 620 | 0 | >10 | 100 | 3.03 | 100 | 0.988 | 100 (1/1) | 1.0 | 100 | 1.081 | 0 | >10 |
| HT29 | 0 | >10 | 100 | 4.648 | 0 | >10 | 0 | >10 | 100 | 0.0006 | 0 | >10 |
| T84 | 0 | >10 | 0 | >10 | 0 | >10 | 0 | >10 | 100 | 0.0391 | 0 | >10 |
| Colon cancer cell lines | 0 | >10 | 80 (4/5) | 1.9357 | 20 (1/5) | 0.988 | 20 (1/5) | 1.0 | 80 (4/5) | 0.2802 | 20 (1/5) | 0.0099 |
| SH-SY5Y neuroblastoma | 0 | >10 | 100 | 0.002 | 100 | 0.0025 | 100 (1/1) | 0.01 | 100 | 0.0004 | — | — |
| Breast carcinoma (MCF-7) | 0 | >10 | 0 (0/1) | >10 | 0 (0/1) | >10 | 0 (0/1) | >10 | 0 (0.1) | >10 | — | >10 |
| All cell lines tested | 14 (2/14 | >10 | 86 (12/14) | 0.84 | 57 (8/14) | 0.22 | 57 (8/14) | 0.27 | 71 (10/14) | 0.12 | 54 (7/13) | 0.012 |

*Percent of cancer cell lines by tumor type deemed highly sensitive to virus-medicated killing. ( ) denote the number of highly susceptible cell lines out of the number of cell lines tested. Cell line considered highly susceptible if the $BC_{50} \le$ MOI of 1 following a $48^{th}$ infection. MOI represents average $BC_{50}$ (MOI) of susceptible cell lines. All the tested viruses are recombinant viruses derived by our established reverse genetics technique.

TABLE 3

Ras activation is not needed for permissiveness and cytotoxicity

| Cell line | Ras mutant status | Cell viability (MOI) rLaSota V.F. | rBC | rBC-Edit | Virus Titer (Pfu/mL) log10 rLaSota V.F. | rBC | rBC-Edit |
|---|---|---|---|---|---|---|---|
| THP-1* | K-ras and N-ras mutant | 0.0001 | 0.003 | 0.040 | $1.3 \times 10^4$ | $1.0 \times 10^3$ | <10 |
| CCRF-CEM* | ras mutant | 0.283 | >10 | >10 | ND | <10 | <10 |
| Leukemia cell lines | | 0.142 | 0.003 | 0.04 | | | |
| Prostate cancer (PC3*) | Wild type ras | 0.0005 | 0.0001 | 0.0019 | $1.0 \times 10^4$ | $2.0 \times 10^6$ | $2.1 \times 10^4$ |
| HT1080** | N-ras mutant | 3.5562 | 0.02 | >10 | $2.0 \times 10^4$ | $1.0 \times 10^6$ | $1.0 \times 10^4$ |
| HuTu80 | Wild type ras | 0.21725 | 0.007 | 0.019 | $1.5 \times 10^7$ | $3.0 \times 10^{11}$ | $1.0 \times 10^8$ |
| Cervical cancer (HeLa**) | Wild type ras | 0.01 | 0.72 | 0.007 | $1.5 \times 10^4$ | $1.9 \times 10^7$ | $1.9 \times 10^7$ |
| Hepatocarcinoma (HEpG2**) | N-ras mutant | 0.0164 | 0.019 | 0.0022 | $3.5 \times 10^5$ | $1.5 \times 10^7$ | $4.8 \times 10^6$ |
| CaCo2* | Wild type ras | 0.0573 | >10 | 0.00004 | $1.3 \times 10^8$ | $7.3 \times 10^{10}$ | $3.6 \times 10^8$ |
| CoLo205* | Wild type ras | 0.0076 | >10 | >10 | $1.0 \times 10^4$ | $1.5 \times 10^4$ | $1.0 \times 10^4$ |
| SW 620* | | 3.03 | 0.988 | 1.081 | ND | ND | ND |
| HT29* | Wild type ras | 4.648 | >10 | 0.0006 | $4.0 \times 10^4$ | $5.0 \times 10^4$ | $1.0 \times 10^4$ |
| T84* | | >10 | >10 | 0.0391 | $9.5 \times 10^5$ | $1.0 \times 10^5$ | $1.2 \times 10^5$ |
| Colon cancer cell lines | | 1.9357 | 0.988 | 0.2802 | | | |
| SHSY5Y neuroblastoma** | | 0.002 | 0.0025 | 0.0004 | $4.0 \times 10^4$ | $7.5 \times 10^5$ | $5.0 \times 10^6$ |
| Breast carcinoma (MCF-7**) | Wild type ras | >10 | >10 | >10 | $3.4 \times 10^3$ | $1.5 \times 10^3$ | $3.0 \times 10^2$ |

ND—Not done,
*p53 mutant,
**p53 wild type

While the present invention has been described in connection with various preferred embodiments, it will be understood by those skilled in the art that variations and modifications of the preferred embodiments described above may be made without departing from the scope of the invention. Other embodiments will be apparent to those skilled in the art from a consideration of the specification or from a practice of the invention disclosed herein. It is intended that the specification and the described examples are considered exemplary only.

What is claimed is:

1. A method for lysing tumor cells, comprising providing an oncolytically-effective amount of one or more recombinant Newcastle disease virus (rNDV) strains directly to one or more tumor cells,
   wherein the oncolytically-effective amount of the one or more rNDV strains requires an MOI of less than 10,
   wherein the one or more rNDV strains have been genetically modified to eliminate V protein expression,
   wherein the one or more rNDV strains have been genetically modified to include one or more transgenes that induce apoptosis in one or more tumor cell lines, selected from the group consisting of transgenes that induce production of pro-apoptotic proteins, transgenes that activate tumor suppressor genes, and transgenes that activate pro-apoptotic proteins, and
   wherein the one or more transgenes comprises chicken anemia virus apoptin gene.

2. The method of claim 1, wherein said tumor cells are lysed in vitro.

3. The method of claim 1, wherein the oncolytically-effective amount of one or more rNDV strains is administered directly into a tumor found in a patient.

4. A method for treating cancer in a patient suffering therefrom, comprising the step of administering directly into tumors of ecto- or endo- or mesodermal origin present in said patient a therapeutically-effective amount of a composition comprising one or more recombinant Newcastle disease virus (rNDV) strains,
   wherein the oncolytically-effective amount of the one or more rNDV strains requires an MOI of less than 10,
   wherein the one or more rNDV strains have been genetically modified to eliminate V protein expression, and
   wherein the one or more rNDV strains have been genetically modified to include chicken anemia virus apoptin gene.

5. A method for lysing tumor cells, comprising providing an oncolytically-effective amount of one or more recombinant Newcastle disease virus (rNDV) strains directly to one or more ecto- or endo- or mesodermal origin tumor cells,
   wherein the oncolytically-effective amount of the one or more recombinant Newcastle disease virus (rNDV) strains requires an MOI of less than 10,
   wherein the one or more rNDV strains have been genetically modified to eliminate V protein expression,
   wherein the one or more rNDV strains have been genetically modified to include one or more transgenes that induce apoptosis in one or more tumor cell lines, selected from the group consisting of transgenes that induce production of pro-apoptotic proteins, transgenes that activate tumor suppressor genes, and transgenes that activate pro-apoptotic proteins, and
   wherein the one or more transgenes comprises chicken anemia virus apoptin gene.

6. A method for treating cancer in a patient suffering therefrom, comprising the step of administering directly into tumors of ecto- or endo- or mesodermal origin present in said patient a therapeutically-effective amount of a composition comprising one or more recombinant Newcastle disease virus (rNDV) strains,
   wherein the therapeutically-effective amount of the composition requires an MOI of less than 10 of the one or more recombinant Newcastle disease virus (rNDV) strains,
   wherein the one or more rNDV strains have been genetically modified to eliminate V protein expression,
   wherein the one or more rNDV strains have been genetically modified to include one or more transgenes that induce apoptosis in one or more tumor cell lines, selected from the group consisting of transgenes that induce production of pro-apoptotic proteins, transgenes that activate tumor suppressor genes, and transgenes that activate pro-apoptotic proteins, and
   wherein the one or more transgenes comprises chicken anemia virus apoptin gene.

* * * * *